US012806180B2

(12) United States Patent
Millan et al.

(10) Patent No.: US 12,806,180 B2
(45) Date of Patent: Nov. 24, 2026

(54) METHODS AND COMPOSITIONS FOR TREATING ATHEROSCLEROSIS

(71) Applicant: Sanford Burnham Prebys Medical Discovery Institute, La Jolla, CA (US)

(72) Inventors: José Luis Millan, Valley Center, CA (US); David Magne, Lyons (FR)

(73) Assignee: SANFORD BURNHAM PREBYS MEDICAL DISCOVERY INSTITUTE, La Jolla, CA (US)

( * ) Notice: Subject to any disclaimer, the term of this patent is extended or adjusted under 35 U.S.C. 154(b) by 874 days.

(21) Appl. No.: 18/056,682

(22) Filed: Nov. 17, 2022

(65) Prior Publication Data

US 2023/0149374 A1 May 18, 2023

Related U.S. Application Data

(60) Provisional application No. 63/280,861, filed on Nov. 18, 2021.

(51) Int. Cl.

*A61K 31/44* (2006.01)
*A61K 31/47* (2006.01)
*A61K 45/06* (2006.01)
*A61P 9/10* (2006.01)
*C12N 15/113* (2010.01)
*C12Q 1/6883* (2018.01)

(52) U.S. Cl.

CPC .............. *A61K 31/44* (2013.01); *A61K 31/47* (2013.01); *A61K 45/06* (2013.01); *A61P 9/10* (2018.01); *C12N 15/1137* (2013.01); *C12Q 1/6883* (2013.01); *C12N 2310/122* (2013.01); *C12Q 2600/158* (2013.01)

(58) Field of Classification Search

CPC ........ A61K 31/44; A61K 31/47; A61K 45/06; A61P 9/10; C12N 15/1137; C12N 2310/122; C12Q 1/6883; C12Q 2600/158

See application file for complete search history.

(56) References Cited

U.S. PATENT DOCUMENTS 9,920,068 B2 3/2018 Miyazaki et al.
11,046,710 B2 6/2021 Miyazaki et al.

FOREIGN PATENT DOCUMENTS

WO WO-2013126608 A1 8/2013
WO WO-2016054056 A1 * 4/2016 ................ A61P 3/10
WO WO-2017007943 A1 1/2017
WO WO-2018119444 A1 6/2018

OTHER PUBLICATIONS

Dahl, Russell, et al. "Discovery and validation of a series of aryl sulfonamides as selective inhibitors of tissue-nonspecific alkaline phosphatase (TNAP)." Journal of medicinal chemistry 52.21 (2009): 6919-6925 (Year: 2009).*

Abramowitz et al. Serum alkaline phosphatase and phosphate and risk of mortality and hospitalization. Clin J Am Soc Nephrol 5(6):1064-71 (2010).

Aikawa et al. Osteogenesis associates with inflammation in early-stage atherosclerosis evaluated by molecular imaging in vivo. Circulation 116(24):2841-50 (2007).

Alvaro et al. The function of alkaline phosphatase in the liver: regulation of intrahepatic biliary epithelium secretory activities in the rat. Hepatology 32(2):174-84 (2000).

Beckonert et al. Metabolic profiling, metabolomic and metabonomic procedures for NMR spectroscopy of urine, plasma, serum and tissue extracts. Nat Protoc 2(11):2692-703 (2007).

Bessueille et al. Glucose stimulates chondrocyte differentiation of vascular smooth muscle cells and calcification: A possible role for IL-1. FEBS Lett 589(19 Pt B):2792-2804 (2015).

Bos et al. Atherosclerotic Carotid Plaque Composition and Incident Stroke and Coronary Events. J Am Coll Cardiol. 77(11): 1426-35 (2021).

Cai et al. Local and systemic insulin resistance resulting from hepatic activation of IKK-beta and NF-kappaB. Nat Med. 11(2):183-90 (2005).

Ceneri et al. Rac2 Modulates Atherosclerotic Calcification by Regulating Macrophage Interleukin-113 Production. Arterioscler Thromb Vasc Biol. 37(2):328-40 (2017).

Cole et al. Impaired phosphatidylcholine biosynthesis reduces atherosclerosis and prevents lipotoxic cardiac dysfunction in ApoE-/- Mice. Circ Res. 108(6):686-94 (2011).

Corbin et al. Choline metabolism provides novel insights into nonalcoholic fatty liver disease and its progression. Curr Opin Gastroenterol. 28(2):159-65 (2012).

Ehara et al. Spotty calcification typifies the culprit plaque in patients with acute myocardial infarction: an intravascular ultrasound study. Circulation 110(22):3424-9 (2004).

Espitia et al. Implication of molecular vascular smooth muscle cell heterogeneity among arterial beds in arterial calcification. PLoS One 13(1):e0191976 (2018).

Filipowicz et al. Associations of serum skeletal alkaline phosphatase with elevated C-reactive protein and mortality. Clin J Am Soc Nephrol. 8(1):26-32 (2013).

Gamez-Belmonte et al. Deficiency in Tissue Non-Specific Alkaline Phosphatase Leads to Steatohepatitis in Mice Fed a High Fat Diet Similar to That Produced by a Methionine and Choline Deficient Diet. Int J Mol Sci. 22(1):51 (2020).

Goettsch et al. Sortilin mediates vascular calcification via its recruitment into extracellular vesicles. J Clin Invest. 126(4):1323-36 (2016).

Goettsch et al. TNAP as a therapeutic target for cardiovascular calcification—a discussion of its pleiotropic functions in the body. Cardiovasc Res. 118(1):84-96 (2020).

(Continued)

*Primary Examiner* — Kamal A Saeed
*Assistant Examiner* — Quincy Mckoy
(74) *Attorney, Agent, or Firm* — Dickinson Wright PLLC

(57) ABSTRACT

Described herein are methods of treating atherosclerosis, including administering a tissue-nonspecific alkaline phosphatase (TNAP) inhibitor to a patient. Described herein are also methods of reducing microcalcifications in an atherosclerotic plaque, including administering a TNAP inhibitor to a patient. Described herein are also methods of preventing, arresting, or reducing the development of plaque calcifications in a patient, including administering a TNAP inhibitor to a patient.

19 Claims, 30 Drawing Sheets

(56) References Cited

OTHER PUBLICATIONS

Halling et al. Isozyme profile and tissue-origin of alkaline phosphatases in mouse serum. Bone 53(2):399-408 (2013).
Harmey et al. Concerted regulation of inorganic pyrophosphate and osteopontin by akp2, enppl, and ank: an integrated model of the pathogenesis of mineralization disorders. Am J Pathol. 164(4):1199-209 (2004).
Hessle et al. Tissue-nonspecific alkaline phosphatase and plasma cell membrane glycoprotein-1 are central antagonistic regulators of bone mineralization. PNAS USA 99(14):9445-9 (2002).
Hofmann et al. S100Al2 in vascular smooth muscle accelerates vascular calcification in apolipoprotein E-null mice by activating an osteogenic gene regulatory program. Arterioscler Thromb Vasc Biol. 31(2):337-44 (2011).
Irkle et al. Identifying active vascular microcalcification by (18)F-sodium fluoride positron emission tomography. Nat Commun. 6:7495 (2015).
Jacob et al. NMRProcFlow: a graphical and interactive tool dedicated to 1D spectra processing for NMR-based metabolomics. Metabolomics 13(4):36 (2017).
Jin et al. The Relationship Between Coronary Calcification and the Natural History of Coronary Artery Disease. JACC Cardiovasc Imaging 14(1):233-42 (2021).
Joshi et al. 18F-fluoride positron emission tomography for identification of ruptured and high-risk coronary atherosclerotic plaques: a prospective clinical trial. Lancet 383(9918):705-713 (2013).
Joshi et al. Does Vascular Calcification Accelerate Inflammation?: A Substudy of the dal-PLAQUE Trial. JAm Coll Cardiol. 67(1):69-78 (2016).
Kaliannan et al. Intestinal alkaline phosphatase prevents metabolic syndrome in mice. PNAS USA 110(17):7003-8 (2013).
Karlof et al. Correlation of computed tomography with carotid plaque transcriptomes associates calcification with lesion-stabilization. Atherosclerosis 288:175-85 (2019).
Kelly-Arnold et al. Revised microcalcification hypothesis for fibrous cap rupture in human coronary arteries. PNAS USA 110(26):10741-6 (2013).
Krishnamurthy et al. Associations of serum alkaline phosphatase with metabolic syndrome and mortality. Am J Med. 124(6):566.e1-7.27 (2011).
Lammers et al. Levels of alkaline phosphatase and bilirubin are surrogate end points of outcomes of patients with primary biliary cirrhosis: an international follow-up study. Gastroenterology 147(6):1338-49 (2014).
Lencel et al. Cell-specific effects of TNF-a and IL-1(3 on alkaline phosphatase: implication for syndesmophyte formation and vascular calcification. Lab Invest. 91(10):1434-42 (2011).
Li et al. Phosphatidylcholine and choline homeostasis. J Lipid Res 49(6):1187-94 (2008).
Lin et al. Runx2 deletion in smooth muscle cells inhibits vascular osteochondrogenesis and calcification but not atherosclerotic lesion formation. Cardiovasc Res. 112(2):606-16 (2016).
Luchtefeld et al. Signal transducer of inflammation gp130 modulates atherosclerosis in mice and man. J Exp Med. 204(8):1935-44 (2007).
Maldonado et al. A mechanistic analysis of the role of microcalcifications in atherosclerotic plaque stability: potential implications for plaque rupture. Am J Physiol Heart Circ Physiol. 303(5):H619-28 (2012).
Mechtouff et al. Simultaneous assessment of microcalcifications and morphological criteria of vulnerability in carotid artery plaque using hybrid. J Nucl Cardiol. 29(3):1064-1074 (2020).
Milian et al. Alkaline Phosphatase and Hypophosphatasia. Calcif Tissue Int. 98(4):398-416 (2016).
Morita et al. Structure and biological function of ENPP6, a choline-specific glycerophosphodiester-phosphodiesterase. Sci Rep. 6:20995 (2016).
Nadra et al. Effect of particle size on hydroxyapatite crystal-induced tumor necrosis factor alpha secretion by macrophages. Atherosclerosis 196(1):98-105 (2008).
Nadra et al. Proinflammatory activation of macrophages by basic calcium phosphate crystals via protein kinase C and MAP kinase pathways: a vicious cycle of inflammation and arterial calcification? Circ Res. 96(12):1248-56 (2005).
Nakahara et al. Calcification and Inflammation in Atherosclerosis: Which Is the Chicken, and Which Is the Egg? JAm Coll Cardiol. 67(1):79-80 (2016).
Nitschke et al. Generalized arterial calcification of infancy and pseudoxanthoma elasticum can be caused by mutations in either ENPP1 or ABCC6. Am J Hum Genet. 90(1):25-39 (2012).
Okin et al. The Effect of Sustained Inflammation on Hepatic Mevalonate Pathway Results in Hyperglycemia. Cell 165(2):343-56 (2016).
Ornello et al. Distribution and Temporal Trends From 1993 to 2015 of Ischemic Stroke Subtypes: A Systematic Review and Meta-Analysis. Stroke 49(4):814-9 (2018).
Panh et al. Association between serum alkaline phosphatase and coronary artery calcification in a sample of primary cardiovascular prevention patients. Atherosclerosis 260:81-6 (2017).
Pinkerton et al. Discovery of 5-((5-chloro-2-methoxyphenyl)sulfonamido)nicotinamide (SBI-425), a potent and orally bioavailable tissue-nonspecific alkaline phosphatase (TNAP) inhibitor. Bioorg Med Chem Lett 28(1):31-34 (2018).
Pugliese et al. The dark and bright side of atherosclerotic calcification. Atherosclerosis. 238(2):220-30 (2015).
Rattazzi et al. Calcification of advanced atherosclerotic lesions in the innominate arteries of ApoE-deficient mice: potential role of chondrocyte-like cells. Arterioscler Thromb Vasc Biol 25(7):1420-5 (2005).
Romanelli et al. Overexpression of tissue-nonspecific alkaline phosphatase (TNAP) in endothelial cells accelerates coronary artery disease in a mouse model of familial hypercholesterolemia. PLoS One 12(10):e0186426 (2017).
Rosenfeld et al. Advanced atherosclerotic lesions in the innominate artery of the ApoE knockout mouse. Arterioscler Thromb Vasc Biol. 20(12):2587-92 (2000).
Rutsch et al. Mutations in ENPP1 are associated with 'idiopathic' infantile arterial calcification. Nat Genet. 34(4):379-81 (2003).
Schierwagen et al. Seven weeks of Western diet in apolipoprotein-E-deficient mice induce metabolic syndrome and non-alcoholic steatohepatitis with liver fibrosis. Sci Rep. 5:12931 (2015).
Schippers et al. Phosphate Groups in the Lipid A Moiety Determine the Effects of LPS on Hepatic Stellate Cells: A Role for LPS-Dephosphorylating Activity in Liver Fibrosis. Cells 9(12):2708 (2020).
Sergienko et al. A method for direct assessment of tissue-nonspecific alkaline phosphatase (TNAP) inhibitors in blood samples. Methods Mol Biol. 1053:103-13 (2013).
Shaw et al. The never-ending story on coronary calcium: is it predictive, punitive, or protective? J Am Coll Cardiol. 65(13):1283-1285 (2015).
Sheen et al. Pathophysiological role of vascular smooth muscle alkaline phosphatase in medial artery calcification. J Bone Miner Res. 30(5):824-836 (2014).
Shioi et al. Plaque Calcification During Atherosclerosis Progression and Regression. J Atheroscler Thromb. 25(4):294-303 (2018).
Silvestre-Roig et al. Atherosclerotic Plaque Destabilization. Circulation Research 114(1):214-226 (Jan. 3, 2014).
Sun et al. Smooth muscle cell-specific runx2 deficiency inhibits vascular calcification. Circ Res. 111(5):543-52 (2012).
Tonelli et al. Relation between alkaline phosphatase, serum phosphate, and all-cause or cardiovascular mortality. Circulation 120(18):1784-92 (2009).
Van Der Heiden et al. SPECT/CT imaging of inflammation and calcification in human carotid atherosclerosis to identify the plaque at risk of rupture. J Nucl Cardiol. 29(5):2487-2496 (2021).
Vengrenyuk et al. A hypothesis for vulnerable plaque rupture due to stress-induced debonding around cellular microcalcifications in thin fibrous caps. PNAS USA 103(40):14678-83 (2006).

(56) References Cited

OTHER PUBLICATIONS

Vesey et al. 18F-Fluoride and 18F-Fluorodeoxyglucose Positron Emission Tomography After Transient Ischemic Attack or Minor Ischemic Stroke: Case-Control Study. Circ Cardiovasc Imaging 10(3):e004976 (2017).
Wannamethee et al. Alkaline phosphatase, serum phosphate, and incident cardiovascular disease and total mortality in older men. Arterioscler Thromb Vasc Biol. 33(5):1070-6 (2013).
Whyte et al. No vascular calcification on cardiac computed tomography spanning asfotase alfa treatment for an elderly woman with hypophosphatasia. Bone 122:231-6 (2019).
Whyte. Hypophosphatasia—aetiology, nosology, pathogenesis, diagnosis and treatment. Nat Rev Endocrinol. 12(4):233-46 (2016).
Wong et al. Hepatocyte-specific IKK13 expression aggravates atherosclerosis development in APOE*3-Leiden mice. Atherosclerosis 220(2):362-8 (2012).

* cited by examiner

METHODS AND COMPOSITIONS FOR TREATING ATHEROSCLEROSIS

CROSS-REFERENCE

This application claims the benefit of U.S. Provisional Application Ser. No. 63/280,861, filed on Nov. 18, 2021, the entirety of which is hereby incorporated by reference herein.

BACKGROUND

Field

One or more aspects of embodiments of the present disclosure relate to methods and compositions for treating atherosclerosis.

Description of the Related Technology

Cardiovascular diseases (CVDs) are responsible for 17.9 million deaths each year, which represents 31% of all deaths worldwide. Rupture of an atherosclerotic plaque is considered the primary reason for cardiovascular death, accounting for most myocardial infarction cases and about 20% of ischemic strokes. Therefore, identifying a vulnerable plaque is an important goal in cardiovascular research.

Acknowledged features of vulnerability include a large lipid and necrotic core, a thin fibrous cap, and intraplaque hemorrhage. In addition, microcalcifications, characterized by a size less than 10 μm and no macrocalcifications, negatively impact plaque stability. Clinically, microcalcifications can be imaged distinctly from macrocalcifications with $^{18}$F—NaF positron emission tomography (PET) because fluoride ions can replace hydroxyl ions in newly formed apatite crystals, but not in more mature, inert macrocalcifications. $^{18}$F—NaF accumulates in plaques with hallmarks of vulnerability, predicting future events. Microcalcifications may destabilize plaques through pro-inflammatory and mechanical mechanisms. In human macrophage cultures, microcalcifications measuring from 1 μm to 15 μm induce the release of TNF-α at levels inversely associated with crystal size. Microcalcifications can also exert a harmful mechanical stress and favor plaque rupture, especially when they develop in the fibrous cap. Nonetheless, in the absence of calcification inhibitors that could be used in vivo, the real impact of microcalcifications on plaque progression remains purely speculative.

SUMMARY

Some embodiments provide a method of treating atherosclerosis comprising administering a pharmaceutical composition comprising a therapeutically effective amount of a tissue-nonspecific alkaline phosphatase (TNAP) inhibitor to a patient. In some cases, treating atherosclerosis comprises reducing a number of microcalcifications in an atherosclerotic plaque, wherein administering the pharmaceutical composition comprising the therapeutically effective amount of the TNAP inhibitor reduces the number of microcalcifications in the atherosclerotic plaque. In some cases, treating atherosclerosis comprises preventing, arresting, or reducing the development of plaque calcifications, wherein administering the pharmaceutical composition comprising the therapeutically effective amount of the TNAP inhibitor prevents, arrests, or reduces the development of plaque calcifications.

In some cases, the TNAP inhibitor is at least one of a TNAP-targeting short hairpin RNA (shTNAP), a TNAP-targeting guide RNA (sgTNAP), a small molecule, or any combination thereof. In some instances, the TNAP inhibitor is a shTNAP, and the shTNAP is doxycycline-inducible. In some case, the TNAP inhibitor is a small molecule. In some instances, the small molecule is a compound of Formula I, or a pharmaceutically acceptable salt, polymorph, solvate, tautomer, metabolite, or N-oxide thereof:

(Formula I)

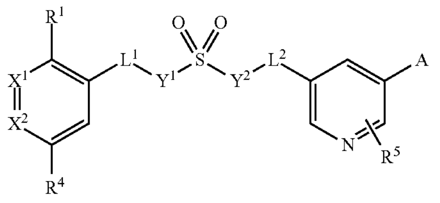

wherein:

$Y^1$ and $Y^2$ are independently a bond or —N($R^6$)—, wherein at least one of $Y^1$ and $Y^2$ is —N($R^6$)—;

$L^1$ and $L^2$ are independently a bond or optionally substituted alkylene;

$X^1$ is =N— or =C($R^2$)—;

$X^2$ is =N— or =C($R^3$)—;

$R^1$ and $R^4$ are independently selected from the group consisting of hydrogen, halogen, —CN, —C(O)—N($R^7$)—$R^8$, —C(O)—O—$R^9$, optionally substituted alkyl, optionally substituted cycloalkyl, optionally substituted heterocycloalkyl, optionally substituted alkoxy, haloalkyl, haloalkoxy, optionally substituted phenyl, and optionally substituted 5- or 6-membered heteroaryl;

$R^2$, $R^3$, and $R^5$ are independently selected from the group consisting of hydrogen, halogen, —CN, —C(O)—N($R^7$)—$R^8$, —C(O)—O—$R^9$, optionally substituted alkyl, optionally substituted cycloalkyl, optionally substituted heterocycloalkyl, optionally substituted alkoxy, haloalkyl, haloalkoxy, optionally substituted phenyl, and optionally substituted 5- or 6-membered heteroaryl;

$R^6$ is hydrogen, optionally substituted alkyl, optionally substituted alkenyl, or optionally substituted alkynyl;

$R^7$ and $R^8$ are independently hydrogen, optionally substituted alkyl, haloalkyl, optionally substituted cycloalkyl, optionally substituted heterocycloalkyl, optionally substituted phenyl, or $R^7$ and $R^8$ together with the nitrogen atom to which they are attached form an optionally substituted heterocycloamino;

$R^9$ is selected from the group consisting of hydrogen, optionally substituted alkyl, haloalkyl, optionally substituted cycloalkyl, optionally substituted heterocycloalkyl, and optionally substituted phenyl; and A is selected from the group consisting of —C(O)—N($R^7$)—$R^8$, —C(O)—O—$R^9$, optionally substituted phenyl, and optionally substituted 5- or 6-membered heteroaryl.

In some instances, the methods disclosed herein further comprise at least one of reducing plaque inflammation, reducing plaque calcification, reducing plaque size, reducing blood cholesterol, reducing serum lipid levels, inhibiting TNAP present in a liver, increasing plaque stability, or any combination thereof.

In some cases, the pharmaceutical composition is administered to a subject via a route selected from the group consisting of subcutaneous injection, intramuscular injection, and intravenous injection, or any combination thereof. In some cases, the pharmaceutical composition further comprises a delivery vehicle comprising at least one of liposomes, nanoparticles, microparticles, microspheres, lipid particles, vesicles, poloxamers, polycationic materials, or any combination thereof.

In some cases, the subject is diagnosed with an obesity-related condition. In some cases, the obesity-related condition is at least one of obesity-related insulin resistance or Type-2 diabetes.

In some instances, the methods disclosed herein further comprise administering the pharmaceutical composition in combination with a lipid-lowering agent. In some instances, the lipid-lowering agent is a statin. In some instances, the statin is at least one of lovastatin, pravastatin, simvastatin, atorvastatin, cerivastatin, fluvastatin, pravastatin, pitavastatin, rosuvastatin, or any combination thereof. In some instances, the methods disclosed herein further comprise measuring a biomarker in a biological sample obtained from an individual prior to administering the therapeutically effective amount of the TNAP inhibitor. In some cases, measuring the biomarker comprises assaying mRNA expression level of the biomarker. In some cases, measuring the biomarker comprises assaying protein level of the biomarker.

In some cases, the TNAP inhibitor is at least one of SBI-425, MLS-0038949, or a combination thereof. In some cases, the TNAP inhibitor is administered from 1 to 5 mg/kg/day. In some cases, the TNAP inhibitor is administered from 5 to 10 mg/kg/day. In some cases, the TNAP inhibitor is administered from 10 to 20 mg/kg/day. In some cases, the TNAP inhibitor is administered from 20 to 30 mg/kg/day. In some cases, the TNAP inhibitor is administered from 30 to 40 mg/kg/day. In some cases, the TNAP inhibitor is administered from 40 to 50 mg/kg/day. In some cases, the TNAP inhibitor is administered from 50 to 60 mg/kg/day. In some cases, the TNAP inhibitor is administered from 60 to 70 mg/kg/day. In some cases, the TNAP inhibitor is administered from 70 to 80 mg/kg/day. In some cases, the TNAP inhibitor is administered from 80 to 90 mg/kg/day. In some cases, the TNAP inhibitor is administered from 90 to 100 mg/kg/day.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

Some novel features of the methods and compositions disclosed herein are set forth in the present disclosure. A better understanding of the features and advantages of the methods and compositions disclosed herein will be obtained by reference to the following detailed description that sets forth illustrative embodiments, in which the principles of the disclosed compositions and methods are utilized, and the accompanying drawings of which:

FIGS. 3U and 3V illustrate serum levels of cholesterol (FIG. 3U) and triglycerides (TGs) (FIG. 3V). Results are shown as mean±standard deviation, and statistical analyses were performed with Mann-Whitney U test (A-C) and Student's t-test (FIGS. 3E-3V). CT: computed tomography; IHC: immunohistochemistry; OS: osteosense; PCR: polymerase chain reaction; PET: positron emission tomography SBI: SBI-425; SUVR: standardized uptake value ratio.

FIGS. 4B-4D illustrate quantification in the liver of ApoE-deficient mice of cholesterol levels (FIG. 4B), bile acid levels (FIG. 4C), TG levels (FIG. 4E).

Figure 1A:
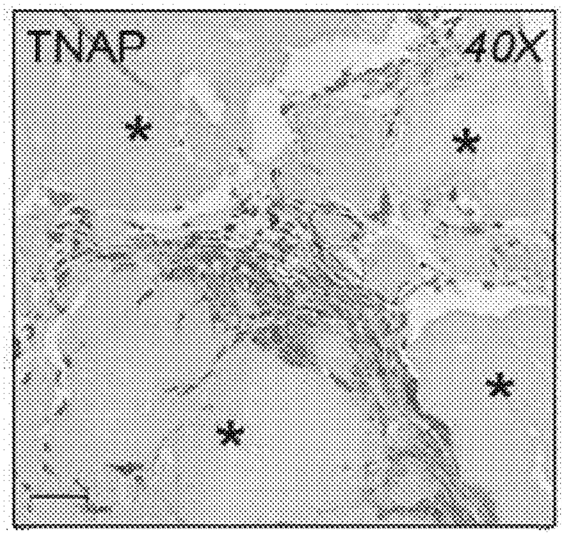
FIGS. 1A-1F illustrate representative immunohistochemistry staining of TNAP and RUNX2 in a human calcified carotid atherosclerotic plaque. Calcifications are indicated by *. On the central (FIGS. 1C and 1D), low-magnification (×2.5) photographs, the bar indicates 1 mm; on the high-magnification images (×40) (FIGS. 1A, 1B, 1C, and 1F), the bar indicates 50 μm.
Figure 1B:
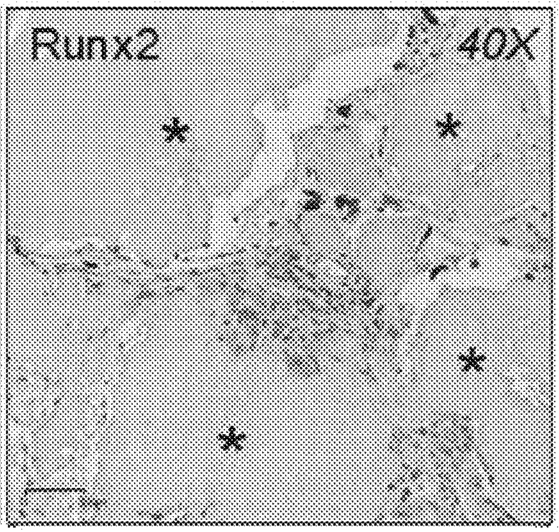
Figure 1C:
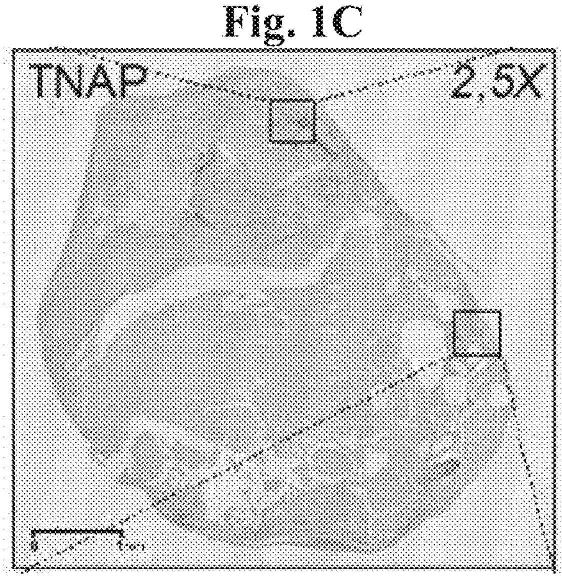
Figure 1D:
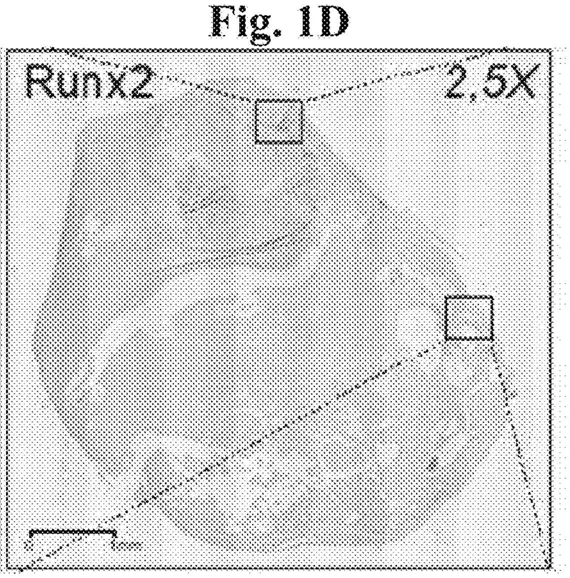
Figure 1E:
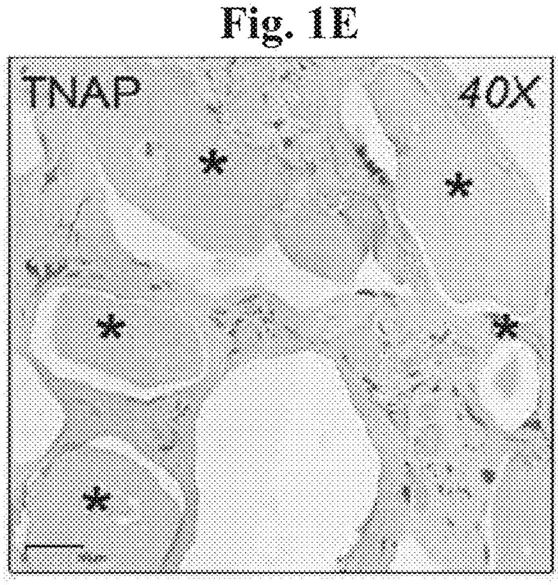
Figure 1F:
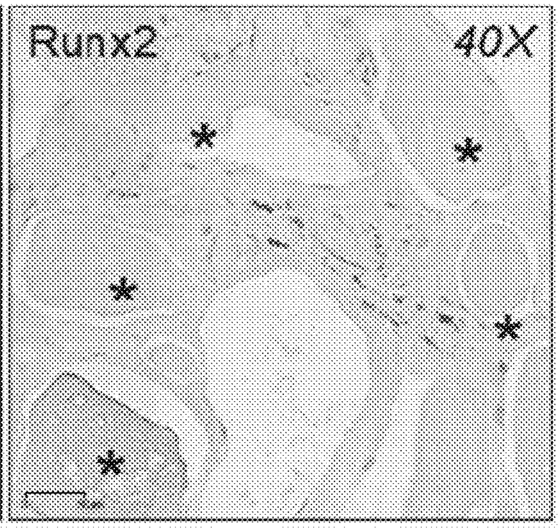

The novel features of the disclosure are set forth with particularity in the appended claims. A better understanding of the features and advantages of the present disclosure will be obtained by reference to the following detailed description that sets forth illustrative embodiments.

DETAILED DESCRIPTION

While various embodiments have been shown and described herein, it will be understood by those skilled in the art that such embodiments are provided by way of example only. Numerous variations, changes, and substitutions may occur to those skilled in the art without departing from the embodiments. It should be understood that various alternatives to the embodiments described herein may be employed.

While the vascular calcium score undoubtedly predicts cardiovascular mortality, the local impact of calcification on atherosclerotic plaque stability remains controversial. Tissue-nonspecific alkaline phosphatase (TNAP), the enzyme necessary for skeletal and dental mineralization, is strongly suspected to participate in vascular calcification. TNAP is expressed in atherosclerotic plaques and is also produced in the liver and released in the circulation at levels that correlate with metabolic syndrome and cardiovascular mortality. In this context, the instant application discloses the effect of a TNAP inhibitor on atherosclerotic plaque calcification and development.

Tissue-Nonspecific Alkaline Phosphatase (TNAP)

Tissue-Nonspecific Alkaline Phosphatase (TNAP) is the enzyme necessary for physiologic bone and tooth mineralization and may be responsible for plaque calcification. TNAP may be expressed under the control of the transcription factor RUNX2 in hypertrophic chondrocytes and osteoblasts, where it hydrolyzes the constitutive mineralization inhibitor inorganic pyrophosphate (PPi), to allow progression of mineralization onto the extracellular matrix. In Apolipoprotein (Apo) E-deficient mice, vascular smooth muscle cells (VSMCs) transdifferentiate into chondrocytes and express TNAP before calcification can be detected. Moreover, VSMC-specific deletion of RUNX2 in these mice, or in atherosclerotic mice deficient in low density lipoprotein receptor, strongly reduces calcification, further suggesting that TNAP is involved. In humans, where plaque calcification may not involve cartilage formation, and bone formation only in a minority of plaques, TNAP may stimulate plaque formation from the circulation. TNAP may be relatively ubiquitous; while predominantly expressed in the skeleton and teeth during physiologic mineralization, it may be also expressed in humans in the liver and released into the blood in amounts increasing with cholestasis and more generally with the development of metabolic syndrome (MetS). Since genetic deficiency in PPi generation resulting in reduced blood PPi leads to vascular calcification, increased serum TNAP in MetS may exacerbate plaque calcification from the blood.

Methods

In some aspects, disclosed herein are methods of reducing a number of microcalcifications in an atherosclerotic plaque. In some embodiments, the methods comprise administering a pharmaceutical composition comprising a therapeutically effective amount of a tissue-nonspecific alkaline phosphatase (TNAP) inhibitor. In some embodiments, administering the pharmaceutical composition comprising the therapeutically effective amount of the TNAP inhibitor reduces the number of microcalcifications in the atherosclerotic plaque.

In some aspects, disclosed herein are methods of preventing, arresting, or reducing the development of plaque calcifications in a patient in need thereof. In some embodiments, disclosed herein are methods of preventing the development of plaque calcifications in a patient in need thereof. In some embodiments, disclosed herein are methods of arresting the development of plaque calcifications in a patient in need thereof. In some embodiments, disclosed herein are methods of reducing the development of plaque calcifications in a patient in need thereof. In some embodiments, the methods comprise identifying a patient having atherosclerosis; and administering a pharmaceutical composition to the patient comprising a therapeutically effective amount of a tissue-nonspecific alkaline phosphatase (TNAP) inhibitor.

In some embodiments, administering the pharmaceutical composition comprising the therapeutically effective amount of the TNAP inhibitor prevents, arrests, or reduces the development of plaque calcifications.

In some aspects, disclosed herein are methods of treating atherosclerosis comprising administering a pharmaceutical composition to the patient comprising a therapeutically effective amount of a tissue-nonspecific alkaline phosphatase (TNAP) inhibitor.

In some aspects, a TNAP inhibitor disclosed herein is selected from the group consisting of a TNAP-targeting short hairpin RNA (shTNAP), a TNAP-targeting guide RNA (sgTNAP), and a small molecule. In some embodiments, the TNAP inhibitor is a shTNAP. In some embodiments, the TNAP inhibitor is a shTNAP, and the shTNAP is doxycycline-inducible. In some embodiments, the TNAP inhibitor is a sgTNAP. In some embodiments, the TNAP inhibitor is a small molecule. In some embodiments, the TNAP inhibitor is a combination of a a shTNAP and a sgTNAP. In some embodiments, the TNAP inhibitor is a combination of a shTNAP and a small molecule. In some embodiments, the TNAP inhibitor is a combination of a sgTNAP and a small molecule. In some embodiments, the TNAP inhibitor is a combination of a shTNAP, a sgTNAP, and a small molecule.

In some aspects, a TNAP inhibitor discloses herein is a small molecule.

In some embodiments, the small molecule disclosed herein is a compound or a pharmaceutically acceptable salt thereof of formula I as disclosed and described in WO2017/007943 (U.S. Pat. No. 9,920,068, U.S. application Ser. No. 15/314,887), or a compound, or a pharmaceutically acceptable salt thereof as disclosed and described in WO2017/007943.

In some embodiments, the small molecule disclosed herein is a compound or a pharmaceutically acceptable salt thereof of formula I as disclosed and described in WO2018/119444 (U.S. Pat. No. 11,046,710, U.S. application Ser. No. 16/472,109), or a compound, or a pharmaceutically acceptable salt thereof as disclosed and described in WO2018/119444.

In some embodiments, the small molecule disclosed herein is a compound of Formula I, or a pharmaceutically acceptable salt, polymorph, solvate, tautomer, metabolite, or N-oxide thereof:

(Formula I)

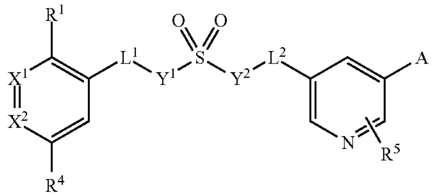

wherein:

- $Y^1$ and $Y^2$ are independently a bond or —N($R^6$)—, wherein at least one of $Y^1$ and $Y^2$ is —N($R^6$)—;
- $L^1$ and $L^2$ are independently a bond or optionally substituted alkylene;
- $X^1$ is =N— or =C($R^2$)—;
- $X^2$ is =N— or =C($R^3$)—;
- $R^1$ and $R^4$ are independently selected from the group consisting of hydrogen, halogen, —CN, —C(O)—N($R^7$)—$R^8$, —C(O)—O—$R^9$, optionally substituted alkyl, optionally substituted cycloalkyl, optionally substituted heterocycloalkyl, optionally substituted alkoxy, haloalkyl, haloalkoxy, optionally substituted phenyl, and optionally substituted 5- or 6-membered heteroaryl;
- $R^2$, $R^3$, and $R^5$ are independently selected from the group consisting of hydrogen, halogen, —CN, —C(O)—N($R^7$)—$R^8$, —C(O)—O—$R^9$, optionally substituted alkyl, optionally substituted cycloalkyl, optionally substituted heterocycloalkyl, optionally substituted alkoxy, haloalkyl, haloalkoxy, optionally substituted phenyl, and optionally substituted 5- or 6-membered heteroaryl;
- $R^6$ is hydrogen, optionally substituted alkyl, optionally substituted alkenyl, or optionally substituted alkynyl;
- $R^7$ and $R^8$ are independently hydrogen, optionally substituted alkyl, haloalkyl, optionally substituted cycloalkyl, optionally substituted heterocycloalkyl, optionally substituted phenyl, or $R^7$ and $R^8$ together with the nitrogen atom to which they are attached form an optionally substituted heterocycloamino;
- $R^9$ is selected from the group consisting of hydrogen, optionally substituted alkyl, haloalkyl, optionally substituted cycloalkyl, optionally substituted heterocycloalkyl, and optionally substituted phenyl; and
- A is selected from the group consisting of —C(O)—N($R^7$)—$R^8$, —C(O)—O—$R^9$, optionally substituted phenyl, and optionally substituted 5- or 6-membered heteroaryl.

In some embodiments, $Y^1$ and $Y^2$ are independently a bond or —N($R^6$)—, wherein at least one of $Y^1$ and $Y^2$ is —N($R^6$)—. In some embodiments, $Y^1$ is a bond or —N($R^6$)—. In some embodiments, $Y^1$ is a bond. In some embodiments, $Y^1$ is —N($R^6$)—. In some embodiments, $Y^2$ is a bond or —N($R^6$)—. In some embodiments, $Y^2$ is a bond. In some embodiments, $Y^2$ is —N($R^6$)—. In some embodiments, at least one of $Y^1$ and $Y^2$ is —N($R^6$)—.

In some embodiments, $L^1$ and $L^2$ are independently a bond or optionally substituted alkylene. In some embodiments, $L^1$ is a bond or optionally substituted alkylene. In some embodiments, $L^2$ is a bond or optionally substituted alkylene. In some embodiments, $X^1$ is =N— or =C($R^2$)—. In some embodiments, $X^1$ is =N—. In some embodiments, $X^1$ is =C($R^2$)—.

In some embodiments, $X^2$ is =N— or =C($R^3$)—. In some embodiments, $X^2$ is =N—. In some embodiments, $X^2$ is =C($R^3$)—.

In some embodiments, $R^1$ and $R^4$ are independently selected from the group consisting of hydrogen, halogen, —CN, —C(O)—N($R^7$)—$R^8$, —C(O)—O—$R^9$, optionally substituted alkyl, optionally substituted cycloalkyl, optionally substituted heterocycloalkyl, optionally substituted alkoxy, haloalkyl, haloalkoxy, optionally substituted phenyl, and optionally substituted 5- or 6-membered heteroaryl. In some embodiments, $R^1$ is selected from the group consisting of hydrogen, halogen, —CN, —C(O)—N($R^7$)—$R^8$, —C(O)—O—$R^9$, optionally substituted alkyl, optionally substituted cycloalkyl, optionally substituted heterocycloalkyl, optionally substituted alkoxy, haloalkyl, haloalkoxy, optionally substituted phenyl, and optionally substituted 5- or 6-membered heteroaryl. In some embodiments, $R^4$ is selected from the group consisting of hydrogen, halogen, —CN, —C(O)—N($R^7$)—$R^8$, —C(O)—O—$R^9$, optionally substituted alkyl, optionally substituted cycloalkyl, optionally substituted heterocycloalkyl, optionally substituted alkoxy, haloalkyl, haloalkoxy, optionally substituted phenyl, and optionally substituted 5- or 6-membered heteroaryl. In some embodiments, $R^1$ and $R^4$ are independently selected from the group consisting of hydrogen, halogen, —CN, alkyl, cycloalkyl, heterocycloalkyl, alkoxy, haloalkyl, haloalkoxy, phenyl, and 5- or 6-membered heteroaryl. In some embodiments, $R^1$ is selected from the group consisting of hydrogen, halogen, —CN, alkyl, cycloalkyl, heterocycloalkyl, alkoxy, haloalkyl, haloalkoxy, phenyl, and 5- or 6-membered heteroaryl. In some embodiments, $R^4$ is selected from the group consisting of hydrogen, halogen, —CN, alkyl, cycloalkyl, heterocycloalkyl, alkoxy, haloalkyl, haloalkoxy, phenyl, and 5- or 6-membered heteroaryl.

In some embodiments, $R^2$, $R^3$, and $R^5$ are independently selected from the group consisting of hydrogen, halogen, —CN, —C(O)—N($R^7$)—$R^8$, —C(O)—O—$R^9$, optionally substituted alkyl, optionally substituted cycloalkyl, optionally substituted heterocycloalkyl, optionally substituted alkoxy, haloalkyl, haloalkoxy, optionally substituted phenyl, and optionally substituted 5- or 6-membered heteroaryl. In some embodiments, $R^2$ is selected from the group consisting of hydrogen, halogen, —CN, —C(O)—N($R^7$)—$R^8$, —C(O)—O—$R^9$, optionally substituted alkyl, optionally substituted cycloalkyl, optionally substituted heterocycloalkyl, optionally substituted alkoxy, haloalkyl, haloalkoxy, optionally substituted phenyl, and optionally substituted 5- or 6-membered heteroaryl. In some embodiments, $R^3$ is selected from the group consisting of hydrogen, halogen, —CN, —C(O)—N($R^7$)—$R^8$, —C(O)—O—$R^9$, optionally substituted alkyl, optionally substituted cycloalkyl, optionally substituted heterocycloalkyl, optionally substituted alkoxy, haloalkyl, haloalkoxy, optionally substituted phenyl, and optionally substituted 5- or 6-membered heteroaryl. In some embodiments, $R^5$ is selected from the group consisting of hydrogen, halogen, —CN, —C(O)—N($R^7$)—$R^8$, —C(O)—O—$R^9$, optionally substituted alkyl, optionally substituted cycloalkyl, optionally substituted heterocycloalkyl, optionally substituted alkoxy, haloalkyl, haloalkoxy, optionally substituted phenyl, and optionally substituted 5- or 6-membered heteroaryl.

In some embodiments, $R^6$ is hydrogen, optionally substituted alkyl, optionally substituted alkenyl, or optionally substituted alkynyl. In some embodiments, $R^6$ is hydrogen. In some embodiments, $R^6$ is optionally substituted alkyl. In some embodiments, $R^6$ is optionally substituted alkenyl. In some embodiments, $R^6$ is optionally substituted alkynyl.

In some embodiments, $R^7$ and $R^8$ are independently hydrogen, optionally substituted alkyl, haloalkyl, optionally substituted cycloalkyl, optionally substituted heterocycloalkyl, optionally substituted phenyl, or $R^7$ and $R^8$ together with the nitrogen atom to which they are attached form an optionally substituted heterocycloamino. In some embodiments, $R^7$ is hydrogen, optionally substituted alkyl, haloalkyl, optionally substituted cycloalkyl, optionally substituted heterocycloalkyl, optionally substituted phenyl, or $R^7$ and $R^8$ together with the nitrogen atom to which they are attached form an optionally substituted heterocycloamino. In some embodiments, $R^8$ is hydrogen, optionally substituted alkyl, haloalkyl, optionally substituted cycloalkyl, optionally substituted heterocycloalkyl, optionally substituted phenyl, or $R^7$ and $R^8$ together with the nitrogen atom to which they are attached form an optionally substituted heterocycloamino.

In some embodiments, $R^9$ is selected from the group consisting of hydrogen, optionally substituted alkyl, haloalkyl, optionally substituted cycloalkyl, optionally substituted heterocycloalkyl, and optionally substituted phenyl. In some embodiments, $R^9$ is hydrogen. In some embodiments, $R^9$ is optionally substituted alkyl. In some embodiments, $R^9$ is haloalkyl. In some embodiments, $R^9$ is optionally substituted cycloalkyl. In some embodiments, $R^9$ is optionally substituted heterocycloalkyl. In some embodiments, $R^9$ is optionally substituted phenyl.

In some embodiments, A is selected from the group consisting of —C(O)—N($R^7$)—$R^8$, —C(O)—O—$R^9$, optionally substituted phenyl, and optionally substituted 5- or 6-membered heteroaryl. In some embodiments, A is —C(O)—N($R^7$)—$R^8$. In some embodiments, A is —C(O)—O—$R^9$. In some embodiments, A is—optionally substituted phenyl. In some embodiments, A is optionally substituted 5- or 6-membered heteroaryl.

Any combination of the groups described above for the various variables is contemplated herein. Throughout the specification, groups and substituents thereof are chosen by one skilled in the field to provide stable moieties and compounds.

In some embodiments, the methods disclosed herein further comprise reducing plaque inflammation, reducing plaque calcification, reducing plaque size, reducing blood cholesterol, reducing serum lipid levels, inhibiting TNAP present in a liver, increasing plaque stability, and combinations thereof. In some embodiments, the methods disclosed herein further comprise reducing plaque inflammation. In some embodiments, the methods disclosed herein further comprise reducing plaque calcification. In some embodiments, the methods disclosed herein further comprise reducing plaque size. In some embodiments, the methods disclosed herein further comprise reducing blood cholesterol. In some embodiments, the methods disclosed herein further comprise reducing serum lipid levels. In some embodiments, the methods disclosed herein further comprise inhibiting TNAP present in a liver. In some embodiments, the methods disclosed herein further comprise increasing plaque stability.

In some aspects, in the methods disclosed herein, the pharmaceutical composition disclosed herein is administered to a subject via a route selected from the group consisting of subcutaneous injection, intramuscular injection, and intravenous injection. In some embodiments, in the methods disclosed herein, the pharmaceutical composition disclosed herein is administered to a subject via subcutaneous injection. In some embodiments, in the methods disclosed herein, the pharmaceutical composition disclosed herein is administered to a subject via intramuscular injection. In some embodiments, in the methods disclosed herein, the pharmaceutical composition disclosed herein is administered to a subject via intravenous injection.

In some aspects, in the methods disclosed herein, the pharmaceutical composition disclosed herein further comprises a delivery vehicle selected from the group consisting of liposomes, nanoparticles, microparticles, microspheres, lipid particles, vesicles, poloxamers, and polycationic materials. In some embodiments, in the methods disclosed herein, the pharmaceutical composition disclosed herein further comprises liposomes as a delivery vehicle. In some embodiments, in the methods disclosed herein, the pharmaceutical composition disclosed herein further comprises nanoparticles as a delivery vehicle. In some embodiments, in the methods disclosed herein, the pharmaceutical composition disclosed herein further comprises microparticles as a delivery vehicle. In some embodiments, in the methods disclosed herein, the pharmaceutical composition disclosed herein further comprises microspheres as a delivery vehicle. In some embodiments, in the methods disclosed herein, the pharmaceutical composition disclosed herein further comprises lipid particles as a delivery vehicle. In some embodiments, in the methods disclosed herein, the pharmaceutical composition disclosed herein further comprises vesicles as a delivery vehicle. In some embodiments, in the methods disclosed herein, the pharmaceutical composition disclosed herein further comprises poloxamers as a delivery vehicle. In some embodiments, in the methods disclosed herein, the pharmaceutical composition disclosed herein further comprises polycationic materials as a delivery vehicle.

In some aspects, the subject disclosed herein has been diagnosed with an obesity-related condition. In some embodiments, the obesity-related condition is obesity-related insulin resistance diabetes. In some embodiments, the obesity-related condition is Type-2 diabetes.

In some aspects, the methods disclosed herein comprise administering the pharmaceutical composition disclosed herein in combination with a lipid-lowering agent. In some embodiments, the lipid-lowering agent is a statin. In some embodiments, the statin is selected from the group consisting of lovastatin, pravastatin, simvastatin, atorvastatin, cerivastatin, fluvastatin, pravastatin, pitavastatin, and rosuvastatin. In some embodiments, the statin is lovastatin. In some embodiments, the statin is pravastatin. In some embodiments, the statin is simvastatin. In some embodiments, the statin is atorvastatin. In some embodiments, the statin is cerivastatin. In some embodiments, the statin is fluvastatin. In some embodiments, the statin is pravastatin. In some embodiments, the statin is pitavastatin. In some embodiments, the statin is rosuvastatin.

In some aspects, the methods disclosed herein further comprise measuring a biomarker in a biological sample obtained from the individual prior to administering the therapeutically effective amount of the TNAP inhibitor. In some embodiments, measuring the biomarker comprises assaying mRNA expression level of the biomarker. In some embodiments, measuring the biomarker comprises assaying protein level of the biomarker.

Compounds

In some aspects, TNAP inhibitors discloses herein are a small molecule.

In some embodiments, the small molecule disclosed herein is a compound or a pharmaceutically acceptable salt thereof of formula I as disclosed and described in WO2017/007943, or a compound, or a pharmaceutically acceptable salt thereof as disclosed and described in WO2017/007943.

In some embodiments, the small molecule disclosed herein is a compound or a pharmaceutically acceptable salt thereof of formula I as disclosed and described in WO2018/119444, or a compound, or a pharmaceutically acceptable salt thereof as disclosed and described in WO2018/119444.

In some embodiments, the small molecule disclosed herein is a compound of Formula I, or a pharmaceutically acceptable salt, polymorph, solvate, tautomer, metabolite, or N-oxide thereof:

(Formula I)

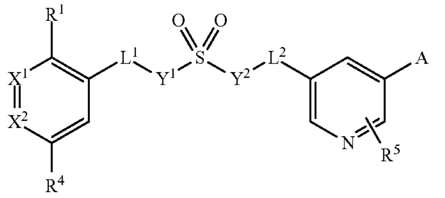

wherein:

$Y^1$ and $Y^2$ are independently a bond or —N($R^6$)—, wherein at least one of $Y^1$ and $Y^2$ is —N($R^6$)—;

$L^1$ and $L^2$ are independently a bond or optionally substituted alkylene;

$X^1$ is =N— or =C($R^2$)—;

$X^2$ is =N— or =C($R^3$)—;

$R^1$ and $R^4$ are independently selected from the group consisting of hydrogen, halogen, —CN, —C(O)—N($R^7$)—$R^8$, —C(O)—O—$R^9$, optionally substituted alkyl, optionally substituted cycloalkyl, optionally substituted heterocycloalkyl, optionally substituted alkoxy, haloalkyl, haloalkoxy, optionally substituted phenyl, and optionally substituted 5- or 6-membered heteroaryl;

$R^2$, $R^3$, and $R^5$ are independently selected from the group consisting of hydrogen, halogen, —CN, —C(O)—N($R^7$)—$R^8$, —C(O)—O—$R^9$, optionally substituted alkyl, optionally substituted cycloalkyl, optionally substituted heterocycloalkyl, optionally substituted alkoxy, haloalkyl, haloalkoxy, optionally substituted phenyl, and optionally substituted 5- or 6-membered heteroaryl;

$R^6$ is hydrogen, optionally substituted alkyl, optionally substituted alkenyl, or optionally substituted alkynyl;

$R^7$ and $R^8$ are independently hydrogen, optionally substituted alkyl, haloalkyl, optionally substituted cycloalkyl, optionally substituted heterocycloalkyl, optionally substituted phenyl, or $R^7$ and $R^8$ together with the nitrogen atom to which they are attached form an optionally substituted heterocycloamino;

$R^9$ is selected from the group consisting of hydrogen, optionally substituted alkyl, haloalkyl, optionally substituted cycloalkyl, optionally substituted heterocycloalkyl, and optionally substituted phenyl; and A is selected from the group consisting of —C(O)—N($R^7$)—$R^8$, —C(O)—O—$R^9$, optionally substituted phenyl, and optionally substituted 5- or 6-membered heteroaryl.

In some embodiments, $Y^1$ and $Y^2$ are independently a bond or —N($R^6$)—, wherein at least one of $Y^1$ and $Y^2$ is —N($R^6$)—. In some embodiments, $Y^1$ is a bond or —N($R^6$)—. In some embodiments, $Y^1$ is a bond. In some embodiments, $Y^1$ is —N($R^6$)—. In some embodiments, $Y^2$ is a bond or —N($R^6$)—. In some embodiments, $Y^2$ is a bond. In some embodiments, $Y^2$ is —N($R^6$)—. In some embodiments, at least one of $Y^1$ and $Y^2$ is —N($R^6$)—.

In some embodiments, $L^1$ and $L^2$ are independently a bond or optionally substituted alkylene. In some embodiments, L' is a bond or optionally substituted alkylene. In some embodiments, $L^2$ is a bond or optionally substituted alkylene. In some embodiments, $X^1$ is =N— or =C($R^2$)—. In some embodiments, $X^1$ is =N—. In some embodiments, $X^1$ is =C($R^2$)—.

In some embodiments, $X^2$ is =N— or =C($R^3$)—. In some embodiments, $X^2$ is =N—. In some embodiments, $X^2$ is =C($R^3$)—.

In some embodiments, $R^1$ and $R^4$ are independently selected from the group consisting of hydrogen, halogen, —CN, —C(O)—N($R^7$)—$R^8$, —C(O)—O—$R^9$, optionally substituted alkyl, optionally substituted cycloalkyl, optionally substituted heterocycloalkyl, optionally substituted alkoxy, haloalkyl, haloalkoxy, optionally substituted phenyl, and optionally substituted 5- or 6-membered heteroaryl. In some embodiments, $R^1$ is selected from the group consisting of hydrogen, halogen, —CN, —C(O)—N($R^7$)—$R^8$, —C(O)—O—$R^9$, optionally substituted alkyl, optionally substituted cycloalkyl, optionally substituted heterocycloalkyl, optionally substituted alkoxy, haloalkyl, haloalkoxy, optionally substituted phenyl, and optionally substituted 5- or 6-membered heteroaryl. In some embodiments, $R^4$ is selected from the group consisting of hydrogen, halogen, —CN, —C(O)—N($R^7$)—$R^8$, —C(O)—O—$R^9$, optionally substituted alkyl, optionally substituted cycloalkyl, optionally substituted heterocycloalkyl, optionally substituted alkoxy, haloalkyl, haloalkoxy, optionally substituted phenyl, and optionally substituted 5- or 6-membered heteroaryl.

In some embodiments, $R^2$, $R^3$, and $R^5$ are independently selected from the group consisting of hydrogen, halogen, —CN, —C(O)—N($R^7$)—$R^8$, —C(O)—O—$R^9$, optionally substituted alkyl, optionally substituted cycloalkyl, optionally substituted heterocycloalkyl, optionally substituted alkoxy, haloalkyl, haloalkoxy, optionally substituted phenyl, and optionally substituted 5- or 6-membered heteroaryl. In some embodiments, $R^2$ is selected from the group consisting of hydrogen, halogen, —CN, —C(O)—N($R^7$)—$R^8$, —C(O)—O—$R^9$, optionally substituted alkyl, optionally substituted cycloalkyl, optionally substituted heterocycloalkyl, optionally substituted alkoxy, haloalkyl, haloalkoxy, optionally substituted phenyl, and optionally substituted 5- or 6-membered heteroaryl. In some embodiments, $R^3$ is selected from the group consisting of hydrogen, halogen, —CN, —C(O)—N($R^7$)—$R^8$, —C(O)—O—$R^9$, optionally substituted alkyl, optionally substituted cycloalkyl, optionally substituted heterocycloalkyl, optionally substituted alkoxy, haloalkyl, haloalkoxy, optionally substituted phenyl, and optionally substituted 5- or 6-membered heteroaryl. In some embodiments, $R^5$ is selected from the group consisting of hydrogen, halogen, —CN, —C(O)—N($R^7$)—$R^8$, —C(O)—O—$R^9$, optionally substituted alkyl, optionally substituted cycloalkyl, optionally substituted heterocycloalkyl, optionally substituted alkoxy, haloalkyl, haloalkoxy, optionally substituted phenyl, and optionally substituted 5- or 6-membered heteroaryl.

In some embodiments, $R^6$ is hydrogen, optionally substituted alkyl, optionally substituted alkenyl, or optionally substituted alkynyl. In some embodiments, $R^6$ is hydrogen. In some embodiments, $R^6$ is optionally substituted alkyl. In some embodiments, $R^6$ is optionally substituted alkenyl. In some embodiments, $R^6$ is optionally substituted alkynyl.

In some embodiments, $R^7$ and $R^8$ are independently hydrogen, optionally substituted alkyl, haloalkyl, optionally substituted cycloalkyl, optionally substituted heterocycloalkyl, optionally substituted phenyl, or $R^7$ and $R^8$ together with the nitrogen atom to which they are attached form an optionally substituted heterocycloamino. In some embodiments, $R^7$ is hydrogen, optionally substituted alkyl, haloalkyl, optionally substituted cycloalkyl, optionally substituted heterocycloalkyl, optionally substituted phenyl, or $R^7$ and $R^8$ together with the nitrogen atom to which they are attached form an optionally substituted heterocycloamino. In some embodiments, $R^8$ is hydrogen, optionally substituted alkyl, haloalkyl, optionally substituted cycloalkyl, optionally substituted heterocycloalkyl, optionally substituted phenyl, or $R^7$ and $R^8$ together with the nitrogen atom to which they are attached form an optionally substituted heterocycloamino.

In some embodiments, $R^9$ is selected from the group consisting of hydrogen, optionally substituted alkyl, haloalkyl, optionally substituted cycloalkyl, optionally substituted heterocycloalkyl, and optionally substituted phenyl. In some embodiments, $R^9$ is hydrogen. In some embodiments, $R^9$ is optionally substituted alkyl. In some embodiments, $R^9$ is haloalkyl. In some embodiments, $R^9$ is optionally substituted cycloalkyl. In some embodiments, $R^9$ is optionally substituted heterocycloalkyl. In some embodiments, $R^9$ is optionally substituted phenyl.

In some embodiments, A is selected from the group consisting of —C(O)—N($R^7$)—$R^8$, —C(O)—O—$R^9$, optionally substituted phenyl, and optionally substituted 5- or 6-membered heteroaryl. In some embodiments, A is —C(O)—N($R^7$)—$R^8$. In some embodiments, A is —C(O)—O—$R^9$. In some embodiments, A is optionally substituted phenyl. In some embodiments, A is optionally substituted 5- or 6-membered heteroaryl.

In some embodiments, the small molecule disclosed herein is a compound of Formula I, or a pharmaceutically acceptable salt thereof, wherein the small molecule is selected from Table 1.

TABLE 1

Examples of Small Molecule as a TNAP Inhibitor

| Compound | Structure |
|---|---|
| SBI-425 | 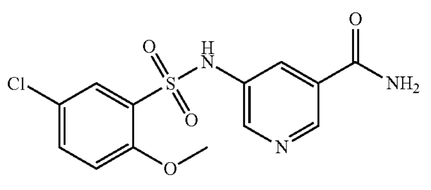 [SMILES: COc1ccc(Cl)cc1S(=O)(=O)Nc1cncc(C(N)=O)c1] |
| MLS-0038949 | 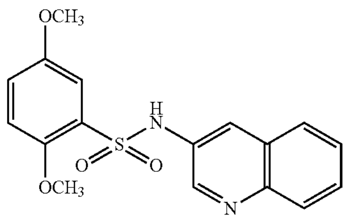 [SMILES: COc1ccc(OC)c(S(=O)(=O)Nc2cnc3ccccc3c2)c1] |

Any combination of the groups described above for the various variables is contemplated herein. Throughout the specification, groups and substituents thereof are chosen by one skilled in the field to provide stable moieties and compounds.

Further Forms of Small Molecules Disclosed Herein

Labeled Compounds

In some embodiments, the compounds described herein exist in their isotopically-labeled forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. Thus, in some embodiments, the compounds disclosed herein include isotopically-labeled compounds, which are identical to those recited herein, but for the fact that one or more atoms are replaced by an atom having an atomic mass or mass number different from the atomic mass or mass number usually found in nature. Examples of isotopes that can be incorporated into compounds disclosed herein include isotopes of hydrogen, carbon, nitrogen, oxygen, phosphorous, sulfur, fluorine and chloride, such as $^{2}H$ (D), $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds described herein, and the pharmaceutically acceptable salts, solvates, or stereoisomers thereof which contain the aforementioned isotopes and/or other isotopes of other atoms are within the scope of this disclosure. Certain isotopically-labeled compounds, for example those into which radioactive isotopes such as $^{3}H$ and $^{14}C$ are incorporated, are useful in drug and/or substrate tissue distribution assays. Tritiated, i.e., $^{3}H$ and carbon-14, i.e., $^{14}C$, isotopes are particularly preferred for their ease of preparation and detectability.

In some embodiments, the abundance of deuterium in each of the substituents disclosed herein is independently at least 1%, at least 10%, at least 20%, at least 30%, at least 40%, at least 50%, at least 60%, at least 70%, at least 80%, at least 90%, or 100% of a total number of hydrogen and deuterium. In some embodiments, one or more of the substituents disclosed herein comprise deuterium at a percentage higher than the natural abundance of deuterium. In some embodiments, one or more hydrogens are replaced with one or more deuteriums in one or more of the substituents disclosed herein.

In some embodiments of a compound disclosed herein, one or more of $R^1$, $R^2$, $R^3$, $R^4$, $R^5$, $R^6$, $R^7$, $R^8$, and $R^9$ groups comprise deuterium at a percentage higher than the natural abundance of deuterium.

In some embodiments of a compound disclosed herein, one or more hydrogens are replaced with one or more deuteriums in one or more of the following groups $R^1$, $R^2$, $R^3$, $R^4$, $R^5$, $R^6$, $R^7$, $R^8$, and $R^9$.

In some embodiments of a compound disclosed herein, the abundance of deuterium in one or more of $R^1$, $R^2$, $R^3$, $R^4$, $R^5$, $R^6$, $R^7$, $R^8$, and $R^9$ is independently at least 70%, at least 80%, at least 90%, or 100% of a total number of hydrogen and deuterium.

In some embodiments, the compounds described herein are labeled by other means, including, but not limited to, the use of chromophores or fluorescent moieties, bioluminescent labels, or chemiluminescent labels.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

Solvates

In some embodiments, the compounds described herein exist as solvates. The disclosure provides for methods of treating diseases by administering such solvates. The disclosure further provides for methods of treating diseases by administering such solvates as pharmaceutical compositions.

Pharmaceutical Composition

In some aspects, disclosed herein are pharmaceutical compositions comprising a therapeutically effective amount of a tissue-nonspecific alkaline phosphatase (TNAP) inhibitor. In some embodiments, administering the pharmaceutical composition comprising the therapeutically effective amount of the TNAP inhibitor reduces the number of microcalcifications in the atherosclerotic plaque. In some embodiments, administering the pharmaceutical composition comprising the therapeutically effective amount of the TNAP inhibitor prevents, arrests, or reduces the development of plaque calcifications. In some embodiments, administering the pharmaceutical composition to the patient comprising a therapeutically effective amount of a tissue-nonspecific alkaline phosphatase (TNAP) inhibitor treats atherosclerosis.

In some aspects, the pharmaceutical compositions disclosed herein can be administered to a subject via a route selected from the group consisting of subcutaneous injection, intramuscular injection, and intravenous injection. In some embodiments, the pharmaceutical composition disclosed herein can be administered to a subject via subcutaneous injection. In some embodiments, the pharmaceutical composition disclosed herein can be administered to a subject via intramuscular injection. In some embodiments, the pharmaceutical composition disclosed herein can be administered to a subject via intravenous injection.

In some embodiments, the pharmaceutical compositions disclosed herein further comprise a delivery vehicle selected from the group consisting of liposomes, nanoparticles, microparticles, microspheres, lipid particles, vesicles, poloxamers, and polycationic materials. In some embodiments, the pharmaceutical compositions disclosed herein further comprise liposomes as a delivery vehicle. In some embodiments, the pharmaceutical compositions disclosed herein further comprise nanoparticles as a delivery vehicle. In some embodiments, the pharmaceutical compositions disclosed herein further comprise microparticles as a delivery vehicle. In some embodiments, the pharmaceutical compositions disclosed herein further comprise microspheres as a delivery vehicle. In some embodiments, the pharmaceutical compositions disclosed herein further comprise lipid particles as a delivery vehicle. In some embodiments, the pharmaceutical compositions disclosed herein further comprise vesicles as a delivery vehicle. In some embodiments, the pharmaceutical compositions disclosed herein further comprise poloxamers as a delivery vehicle. In some embodiments, the pharmaceutical compositions disclosed herein further comprise polycationic materials as a delivery vehicle.

Definitions

Unless defined otherwise, all terms of art, notations, and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

Throughout this application, various embodiments can be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

As used herein, the singular forms "a," "an," and "the" are intended to include the plural forms as well, unless the context clearly indicates otherwise. For example, the term "a sample" includes a plurality of samples, including mixtures thereof. Furthermore, to the extent that the terms "including," "includes," "having," "has," "with," or variants thereof are used in either the detailed description and/or the claims, such terms are intended to be inclusive in a manner similar to the term "comprising."

The terms "measuring" and "assaying" are often used interchangeably herein to refer to forms of measurement. The terms include determining if an element is present or not (for example, detection). These terms can include quantitative, qualitative, or quantitative and qualitative determinations.

The section headings used herein are for organizational purposes only and are not to be construed as limiting the subject matter described.

Any methods described herein are modular. Accordingly, terms such as "first" and "second" do not necessarily imply priority, order of importance, or order of acts.

Use of absolute or sequential terms, for example, "first," "initially," "subsequently," "before," "after," and "finally," are not meant to limit scope of the present embodiments disclosed herein but as exemplary.

As used herein, the phrases "at least one," "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

The terms "subject," "individual," or "patient" are often used interchangeably herein. A "subject" can be a biological entity containing expressed genetic materials. The biological entity can be a plant, animal, or microorganism, including, for example, bacteria, viruses, fungi, and protozoa. The subject can be tissues, cells and their progeny of a biological entity obtained in vivo or cultured in vitro. The subject can be a mammal. The mammal can be a human. The subject can be diagnosed or suspected of being at high risk for a disease. In some cases, the subject is not necessarily diagnosed or suspected of being at high risk for the disease.

As used herein, the term "in vivo" can be used to describe an event that takes place in an organism, such as a subject's body.

As used herein, the term "ex vivo" can be used to describe an event that takes place outside of an organism such as subject's body. An "ex vivo" assay cannot be performed on a subject. Rather, it can be performed upon a sample separate from a subject. Ex vivo can be used to describe an event occurring in an intact cell outside a subject's body.

As used herein, the term "in vitro" can be used to describe an event that takes places contained in a container for holding laboratory reagent such that it is separated from the living biological source organism from which the material is obtained. In vitro assays can encompass cell-based assays in which cells alive or dead are employed. In vitro assays can also encompass a cell-free assay in which no intact cells are employed.

As used herein, the term "about" a number refers to that number plus or minus 10% of that number. The term "about" a range refers to that range minus 10% of its lowest value and plus 10% of its greatest value.

As used herein, the terms "treatment" or "treating" are used in reference to a pharmaceutical or other intervention regimen for obtaining beneficial or desired results in the recipient. Beneficial or desired results include but are not limited to a therapeutic benefit and/or a prophylactic benefit. A therapeutic benefit can refer to eradication or amelioration of symptoms or of an underlying disorder being treated. Also, a therapeutic benefit can be achieved with the eradication or amelioration of one or more of the physiological symptoms associated with the underlying disorder such that an improvement is observed in the subject, notwithstanding that the subject can still be afflicted with the underlying disorder. A prophylactic effect includes delaying, preventing, or eliminating the appearance of a disease or condition, delaying or eliminating the onset of symptoms of a disease or condition, slowing, halting, or reversing the progression of a disease or condition, or any combination thereof. For prophylactic benefit, a subject at risk of developing a particular disease, or to a subject reporting one or more of the physiological symptoms of a disease can undergo treatment, even though a diagnosis of this disease may not have been made.

The terms "increased," "increasing," or "increase" are used herein to generally mean an increase by a statically significant amount. In some aspects, the terms "increased," or "increase," mean an increase of at least 10% as compared to a reference level, for example an increase of at least about 10%, at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, standard, or control. Other examples of "increase" include an increase of at least 2-fold, at least 5-fold, at least 10-fold, at least 20-fold, at least 50-fold, at least 100-fold, at least 1000-fold or more as compared to a reference level.

The terms "decreased," "decreasing," or "decrease" are used herein generally to mean a decrease by a statistically significant amount. In some aspects, "decreased" or "decrease" means a reduction by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g., absent level or non-detectable level as compared to a reference level), or any decrease between 10-100% as compared to a reference level. In the context of a marker or symptom, by these terms is meant a statistically significant decrease in such level. The decrease can be, for example, at least 10%, at least 20%, at least 30%, at least 40% or more, and is preferably down to a level accepted as within the range of normal for an individual without a given disease. Other examples of "decrease" include a decrease of at least 2-fold, at least 5-fold, at least 10-fold, at least 20-fold, at least 50-fold, at least 100-fold, at least 1000-fold or more as compared to a reference level.

The terms "individual" or "subject" are used interchangeably and encompass mammals. Non-limiting examples of mammal include any member of the mammalian class: humans, non-human primates such as chimpanzees, and other apes and monkey species; farm animals such as cattle, horses, sheep, goats, swine; domestic animals such as rabbits, dogs, and cats; laboratory animals including rodents such as rats, mice and guinea pigs, and the like. The mammal can be a human. The term "animal" as used herein comprises human beings and non-human animals. In one embodiment, a "non-human animal" is a mammal, for example a rodent such as rat or a mouse. A "patient," as used herein refers to a subject that has, or has been diagnosed with, a disease or a condition described herein.

"Treat, "treating," or "treatment," as used herein, refers to alleviating or abrogating a disorder, disease, or condition; or one or more of the symptoms associated with the disorder, disease, or condition; or alleviating or eradicating a cause of the disorder, disease, or condition itself. Desirable effects of treatment can include, but are not limited to, preventing occurrence or recurrence of disease, alleviation of symptoms, diminishing any direct or indirect pathological consequences of the disease, preventing metastasis, decreasing the rate of disease progression, amelioration or palliation of the disease state and remission or improved prognosis.

"Treatment" of an individual (e.g., a mammal, such as a human) or a cell is any type of intervention used in an attempt to alter the natural course of the individual or cell. In some embodiments, treatment includes administration of a pharmaceutical composition, subsequent to the initiation of a pathologic event or contact with an etiologic agent and includes stabilization of the condition (e.g., condition does not worsen) or alleviation of the condition.

An "effective amount" or "therapeutically effective amount" refers to an amount of a compound administered to a mammalian subject, either as a single dose or as part of a series of doses, which is effective to produce a desired therapeutic effect.

The term "pharmaceutically acceptable carrier," "pharmaceutically acceptable excipient," "physiologically acceptable carrier," or "physiologically acceptable excipient" refers to a pharmaceutically acceptable material, composition, or vehicle such as a liquid or solid filler, diluent, excipient, solvent, or encapsulating material. A component can be "pharmaceutically acceptable" in the sense of being compatible with the other ingredients of a pharmaceutical formulation. It can also be suitable for use in contact with the tissue or organ of humans and animals without excessive toxicity, irritation, allergic response, immunogenicity, or other problems or complications, commensurate with a reasonable benefit/risk ratio.

As used herein, the term "administration," "administering" and variants thereof means introducing a composition or agent into a subject and includes concurrent and sequential introduction of a composition or agent. The introduction of a composition or agent into a subject is by any suitable route, including orally, pulmonarily, intranasally, parenterally (intravenously, intramuscularly, intraperitoneally, or subcutaneously), rectally, intralymphatically, or topically. Administration includes self-administration and administration by another. A suitable route of administration allows the composition or the agent to perform its intended function. For example, if a suitable route is intravenous, the composition is administered by introducing the composition or agent into a vein of the subject. Administration can be carried out by any suitable route. In some embodiments, the administering is intravenous administration. In some embodiments, the administering is pulmonary administration. In some embodiments, the administering is inhalation.

The term "pharmaceutical formulation" refers to a mixture of a composition disclosed herein with other chemical components such as diluents or carriers (e.g., pharmaceutically acceptable inactive ingredients) such as carriers, excipients, binders, filling agents, suspending agents, flavoring agents, sweetening agents, disintegrating agents, dispersing agents, surfactants, lubricants, colorants, diluents, solubilizers, moistening agents, plasticizers, stabilizers, penetration enhancers, wetting agents, anti-foaming agents, antioxidants, preservatives, or one or more combination thereof. The pharmaceutical formulation can facilitate administration of the composition to an organism. Multiple techniques of administering a compound exist in the art including, but not limited to, oral, injection, aerosol, parenteral, and topical administration.

The terms below, as used herein, have the following meanings, unless indicated otherwise:

"oxo" refers to =O.

"Carboxyl" refers to —COOH.

"Alkyl" refers to a straight-chain or branched-chain saturated hydrocarbon monoradical having from one to about ten carbon atoms, more preferably one to six carbon atoms. Examples include, but are not limited to methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, sec-butyl, t-butyl, n-pentyl, isopentyl, neopentyl, tert-amyl and hexyl, and longer alkyl groups, such as heptyl, octyl and the like. Whenever it appears herein, a numerical range such as "$C_1$-$C_6$ alkyl" or "$C_{1-6}$alkyl", means that the alkyl group can consist of 1 carbon atom, 2 carbon atoms, 3 carbon atoms, 4 carbon atoms, 5 carbon atoms or 6 carbon atoms, although the present definition also covers the occurrence of the term "alkyl" where no numerical range is designated. In some embodiments, the alkyl is a $C_{1-10}$alkyl. In some embodiments, the alkyl is a $C_{1-6}$alkyl. In some embodiments, the alkyl is a $C_{1-5}$alkyl. In some embodiments, the alkyl is a $C_{1-4}$alkyl. In some embodiments, the alkyl is a $C_{1-3}$alkyl. Unless stated otherwise specifically in the specification, an alkyl group can be optionally substituted, for example, with oxo, halogen, amino, —CN, nitro, hydroxyl, haloalkyl, alkoxy, carboxyl, carboxylate, aryl, cycloalkyl, heterocycloalkyl, heteroaryl, and the like. In some embodiments, the alkyl is optionally substituted with oxo, halogen, —CN, —COOH, —$COOCH_3$, —OH, —$OCH_3$, —$NH_2$, or —$NO_2$. In some embodiments, the alkyl is optionally substituted with halogen, —CN, —OH, or —$OCH_3$. In some embodiments, the alkyl is optionally substituted with halogen.

"Alkenyl" refers to a straight-chain or branched-chain hydrocarbon monoradical having one or more carbon-carbon double-bonds and having from two to about ten carbon atoms, more preferably two to about six carbon atoms. The group can be in either the cis or trans conformation about the double bond(s) and should be understood to include both isomers. Examples include, but are not limited to ethenyl ($—CH═CH_2$), 1-propenyl ($—CH_2CH═CH_2$), isopropenyl ($—C(CH_3)═CH_2$), butenyl, 1,3-butadienyl and the like. Whenever it appears herein, a numerical range such as "$C_2$-$C_6$ alkenyl" or "$C_{2-6}$alkenyl", means that the alkenyl group can consist of 2 carbon atoms, 3 carbon atoms, 4 carbon atoms, 5 carbon atoms or 6 carbon atoms, although the present definition also covers the occurrence of the term "alkenyl" where no numerical range is designated. Unless stated otherwise specifically in the specification, an alkenyl group can be optionally substituted, for example, with oxo, halogen, amino, —CN, nitro, hydroxyl, haloalkyl, alkoxy, carboxyl, carboxylate, aryl, cycloalkyl, heterocycloalkyl, heteroaryl, and the like. In some embodiments, the alkenyl is optionally substituted with oxo, halogen, —CN, —COOH, $—COOCH_3$, —OH, $—OCH_3$, $—NH_2$, or $—NO_2$. In some embodiments, the alkenyl is optionally substituted with halogen, —CN, —OH, or $—OCH_3$. In some embodiments, the alkenyl is optionally substituted with halogen.

"Alkynyl" refers to a straight-chain or branched-chain hydrocarbon monoradical having one or more carbon-carbon triple-bonds and having from two to about ten carbon atoms, more preferably from two to about six carbon atoms. Examples include, but are not limited to ethynyl, 2-propynyl, 2-butynyl, 1,3-butadiynyl and the like. Whenever it appears herein, a numerical range such as "$C_2$-$C_6$ alkynyl" or "$C_{2-6}$alkynyl", means that the alkynyl group can consist of 2 carbon atoms, 3 carbon atoms, 4 carbon atoms, 5 carbon atoms or 6 carbon atoms, although the present definition also covers the occurrence of the term "alkynyl" where no numerical range is designated. Unless stated otherwise specifically in the specification, an alkynyl group can be optionally substituted, for example, with oxo, halogen, amino, —CN, nitro, hydroxyl, haloalkyl, alkoxy, carboxyl, carboxylate, aryl, cycloalkyl, heterocycloalkyl, heteroaryl, and the like. In some embodiments, the alkynyl is optionally substituted with oxo, halogen, —CN, —COOH, $COOCH_3$, —OH, $—OCH_3$, $—NH_2$, or $—NO_2$. In some embodiments, the alkynyl is optionally substituted with halogen, —CN, —OH, or $—OCH_3$. In some embodiments, the alkynyl is optionally substituted with halogen.

"Alkylene" refers to a straight or branched divalent hydrocarbon chain. Unless stated otherwise specifically in the specification, an alkylene group can be optionally substituted, for example, with oxo, halogen, amino, —CN, nitro, hydroxyl, haloalkyl, alkoxy, carboxyl, carboxylate, aryl, cycloalkyl, heterocycloalkyl, heteroaryl, and the like. In some embodiments, the alkylene is optionally substituted with oxo, halogen, —CN, —COOH, $COOCH_3$, —OH, $—OCH_3$, $—NH_2$, or $—NO_2$. In some embodiments, the alkylene is optionally substituted with halogen, —CN, —OH, or $—OCH_3$. In some embodiments, the alkylene is optionally substituted with halogen.

"Alkoxy" refers to a radical of the formula $—OR^a$ where $R^a$ is an alkyl radical as defined. Unless stated otherwise specifically in the specification, an alkoxy group can be optionally substituted, for example, with oxo, halogen, amino, —CN, nitro, hydroxyl, haloalkyl, alkoxy, carboxyl, carboxylate, aryl, cycloalkyl, heterocycloalkyl, heteroaryl, and the like. In some embodiments, the alkoxy is optionally substituted with halogen, —CN, —COOH, $COOCH_3$, —OH, $—OCH_3$, $—NH_2$, or $—NO_2$. In some embodiments, the alkoxy is optionally substituted with halogen, —CN, —OH, or $—OCH_3$. In some embodiments, the alkoxy is optionally substituted with halogen.

"Aryl" refers to phenyl or naphthyl. Unless stated otherwise specifically in the specification, an aryl can be optionally substituted, for example, with halogen, amino, —CN, nitro, hydroxyl, alkyl, alkenyl, alkynyl, haloalkyl, alkoxy, carboxyl, carboxylate, aryl, cycloalkyl, heterocycloalkyl, heteroaryl, and the like. In some embodiments, the aryl is optionally substituted with halogen, methyl, ethyl, —CN, —COOH, $COOCH_3$, $—CF_3$, —OH, $—OCH_3$, $—NH_2$, or $—NO_2$. In some embodiments, the aryl is optionally substituted with halogen, methyl, ethyl, —CN, $—CF_3$, —OH, or $—OCH_3$. In some embodiments, the aryl is optionally substituted with halogen.

"Cycloalkyl" refers to a partially or fully saturated, monocyclic or polycyclic carbocyclic ring. In some embodiments, the cycloalkyl is fully saturated. Representative cycloalkyls include, but are not limited to, cycloalkyls having from three to ten carbon atoms (e.g., $C_3$-$C_{10}$ fully saturated cycloalkyl or $C_3$-$C_{10}$ cycloalkenyl), from three to eight carbon atoms (e.g., $C_3$-$C_8$ fully saturated cycloalkyl or $C_3$-$C_8$ cycloalkenyl), from three to six carbon atoms (e.g., $C_3$-$C_6$ fully saturated cycloalkyl or $C_3$-$C_6$ cycloalkenyl), or three to five carbon atoms (e.g., $C_3$-$C_5$ fully saturated cycloalkyl or $C_3$-$C_5$ cycloalkenyl). Monocyclic cycloalkyls include, for example, cyclopropyl, cyclobutyl, cyclopentyl, cyclohexyl, cycloheptyl, and cyclooctyl. Polycyclic cycloalkyls include, for example, adamantyl, norbornyl, and 7,7-dimethyl-bicyclo[2.2.1]heptanyl. Unless stated otherwise specifically in the specification, a cycloalkyl is optionally substituted, for example, with oxo, halogen, amino, —CN, nitro, hydroxyl, alkyl, alkenyl, alkynyl, haloalkyl, alkoxy, carboxyl, carboxylate, aryl, cycloalkyl, heterocycloalkyl, heteroaryl, and the like. In some embodiments, a cycloalkyl is optionally substituted with oxo, halogen, methyl, ethyl, —CN, —COOH, $COOCH_3$, $—CF_3$, —OH, $—OCH_3$, $—NH_2$, or $—NO_2$. In some embodiments, a cycloalkyl is optionally substituted with oxo, halogen, methyl, ethyl, —CN, $—CF_3$, —OH, or $—OCH_3$. In some embodiments, the cycloalkyl is optionally substituted with halogen.

"Halo" or "halogen" refers to bromo, chloro, fluoro or iodo. In some embodiments, halogen is fluoro or chloro. In some embodiments, halogen is fluoro.

"Haloalkyl" refers to an alkyl radical, as defined above, that is substituted by one or more halo radicals, as defined above, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl, and the like.

"Haloalkoxy" refers to an alkoxy radical, as defined above, that is substituted by one or more halo radicals (e.g., mono-haloalkoxy, di-haloalkoxy and tri-haloalkoxy). Such groups include but are not limited to, chloromethoxy, fluoromethoxy, difluoromethoxy, trifluoromethoxy, 1-chloro-2-fluoromethoxy and 2-fluoroisobutoxy. In some embodiments, the haloalkoxy group can have 1 to 6 carbon atoms. The haloalkoxy group of the compounds can be designated as "haloC1-C6 alkoxy" or similar designations.

"Heterocycloalkyl" refers to a three-, four-, five-, six-, seven-, eight-, nine-, ten-, up to 18-membered monocyclic, bicyclic, and tricyclic ring system wherein carbon atoms together with from 1 to 5 heteroatoms constitute said ring system and optionally containing one or more unsaturated bonds situated in such a way, however, that a fully delocalized pi-electron system (aromatic system) does not occur in the monocyclic ring or in at least one ring of the bicyclic or tricyclic ring system. The heteroatom(s) is an element other than carbon including, but not limited to, oxygen, sulfur, and nitrogen. In some embodiments, the heterocycloalkyl is fully saturated. In some embodiments, the heterocycloalkyl comprises one to three heteroatoms selected from the group consisting of nitrogen, oxygen, and sulfur. In some embodiments, the heterocycloalkyl comprises one to three heteroatoms selected from the group consisting of nitrogen and oxygen. In some embodiments, the heterocycloalkyl comprises one to three nitrogens. In some embodiments, the heterocycloalkyl comprises one or two nitrogens. In some embodiments, the heterocycloalkyl comprises one nitrogen. In some embodiments, the heterocycloalkyl comprises one nitrogen and one oxygen. Unless stated otherwise specifically in the specification, the heterocycloalkyl radical can be a monocyclic, bicyclic, tricyclic or tetracyclic ring system. Representative heterocycloalkyls include, but are not limited to, heterocycloalkyls having from two to fifteen carbon atoms (e.g., $C_2$-$C_{15}$ fully saturated heterocycloalkyl or $C_2$-$C_{15}$ heterocycloalkenyl), from two to ten carbon atoms (e.g., $C_2$-$C_{10}$ fully saturated heterocycloalkyl or $C_2$-$C_{10}$ heterocycloalkenyl), from two to eight carbon atoms (e.g., $C_2$-$C_8$ fully saturated heterocycloalkyl or $C_2$-$C_8$ heterocycloalkenyl), from two to seven carbon atoms (e.g., $C_2$-$C_7$ fully saturated heterocycloalkyl or $C_2$-$C_7$ heterocycloalkenyl), from two to six carbon atoms (e.g., $C_2$-$C_6$ fully saturated heterocycloalkyl or $C_2$-$C_7$ heterocycloalkenyl), from two to five carbon atoms (e.g., $C_2$-$C_5$ fully saturated heterocycloalkyl or $C_2$-$C_5$ heterocycloalkenyl), or two to four carbon atoms (e.g., $C_2$-$C_4$ fully saturated heterocycloalkyl or $C_2$-$C_4$ heterocycloalkenyl). Examples of such heterocycloalkyl radicals include, but are not limited to, aziridinyl, azetidinyl, oxetanyl, dioxolanyl, thienyl[1,3]dithianyl, decahydroisoquinolyl, imidazolinyl, imidazolidinyl, isoindolinyl, isothiazolidinyl, isoxazolidinyl, morpholinyl, octahydroindolyl, octahydroisoindolyl, oxazolidinyl, piperidinyl, piperazinyl, pyrrolidinyl, pyrazolidinyl, quinuclidinyl, thiazolidinyl, tetrahydrofuryl, trithianyl, tetrahydropyranyl, thiomorpholinyl, and thiamorpholinyl. In some embodiments, heterocycloalkyls have from 2 to 10 carbons in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e., skeletal atoms of the heterocycloalkyl ring). In some embodiments, the heterocycloalkyl is a 3- to 8-membered heterocycloalkyl. Unless stated otherwise specifically in the specification, a heterocycloalkyl can be optionally substituted as described below, for example, with oxo, halogen, amino, —CN, nitro, hydroxyl, alkyl, alkenyl, alkynyl, haloalkyl, alkoxy, carboxyl, carboxylate, aryl, cycloalkyl, heterocycloalkyl, heteroaryl, and the like. In some embodiments, the heterocycloalkyl is optionally substituted with oxo, halogen, methyl, ethyl, —CN, —COOH, $COOCH_3$, —$CF_3$, —OH, —$OCH_3$, —$NH_2$, or —$NO_2$. In some embodiments, the heterocycloalkyl is optionally substituted with halogen, methyl, ethyl, —CN, —$CF_3$, —OH, or —$OCH_3$. In some embodiments, the heterocycloalkyl is optionally substituted with halogen.

"Heteroaryl" refers to a 5- to 14-membered ring system radical comprising one to thirteen carbon atoms, one to six heteroatoms selected from the group consisting of nitrogen, oxygen, phosphorous, and sulfur, and at least one aromatic ring. In some embodiments, the heteroaryl comprises one to three heteroatoms selected from the group consisting of nitrogen, oxygen, and sulfur. In some embodiments, the heteroaryl comprises one to three heteroatoms selected from the group consisting of nitrogen and oxygen. In some embodiments, the heteroaryl comprises one to three nitrogens. In some embodiments, the heteroaryl comprises one or two nitrogens. In some embodiments, the heteroaryl comprises one nitrogen. The heteroaryl radical can be a monocyclic, bicyclic, tricyclic or tetracyclic ring system. In some embodiments, the heteroaryl is a 5- to 10-membered heteroaryl. In some embodiments, the heteroaryl is a 5- to 6-membered heteroaryl. In some embodiments, the heteroaryl is a 6-membered heteroaryl. In some embodiments, the heteroaryl is a 5-membered heteroaryl. Examples include, but are not limited to, benzimidazolyl, benzothiazolyl, imidazolyl, indazolyl, indolyl, indazolyl, isoquinolyl, indolizinyl, isoxazolyl, 1,5-naphthyridinyl, 1,6-naphthyridinyl, oxadiazolyl, oxazolyl, phenazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, isoquinolinyl, thiazolyl, thiadiazolyl, triazolyl, tetrazolyl, triazinyl, and thiophenyl (i.e., thienyl). Unless stated otherwise specifically in the specification, a heteroaryl can be optionally substituted, for example, with halogen, amino, —CN, nitro, hydroxyl, alkyl, alkenyl, alkynyl, haloalkyl, alkoxy, carboxyl, carboxylate, aryl, cycloalkyl, heterocycloalkyl, heteroaryl, and the like. In some embodiments, the heteroaryl is optionally substituted with halogen, methyl, ethyl, —CN, —COOH, $COOCH_3$, —$CF_3$, —OH, —$OCH_3$, —$NH_2$, or —$NO_2$. In some embodiments, the heteroaryl is optionally substituted with halogen, methyl, ethyl, —CN, —$CF_3$, —OH, or —$OCH_3$. In some embodiments, the heteroaryl is optionally substituted with halogen.

CERTAIN EMBODIMENTS

Embodiment 1. A method of reducing a number of microcalcifications in an atherosclerotic plaque comprising:

administering a pharmaceutical composition comprising a therapeutically effective amount of a tissue-nonspecific alkaline phosphatase (TNAP) inhibitor, wherein administering the pharmaceutical composition comprising the therapeutically effective amount of the TNAP inhibitor reduces the number of microcalcifications in the atherosclerotic plaque.

Embodiment 2. A method of preventing, arresting, or reducing the development of plaque calcifications in a patient in need thereof comprising:

identifying a patient having atherosclerosis; and administering a pharmaceutical composition to the patient comprising a therapeutically effective amount of a tissue-nonspecific alkaline phosphatase (TNAP) inhibitor, wherein administering the pharmaceutical composition comprising the therapeutically effective amount of the TNAP inhibitor prevents, arrests, or reduces the development of plaque calcifications.

Embodiment 3. A method of treating atherosclerosis comprising administering a pharmaceutical composition to a patient comprising a therapeutically effective amount of a tissue-nonspecific alkaline phosphatase (TNAP) inhibitor.

Embodiment 4. The method of embodiments 1-3, wherein the TNAP inhibitor is selected from the group consisting of a TNAP-targeting short hairpin RNA (shTNAP), a TNAP-targeting guide RNA (sgTNAP), and a small molecule.

Embodiment 5. The method of embodiment 4, wherein the TNAP inhibitor is a shTNAP, and the shTNAP is doxycycline-inducible.

Embodiment 6. The method of embodiments 1-3, wherein the TNAP inhibitor is a small molecule.

Embodiment 7. The method of embodiment 6, wherein the small molecule is a compound of Formula I, or a pharmaceutically acceptable salt, polymorph, solvate, tautomer, metabolite, or N-oxide thereof:

(Formula I)

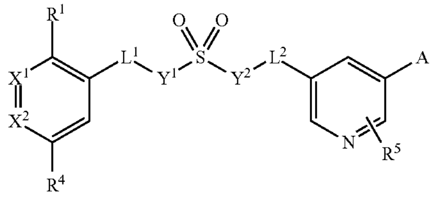

wherein:

$Y^1$ and $Y^2$ are independently a bond or —N($R^6$)—, wherein at least one of $Y^1$ and $Y^2$ is —N($R^6$)—;

$L^1$ and $L^2$ are independently a bond or optionally substituted alkylene;

$X^1$ is =N— or =C($R^2$)—;

$X^2$ is =N— or =C($R^3$)—;

$R^1$ and $R^4$ are independently selected from the group consisting of hydrogen, halogen, —CN, —C(O)—N($R^7$)—$R^8$, —C(O)—O—$R^9$, optionally substituted alkyl, optionally substituted cycloalkyl, optionally substituted heterocycloalkyl, optionally substituted alkoxy, haloalkyl, haloalkoxy, optionally substituted phenyl, and optionally substituted 5- or 6-membered heteroaryl;

$R^2$, $R^3$, and $R^5$ are independently selected from the group consisting of hydrogen, halogen, —CN, —C(O)—N($R^7$)—$R^8$, —C(O)—O—$R^9$, optionally substituted alkyl, optionally substituted cycloalkyl, optionally substituted heterocycloalkyl, optionally substituted alkoxy, haloalkyl, haloalkoxy, optionally substituted phenyl, and optionally substituted 5- or 6-membered heteroaryl;

$R^6$ is hydrogen, optionally substituted alkyl, optionally substituted alkenyl, or optionally substituted alkynyl;

$R^7$ and $R^8$ are independently hydrogen, optionally substituted alkyl, haloalkyl, optionally substituted cycloalkyl, optionally substituted heterocycloalkyl, optionally substituted phenyl, or $R^7$ and $R^8$ together with the nitrogen atom to which they are attached form an optionally substituted heterocycloamino;

$R^9$ is selected from the group consisting of hydrogen, optionally substituted alkyl, haloalkyl, optionally substituted cycloalkyl, optionally substituted heterocycloalkyl, and optionally substituted phenyl; and A is selected from the group consisting of —C(O)—N($R^7$)—$R^8$, —C(O)—O—$R^9$, optionally substituted phenyl, and optionally substituted 5- or 6-membered heteroaryl.

Embodiment 8. The method of embodiments 1-3, wherein the method further comprises reducing plaque inflammation, reducing plaque calcification, reducing plaque size, reducing blood cholesterol, reducing serum lipid levels, inhibiting TNAP present in a liver, increasing plaque stability, and combinations thereof.

Embodiment 9. The method of embodiments 1-3, wherein the pharmaceutical composition is administered to a subject via a route selected from the group consisting of subcutaneous injection, intramuscular injection, and intravenous injection.

Embodiment 10. The method of embodiment 9, wherein the pharmaceutical composition further comprises a delivery vehicle selected from the group consisting of liposomes, nanoparticles, microparticles, microspheres, lipid particles, vesicles, poloxamers, and polycationic materials.

Embodiment 11. The method of embodiment 9, wherein the subject has been diagnosed with an obesity-related condition.

Embodiment 12. The method of embodiment 11, wherein the obesity-related condition is selected from the group consisting of obesity-related insulin resistance and Type-2 diabetes.

Embodiment 13. The method of embodiment 9, wherein the method comprises administering the pharmaceutical composition in combination with a lipid-lowering agent.

Embodiment 14. The method of embodiment 13, wherein the lipid-lowering agent is a statin.

Embodiment 15. The method of embodiment 14, wherein the statin is selected from the group consisting of lovastatin, pravastatin, simvastatin, atorvastatin, cerivastatin, fluvastatin, pravastatin, pitavastatin, and rosuvastatin.

Embodiment 16. The method of embodiments 1-3, further comprising measuring a biomarker in a biological sample obtained from an individual prior to administering the therapeutically effective amount of the TNAP inhibitor.

Embodiment 17. The method of embodiment 16, wherein measuring the biomarker comprises assaying mRNA expression level of the biomarker.

Embodiment 18. The method of embodiment 16, wherein measuring the biomarker comprises assaying protein level of the biomarker.

EXAMPLES

The following illustrative examples are representative of embodiments of the stimulation, systems, and methods described herein and are not meant to be limiting in any way.

Materials and Methods

Figure 8A:
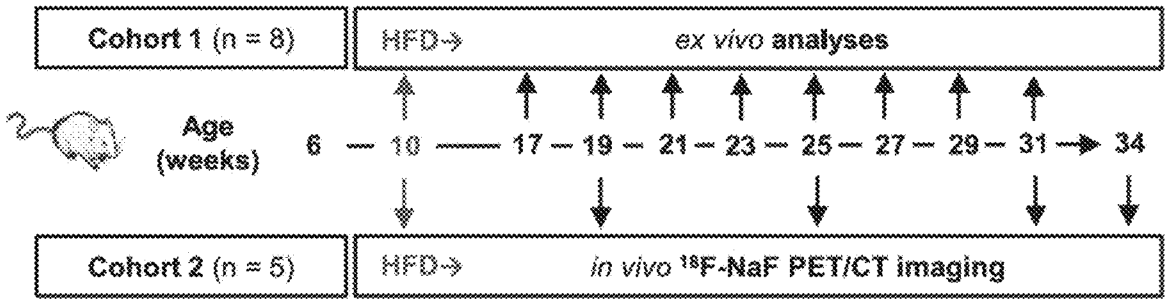
FIG. 8A illustrates ApoE-deficient mice fed a HFD from 10 weeks of age, analyzed every two weeks after sacrifice (cohort 1), and in vivo at 19, 25, 31 and 34 weeks (cohort 2).
Figure 9A:
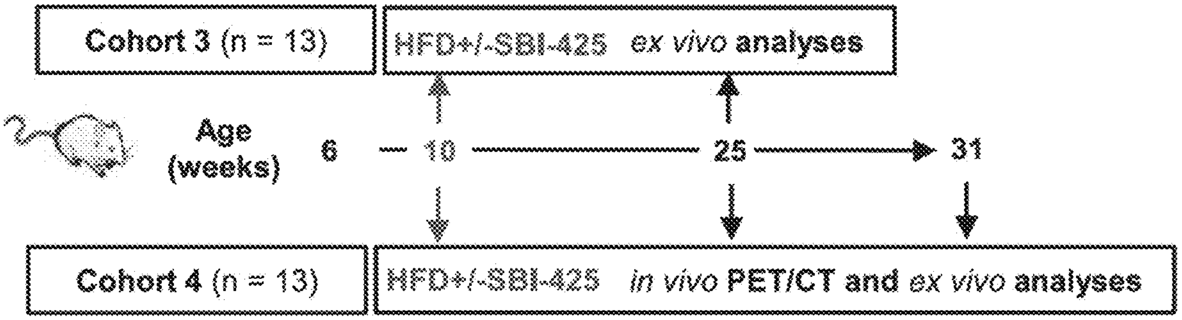
FIG. 9A illustrates SBI-425 that was administered from 10 weeks of age in ApoE-deficient mice and calcification that was monitored after sacrifice in cohort 3, or in vivo and after sacrifice in cohort 4.
Figure 9B:
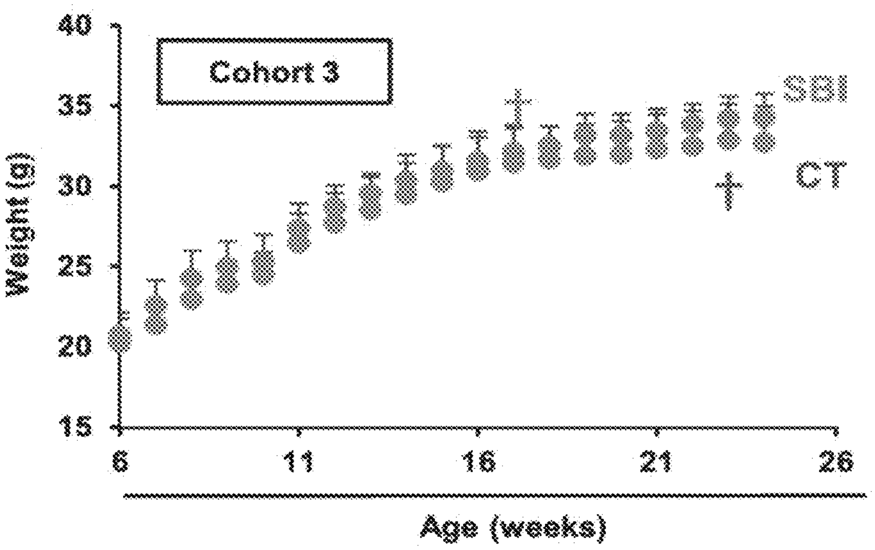
FIGS. 9B and 9C illustrate weight gain in ApoE-deficient mice treated or not with SBI-425 in cohorts 3 and 4; † indicates a death.
Figure 9C:
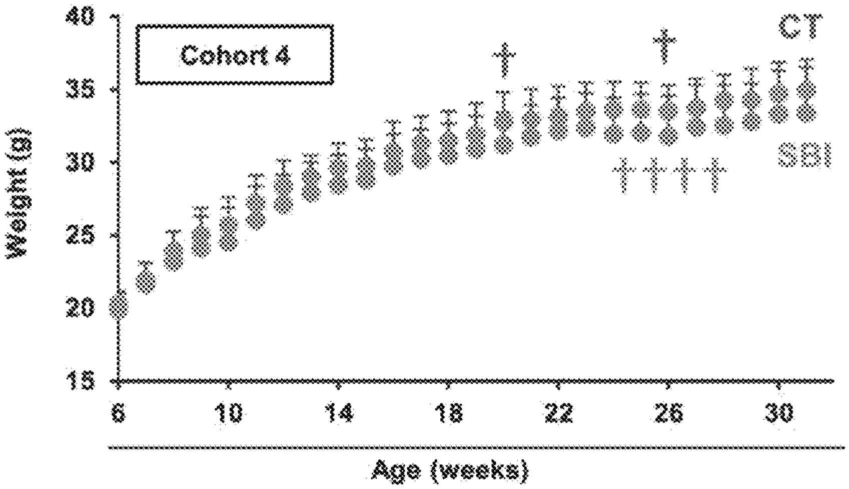
Figure 9D:
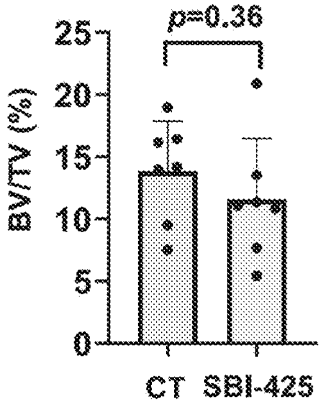
FIGS. 9D-9H illustrate bone architecture parameters determined at 31 weeks in ApoE-deficient mice treated or not with SBI-425 in cohort 3 (B, n=7 per group). Results are shown as mean±standard deviation. In B, statistical analyses were performed with student t-test. BMD: bone mineral density; BV: bone volume; CT: control (untreated mice); SBI: SBI-425; Tb: trabecular; TV: total volume.
Figure 9E:
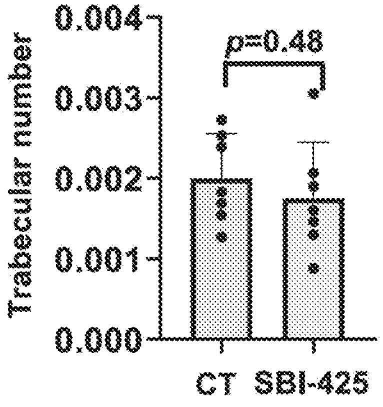
Figure 9F:
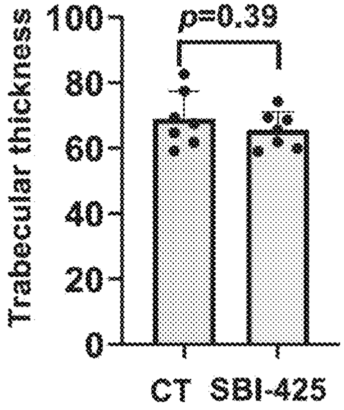
Figure 9G:
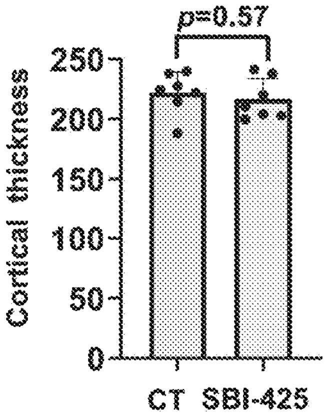
Figure 9H:
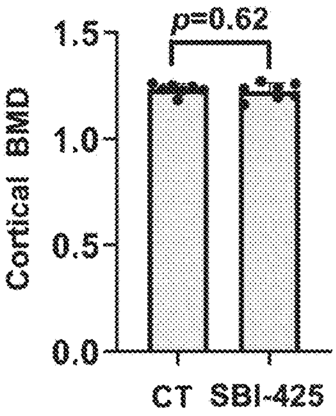
Figure 10A:
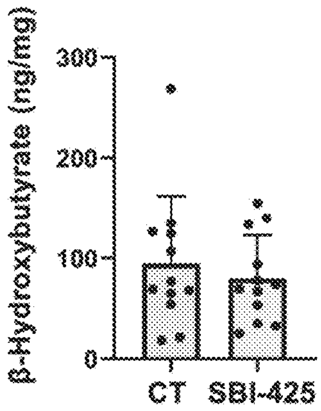
FIGS. 10A-10Z, 11A-11D, 12A-12Z, and 13A-13I illustrate quantification of liver (FIGS. 10A-10Z and 11A-11D) and kidney (FIGS. 12A-12Z and 13A-13I) metabolite levels as determined by NMR-metabolomics.
Figure 10B:
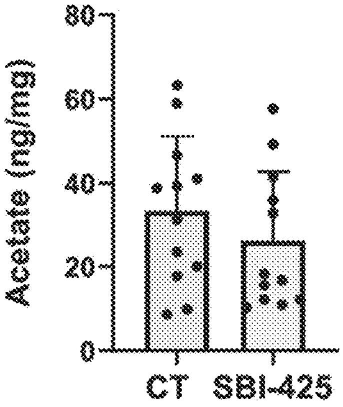
Figure 10C:
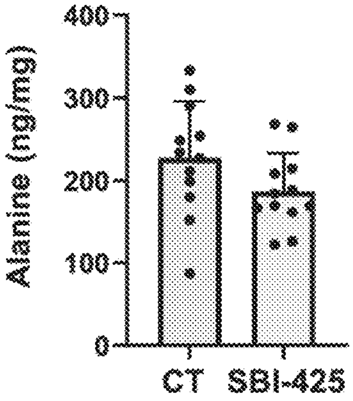
Figure 10D:
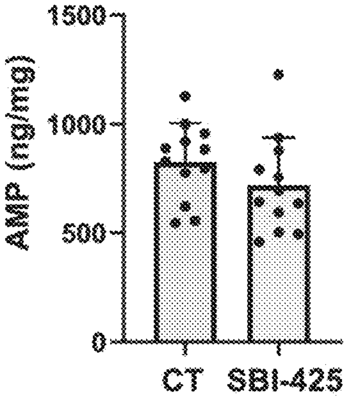
Figure 10E:
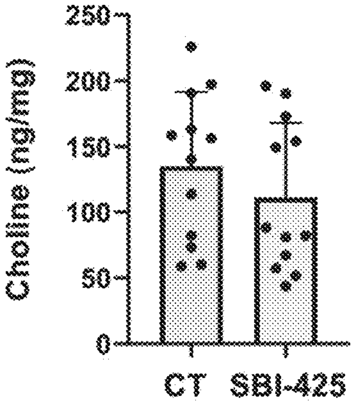
Figure 10F:
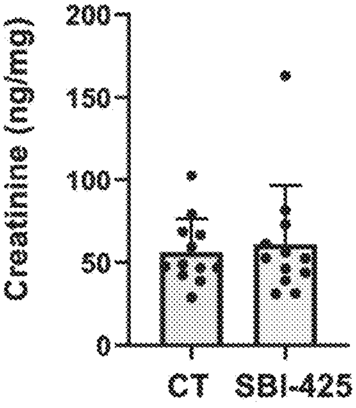
Figure 10G:
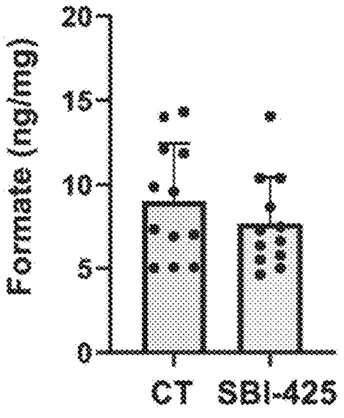
Figure 10H:
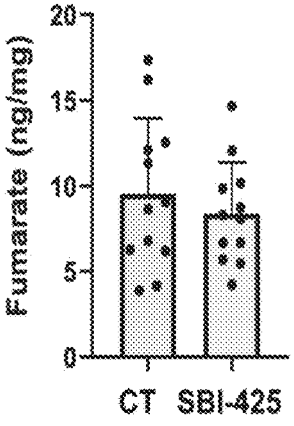
Figure 10I:
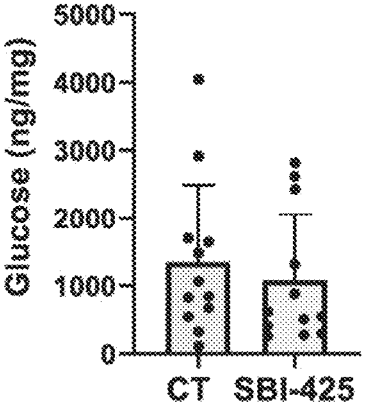
Figure 10J:
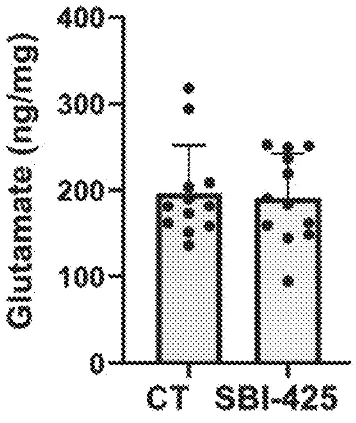
Figure 10K:
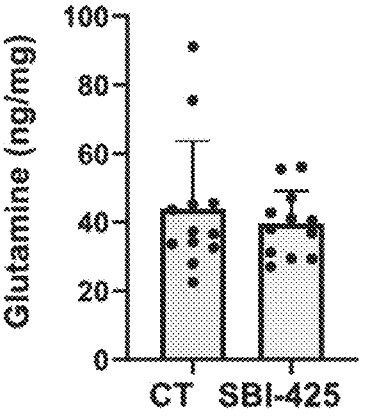
Figure 10L:
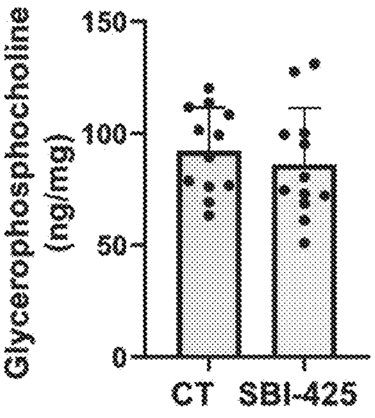
Figure 10M:
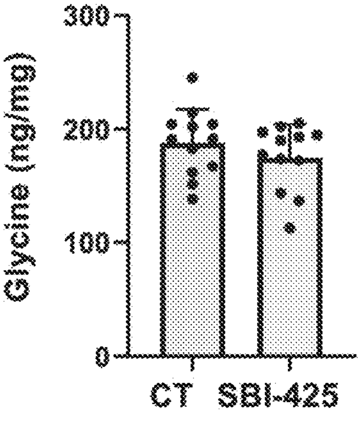
Figure 10N:
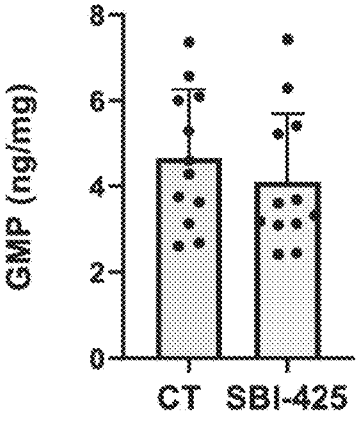
Figure 10O:
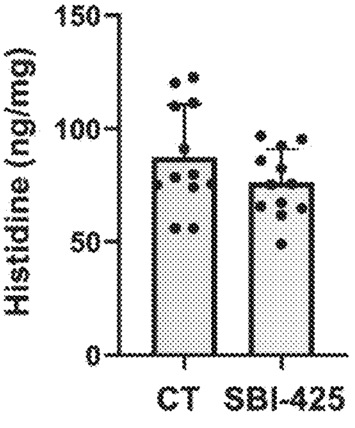
Figure 10P:
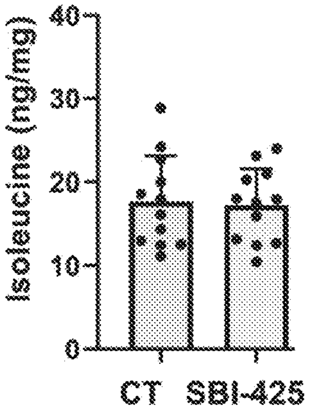
Figure 10Q:
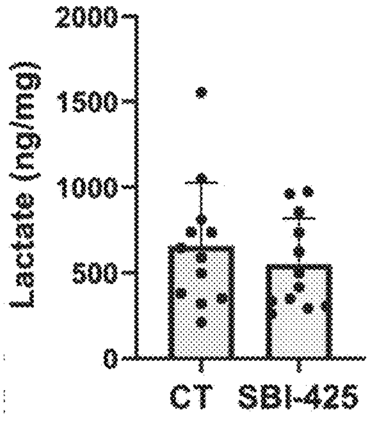
Figure 10R:
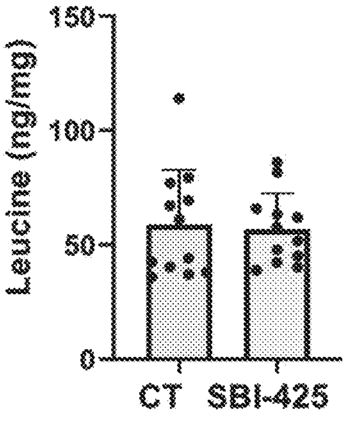
Figure 10S:
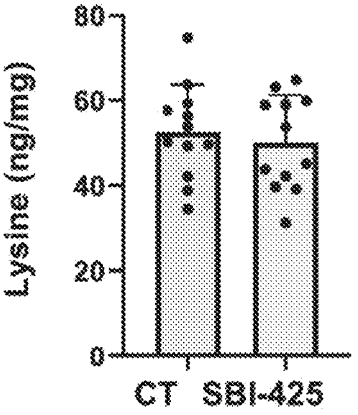
Figure 10T:
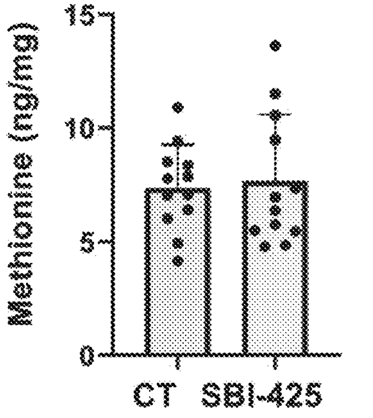
Figure 10U:
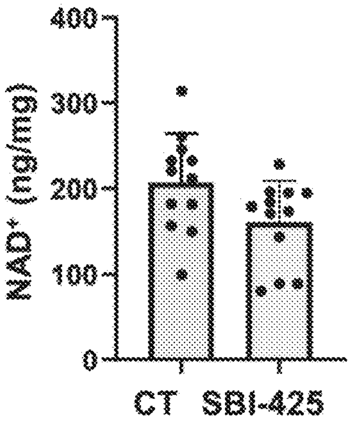
Figure 10V:
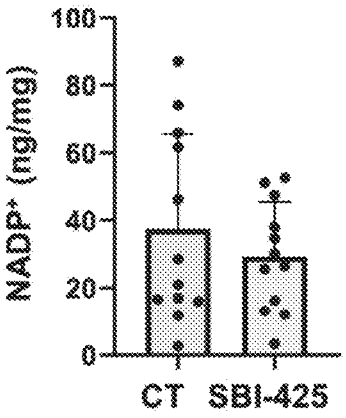
Figure 10W:
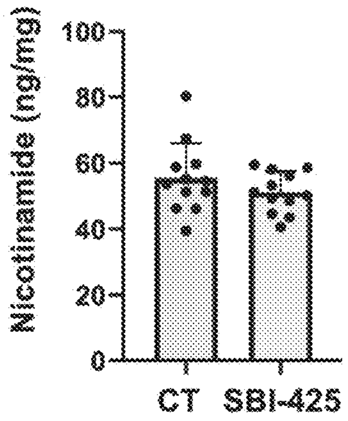
Figure 10X:
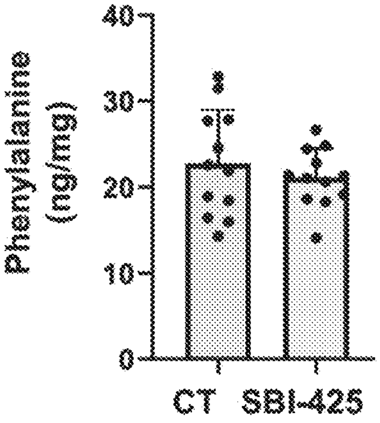
Figure 10Y:
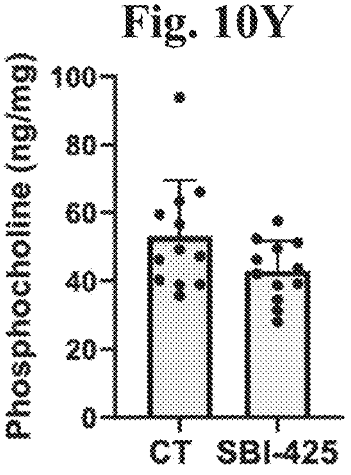
Figure 10Z:
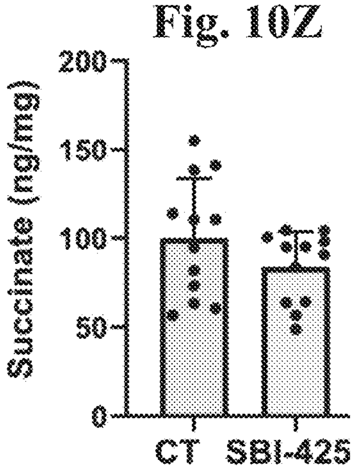
Figure 11A:
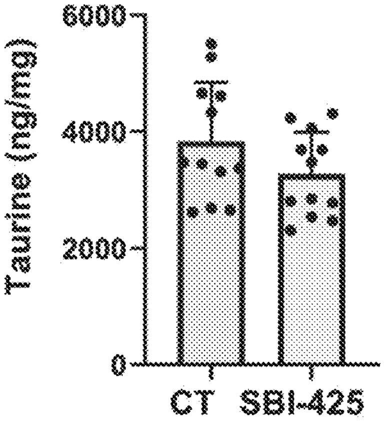
Figure 11B:
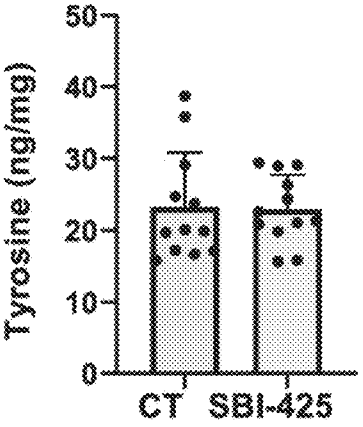
Figure 11C:
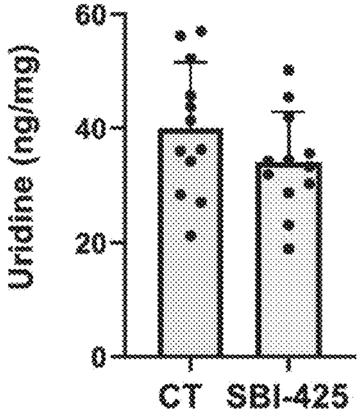
Figure 11D:
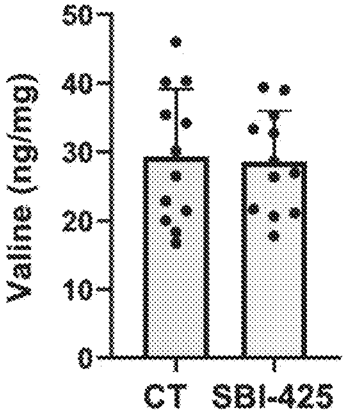
Figure 12A:
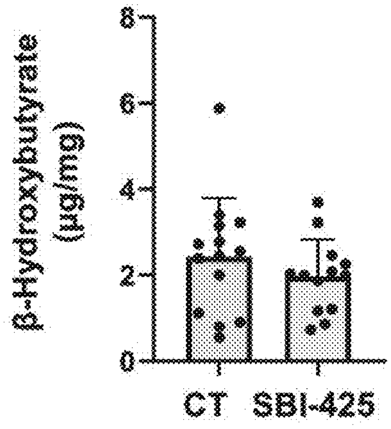
Figure 12B:
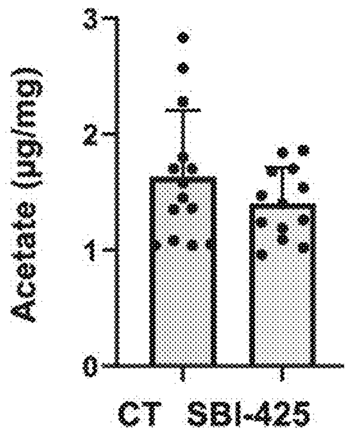
Figure 12C:
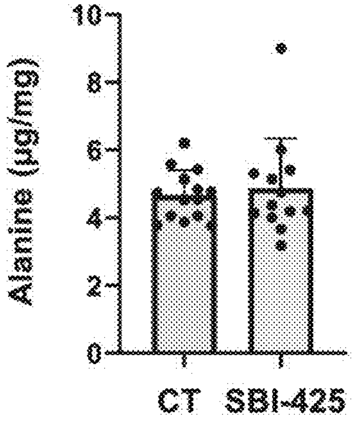
Figure 12D:
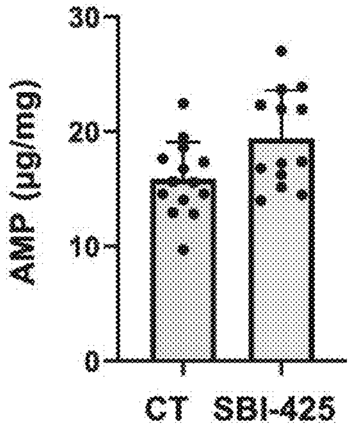
Figure 12E:
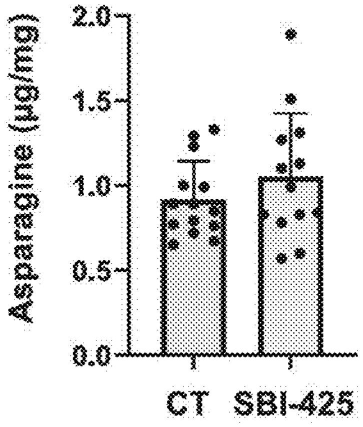
Figure 12F:
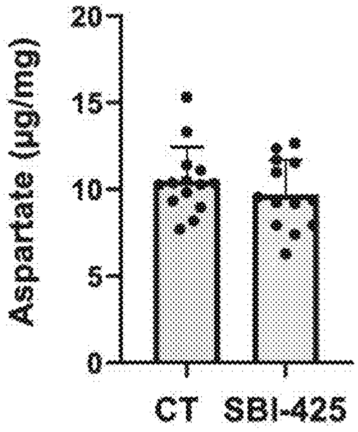
Figure 12G:
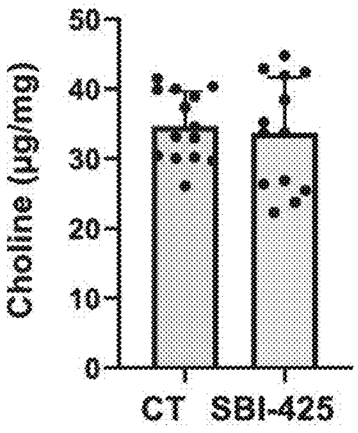
Figure 12H:
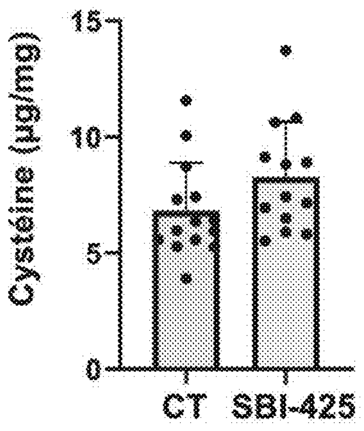
Figure 12I:
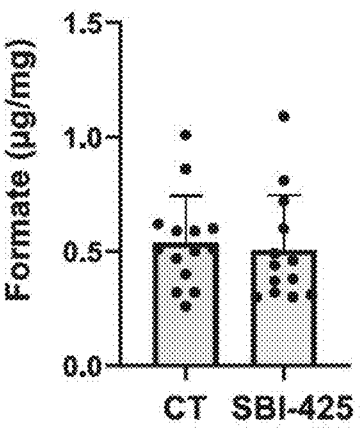
Figure 12J:
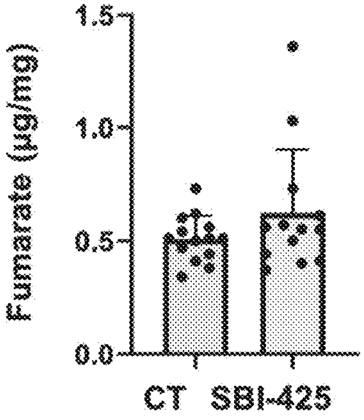
Figure 12K:
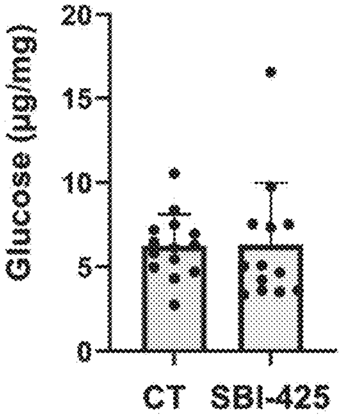
Figure 12L:
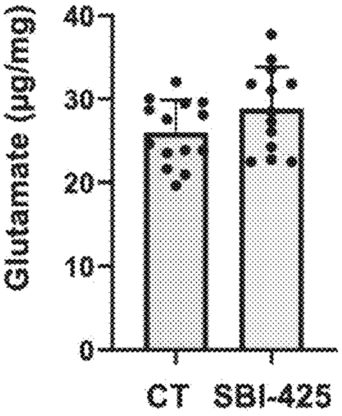
Figure 12M:
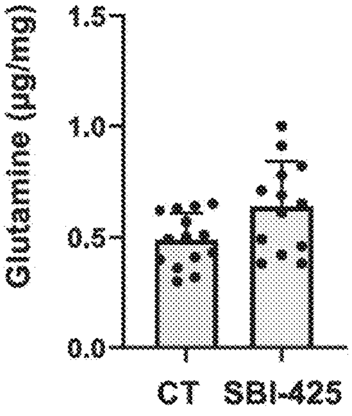
Figure 12N:
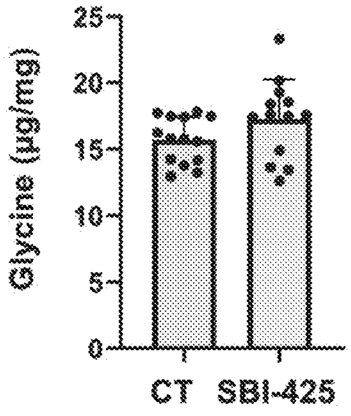
Figure 12O:
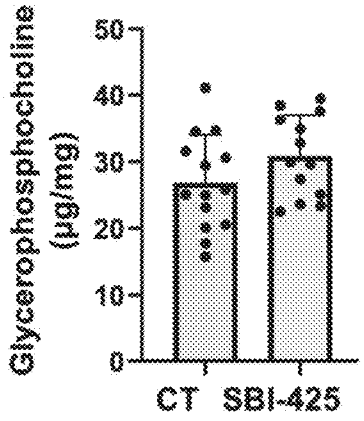
Figure 12P:
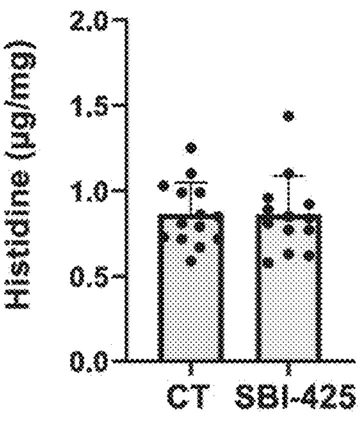
Figure 12Q:
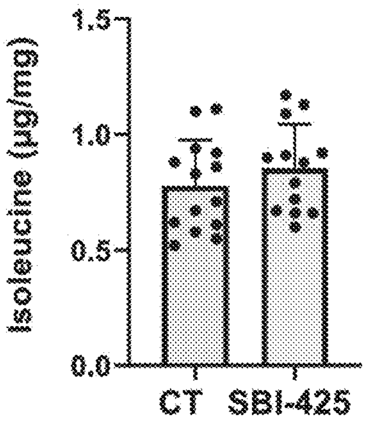
Figure 12R:
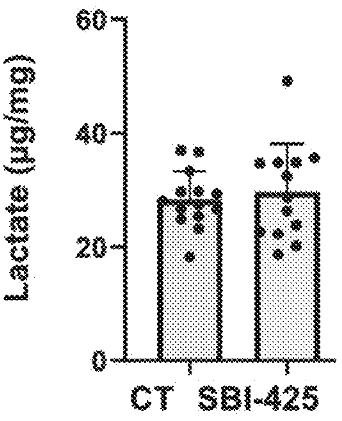
Figure 12S:
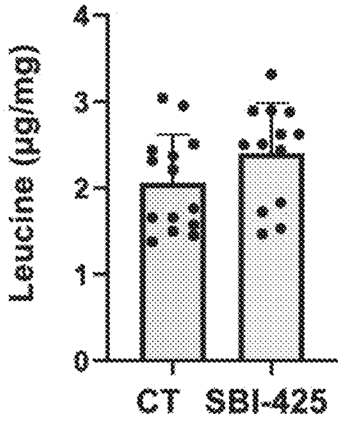
Figure 12T:
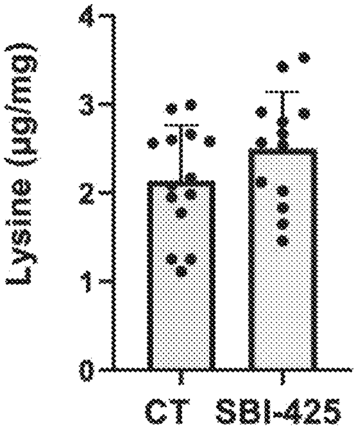
Figure 12U:
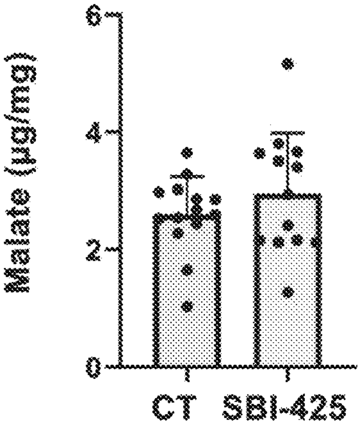
Figure 12V:
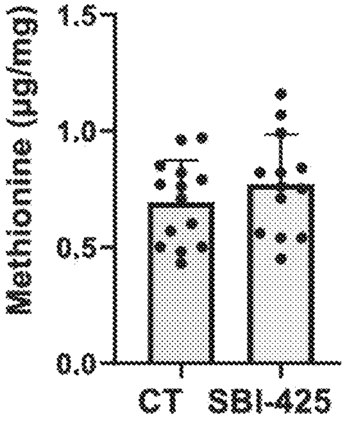
Figure 12W:
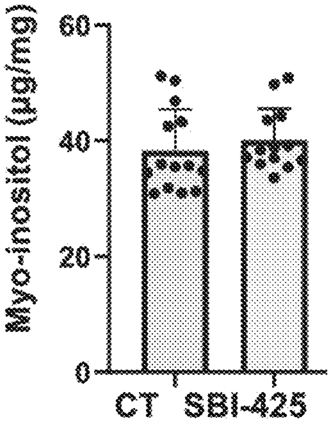
Figure 12X:
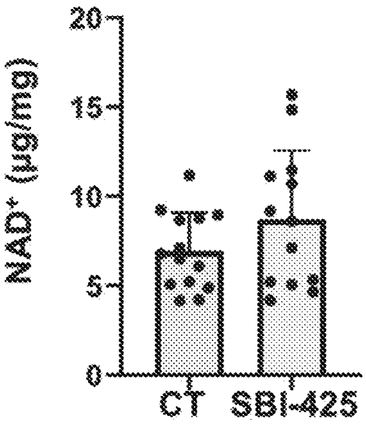
Figure 12Y:
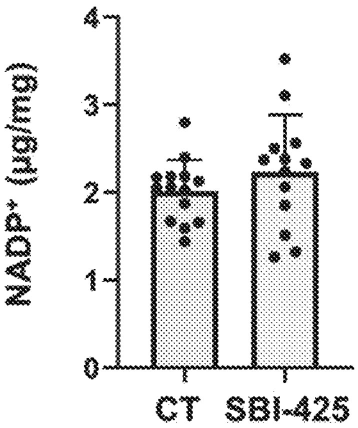
Figure 12Z:
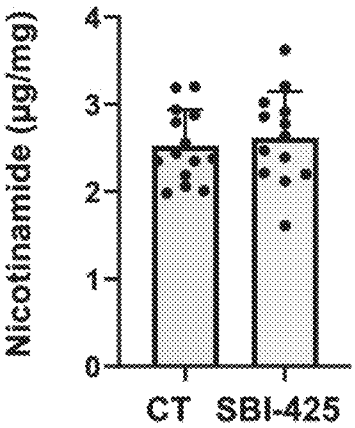
Figure 13A:
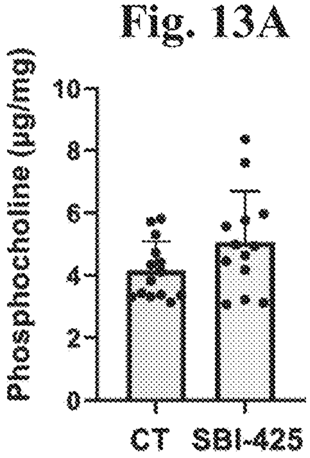
Figure 13B:
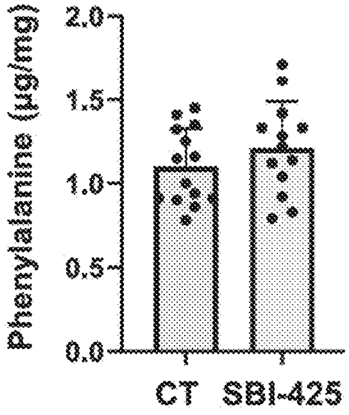
Figure 13C:
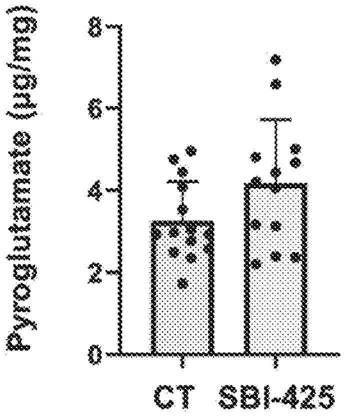
Figure 13D:
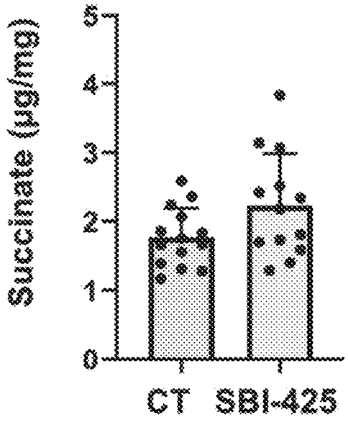
Figure 13E:
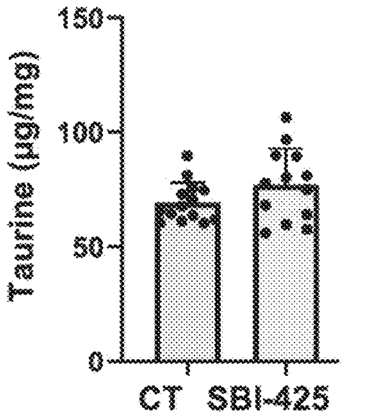
Figure 13F:
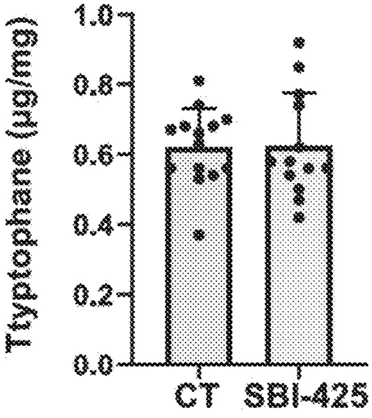
Figure 13G:
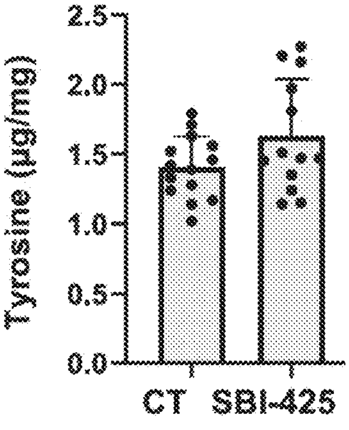
Figure 13H:
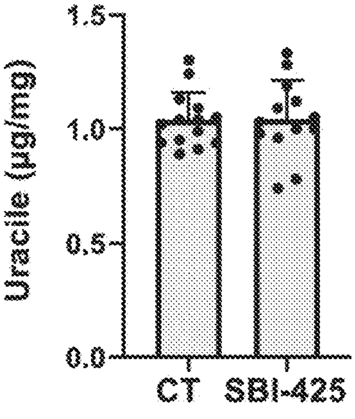
Figure 13I:
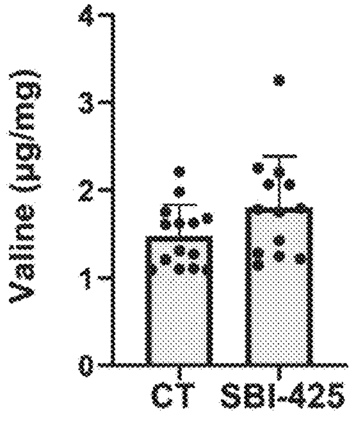

Four cohorts of mice were used in these studies (FIGS. 8A and 9A). Cohorts 1 and 2 were devoted to the in vivo and ex vivo characterization of TNAP-associated plaque calcification. 6-week-old ApoE-deficient male mice were received at the animal facility and placed in conventional cages with 5 mice per cage. Mice were maintained on a 12-hrs light-dark cycle (7:00 am-7:00 μm) and were supplied with food and water ad libitum. From 10 weeks of age, they were fed ad libitum with a high fat diet (HFD, D12108C, Research Diets, New Brunswick, USA) containing 40% fat (kcal) and 1.25% cholesterol (weight). In cohort 1, 8 mice were sacrificed every 2 weeks between weeks 17 to 31, for histological and molecular analyses. Total body weight was measured weekly after starting the HFD. The sacrifice was done after anesthesia with isoflurane and intracardiac blood puncture by $CO_2$ inhalation. Tissues were harvested as described below. The abdominal aorta was used for quantitative polymerase chain reaction (PCR) analyses. Mice from cohort 2 were used to analyze aorta calcification with $^{18}$F—NaF μPET and μCT and to compare the in vivo data with the ex vivo results obtained in cohort 1. Animals were transferred from the animal facility to the Cermep imaging platform. Cohorts 3 and 4 were used to determine in vivo and ex vivo the impact of TNAP inhibition on the vasculature, liver, bones, and kidneys. According to the results obtained in cohorts 1 and 2, TNAP inhibitor SBI-425 (30 mg/kg/day, formulated as a food admixture in the HFD) was administered in a preventive manner from 10 weeks of age. Treatment was stopped at 25 weeks or 31 weeks of age. Plaque calcification was analyzed at 25 weeks, and possible side effects of TNAP inhibition were explored in mice aged 31 weeks. Mice in cohort 3 (2 groups of 13 mice) were used for ex vivo analysis, and mice in cohort 4 (2 groups of 12 mice) for in vivo imaging and ex vivo analyses.

Mice were placed into a chamber connected to an isoflurane anesthesia unit. Anesthesia was induced using an airflow rate of 0.8 L/min and 4% isoflurane, and airflow rate was then maintained to 0.6 L/min with 2% isoflurane during the scans. After induction, mice were injected with 0.36 MBq/g of $^{18}F$—NaF in 0.1 mL saline via tail vein (19 scans) or in retro-orbital venous sinus (16 scans) when the tail veins were not available. After injection, the animals were placed in the prone position on the scanning bed. PET-CT images were obtained using a micro PET-CT scanner (Inveon PET-CT, Siemens, Germany). Mice were positioned into the CT system and imaged using the magnification low acquisition settings (acquisition parameters: attenuation mode; projection: 120; rotation: 200°; estimated scan time: 492 s; binning 4×4; effective voxel size: 0.111×0.111×0.111 $mm^3$; voltage: 80 kV; current: 500 μA; filter thickness: 0.5 mm; and exposure: 200 ms). After CT acquisition, mice were moved into the center of the PET scanner (axial field of view: 127 mm). PET acquisition started exactly one hour after $^{18}F$—NaF injection, for a total scan time of twenty minutes. Then, mice were allowed to recover into a lead shielded cage. Static images of the 20-min PET acquisitions were reconstructed with attenuation and scatter correction by 3D ordinary Poisson ordered subsets expectation maximization (OP-OSEM3D) with 4 iterations and a zoom factor of 2. The reconstructed volume was constituted of 159 slices of 128×128 matrix voxels, with voxel size 0.388×0.388×0.796 $mm^3$. CT data were reconstructed using a Feldkamp algorithm with a down sample of 1 (Inveon Acquisition Workplace, Siemens). After reconstruction, the PET and CT data were coregistered. Images were analyzed using Inveon Research workplace (Siemens). The presence of atherosclerotic plaques was evaluated both in CT and PET images. Due to the higher resolution of CT scan, regions-of-interest (ROI) of the aortic arch were drawn on CT images. Only voxels above the threshold of 390 Hounsfield Unit (calcified structure) were considered. The ROIs were exported onto the coregistered PET images in order to measure $^{18}F$—NaF uptake. Standardized uptake value ratio (SUVR) was calculated using the whole body SUV as reference.

After euthanasia, the heart and vasculature were perfused with sterile NaCl 0.9%. The aortic root and the aortic arch, with the major arteries that stem from them (brachiocephalic, left common carotid and left subclavian), were dissected and frozen in optimal cutting temperature medium (OCT, Thermo Scientific) and stored at −80° C. before serial cryo-sectioning. The aortic root, aortic arch and carotid were dissected under a microscope, frozen in optimal cutting medium (OCT, Thermo Scientific) and stored at −80° C. before serial cryo-sectioning. Abdominal aortas were dissected, rinsed once with sterile phosphate buffered saline (PBS) pH 7.8, and frozen until RNA extraction. Cryostat sections (5-μm thick) were cut at −21° C. using a Leica CM3050 S cryostat (Leica), mounted on glass slides (SuperFrost Plus Gold glass slides, Thermo scientific) and stored at −80° C. until use. Four sections of 5-μm thickness were harvested per slide, yielding 25 to 45 slides per mouse. Prior to analysis, frozen tissue sections were air dried at room temperature for 10 min and eight consecutive sections were taken from each mouse at 15-μm intervals. Calcification was imaged by near infrared fluorescence (NIRF) with the calcium tracer osteosense (OS) (PerkinElmer, ex/em 650/680 nm). Briefly, frozen sections were treated overnight with OS 680 (1:100) before NIRF imaging. Quantification was performed by computer image analysis using Image J software (NIH, Bethesda, MD) by averaging of measurements from 2 sections of 15 μm apart using ImageJ software. Alkaline phosphatase activity was stained in serial sections using nitro blue tetrazolium/5-Bromo-4-chloro-3-indolyl phosphate (NBT/BCIP) solution (37).

To perform CD68 immunohistochemical staining, serial frozen sections of aortic arch were fixed in acetone (−20° C.) for 10 min and were air dried afterwards for 10 min. Endogenous peroxidase activity was neutralized with 0.3% $H_2O_2$ for 10 min followed by 3 washing steps of 5 min each using TBS pH 7.4 containing 0.025% Triton-X100. Sections were incubated with TBS containing 5% normal goat serum (Abcam) and 1% bovine serum albumin (BSA) for 1 h to reduce non-specific background staining. Sections were subsequently incubated overnight at 4° C. with anti-CD68 antibody (Abcam ab125212) diluted in TBS containing 1% BSA. Horseradish peroxidase-conjugated polyclonal anti-rabbit secondary antibody (Abcam) was applied for 1 h and then revealed with a DAB staining kit (Abcam). Preparations were counterstained with hematoxylin-eosin (Mayer's hematoxylin solution, Sigma). Negative control sections were analyzed using a similar procedure excluding the primary antibody. Images of the sections were captured with an Eclipse TI-E microscope fitted with a DSiQ2 digital camera combined with Nikon's NIS Elements imaging software (Nikon Instruments Inc.). At least 2 sections per mouse were examined for CD68 immunostaining.

For oil Red O staining of neutral lipids, sections were rehydrated in PBS for 5 min, fixed with 10% neutral buffered formalin for 5 min, extensively washed with water, and then treated with propylene glycol for 2 min. The sections were then stained with oil red O solution (0.5% in propylene glycol) for 15 min at 60° C. and extensively washed with water. After the oil red O staining procedure, the sections were counterstained with hematoxylin-eosin staining (Mayer's hematoxylin solution, Sigma). Images were captured with an Eclipse TI-E microscope and digital camera (Nikon), combined with Nikon's NIS Elements imaging software. To visualize cartilage glycosaminoglycans, sections were stained with Alcian blue 8GX (Sigma) at pH 2.5 (1% in 3% acetic acid).

After overnight fasting, blood was collected from mice by cardiac puncture under anesthesia with isoflurane. Serum was obtained through centrifugation of the blood for 15 min at 1,500 g at 4° C. and stored at −80° C. before analysis. Concentration of total cholesterol and triglycerides were measured using a colorimetric (MAK043, Sigma) and a fluorimetric assay (MAK266, Sigma), respectively. Total bile acids were assayed with a commercial enzyme-based colorimetric kit (Abcam Ab239702). Serum IL-6 and haptoglobin levels were determined using the commercially available ELISA kits (Fischer Scientific 10110623 and Abcam 157714, respectively). The alkaline phosphatase activity assay was performed in a 96-well plate. Briefly, sera were mixed with a concentrated buffer at a ratio of 2.85:1 (vol/vol) in order to get final concentration of 0.56 M 2-amino-2-methyl-1-propanol buffer pH 10.5, 1 mM $MgCl_2$ and 10 mM p-nitrophenylphosphate. Absorbance was acquired for 5 min at 405 nm (Tecan plate reader). The slope was calculated to determine TNAP activity levels in each sample and normalized to protein amounts measured with the BCA protein assay (Pierce).

3D microarchitecture of the distal metaphyseal femur and cortical midshaft were carried out using a Skyscan 1176 micro-CT scanner (Skyscan Inc.). The X-ray excitation voltage was set to 50 kV with a current of 500 mA. A 0.5 mm aluminum filter was used to reduce beam-hardening artifacts. Samples were scanned in 70% ethanol with a fixed voxel size of 9.08 μm. Section images were reconstructed with NRecon software (version 1.6.1.8, Skyscan). The region of interest (ROI) to delineate trabecular bone was drawn manually away from the endocortical surface, starting at 0.5 mm of underneath the growth plate and ending at 1.5 mm. For cortical analysis, 0.5 mm on either sides of the femur midshaft were reconstructed. The global threshold was set at 0.394 g HA/$cm^3$. Three-dimensional modeling and analysis of bone volume mineral density (BMD), tissue volume mineral density (TMD), bone volume to tissue volume ratio (BV/TV) were obtained with the CTAn (version 1.9) and CTVol (version 2.0) software.

For the determination of cholesterol, triglycerides, and total bile acids in liver, 40-mg pieces of liver were homogenized in 1 mL of 5% NP40 solution in a dounce homogenizer. The hydrophobic components were extracted twice at 80° C. for 5 minutes. The samples were centrifuged, and the supernatants were assayed for cholesterol, triglycerides and bile acids with the same kits used for blood. In order to quantify hydroxyproline, 100 mg pieces of liver were homogenized in 1 mL of pure water in a dounce homogenizer and a perchlorate-free kit from Sigma was used (MAK357).

Liver and kidney extraction and NMR measurement: The frozen tissues were weighed and then extracted using the methanol-chloroform-water system [2:2:1.425 (v/v/v)]. The upper methanol/water phase was collected, dried, lyophilized, and stored at −80° C. Deuterated phosphate buffer at pH=7.4 (200 mM) was added to the dried aqueous extract with sodium 2,2,3,3-tetradeutero-3-trimethylsilylpropionate (TSP) (Sigma-Aldrich) as internal chemical shift and quantification reference. $^1$H NMR spectra were recorded at 298 K on a Bruker Avance spectrometer 500 equipped with a 5-mm TCI cryoprobe. The ID pulse sequence (relaxation delay-pulse-acquisition) with pre-saturation for water (HOD) signal suppression was used. Acquisition parameters were as follow: relaxation delay 5.64 s, 30° pulse (4.5 μs) and acquisition time of 4.36 s. The spectral width of 15 ppm was used, and 256 scans were collected. With this repetition time of 10 s, the $^1$H resonances were fully relaxed. Data were processed using Bruker TopSpin software 3.2 with one level zero-filling and apodization (exponential, lb=0.3 Hz) before Fourier transform, then phase correction, simple baseline correction and calibration ($\delta_{TSP}$=0 ppm) were applied.

Chemometric analysis of NMR data: Data NMR matrix were obtained using facilities included in KnowItAll® (Wiley Science Solutions) and NMRProcFlow® software. First, the bucket list was obtained by the bin area method using the intelligent variable size bucketing tool included in the KnowItAll® package according to NMR signals assignment. Second, NMRProcFlow® pipeline was used for local baseline correction of spectra, alignment of NMR signals and integration of NMR area by that bucket list. Then, integrated regions were normalized by dividing their areas by that of the internal standard TSP and by the weight of tissue. Statistical analysis supervised Partial Least Squares-Discriminant Analysis (PLS-DA) and the nonparametric Wilcoxon test were carried out using the SIMCA-P+ 13.0.3 ((Sartorius, Aubagne, France) and Matlab® (Math Works, Natick, Massachusetts, USA) software.

$^1$H NMR absolute quantification of metabolites: Metabolites were assigned with an in-house metabolite database at pH=7.4. A total of 34 metabolites were identified and 30 could be quantified. Metabolites concentrations (ng/mg tissue) were given by $m_x = A_X/A_{TSP} \cdot 9/N_X \cdot 112 \cdot M_x/m_L$ with $A_X$ and $A_{TSP}$ being the areas of the signals of metabolite X and TSP, 9 and $N_X$ the number of protons of TSP and metabolite X evoking the signals, 112 the number of nmol of TSP in the solution analyzed, $M_x$ the molecular weight of metabolite X and m the weight (mg) of tissue analyzed.

Dephosphorylation of Phosphocholine and Phosphoethanolamine by Mouse and Human TNAP Analysis in human samples has been performed on healthy and diseased carotid arteries. Carotid plaques [n=101 calcified, and 14 non-calcified from the ECLAGEN biocollection] were removed by endarterectomy at the bifurcation from within the lumen as a single specimen. All samples were 1-2 cm long. For histology, sections of the lesion core present in each arterial sample were analyzed. Sample collection and handling were performed in accordance with our institutional medical ethics committee (research protocol #PFS09-014, n°DC-2008-402), and all patients participating in the study provided written informed consent. In the case of organ donors (healthy arteries), the absence of patient opposition to organ donation and an informed and signed consent was required from the patient's family. The arterial samples were fixed in 10% formalin for 48 h, decalcified in 4.13% EDTA-0.2% paraformaldehyde pH 7.4 over 4 days in KOS sw10 (Milestone), and embedded in paraffin. Following heat-induced epitope retrieval in EDTA pH 9, serial sections (4-μm thick) were stained with TNAP (Abcam), and Runx2 (Abcam) antibodies. Imaging of the sections was obtained with the NanoZoomer device (Hamamatsu Photonics).

Human coronary artery VSMCs (PromoCell) were grown in SMC growth medium 2 (SMC-GM2, PromoCell) supplemented with epidermal growth factor (0.5 ng/ml), insulin (5 μg/mL), basic fibroblast growth factor-β (2 ng/ml), and fetal bovine serum (5%) at 37° C. in humidified 5% $CO_2$. Cells were used between passages 3 and 9. Cells from 4-5 independent donors were used. VSMCs were cultured for up to 21 days in the presence of either control medium (DMEM, 10% FBS, 1% penicillin/streptomycin) or osteogenic medium (consisting of control medium supplemented with 10 nM dexamethasone, 10 mM β-glycerophosphate, and 100 μM L-ascorbate phosphate). The media were changed 3 times per week. *Mycoplasma* contamination test was routinely performed (once a month). TNAP activity was inhibited by the TNAP inhibitor MLS-0038949 (Merck, CAS 496014-13-2). TNAP activity was determined by the Alkaline Phosphatase Activity Colorimetric Assay Kit (BioVision, San Francisco, USA) according to manufacturer's instructions. TNAP activity was normalized to the protein amount. To visualize calcification, cells were washed and fixed with 4% paraformaldehyde for 10-15 min at room temperature. The mineralized matrix was visualized by 2% (w/v) Alizarin Red staining (Sigma Aldrich).

Mouse tissues: total RNAs were extracted from grinded abdominal aorta with the NucleoSpin RNA II kit (Macherey-Nagel) following the manufacturers' protocol. The quantity and quality of RNA were determined using a NanoDrop. RNA (1 μg) was retro-transcribed into cDNA with Superscript II reverse transcriptase (Life Technologies). PCR analysis was conducted using SYBR green Supermix (Biorad) on the iCycler Real-Time Detection system (Biorad). Fold change in mRNA expression was calculated using the $2^{-\Delta cq}$ method by the CFX Manager software (Biorad). Data were normalized by 3 housekeeping genes (HPRT, Actin and Rpl13a) levels.

Human VSMCs: total RNA was isolated using TriZol (Life Technologies) and mRNA levels were determined by TaqMan-based real-time PCR (Life Technologies). The following TaqMan probes were used: HS01047978_m1 (human Runx2), HS99999902_m1 (human Rplp0). The expression levels were normalized to Rplp0. Results were calculated using the ΔΔCt method and presented as fold increase relative to control.

Statistics

Data are expressed as the mean±SEM or SD, as indicated in the Figure legends. Statistical analyses were performed with Past 3.20 software. Data were tested on normality and on equal variances with Shapiro-Wilk test and Levene test respectively. Then, data were analyzed on appropriate parametric or nonparametric test, as indicated in the Figure legends. $P<0.05$ was considered significant.

Results

A. TNAP is Expressed in Close Proximity with Calcifications in Human Carotid Plaques, and its Inhibition in Cultured Human VSMCs Prevents Calcification.

Figure 7A:
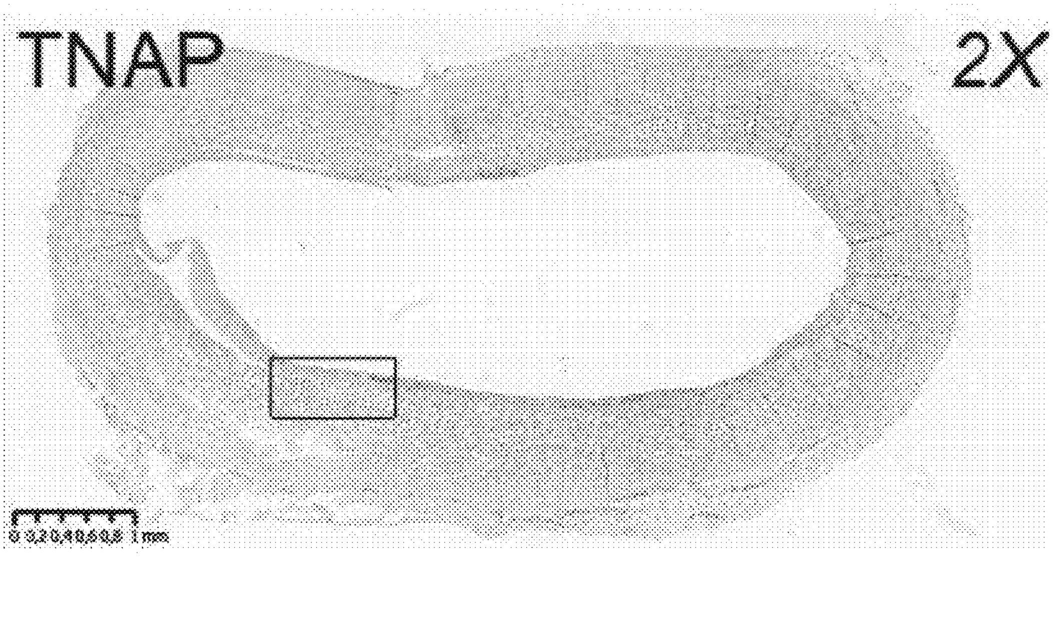
FIGS. 7A-7D are representative IHC staining of TNAP and RUNX2 in a healthy human carotid with no plaque. On the left, low-magnification (2×) photographs, the bar indicates 1 mm; on the high-magnification images (15×), the bar indicates 100 μm.
Figure 7B:
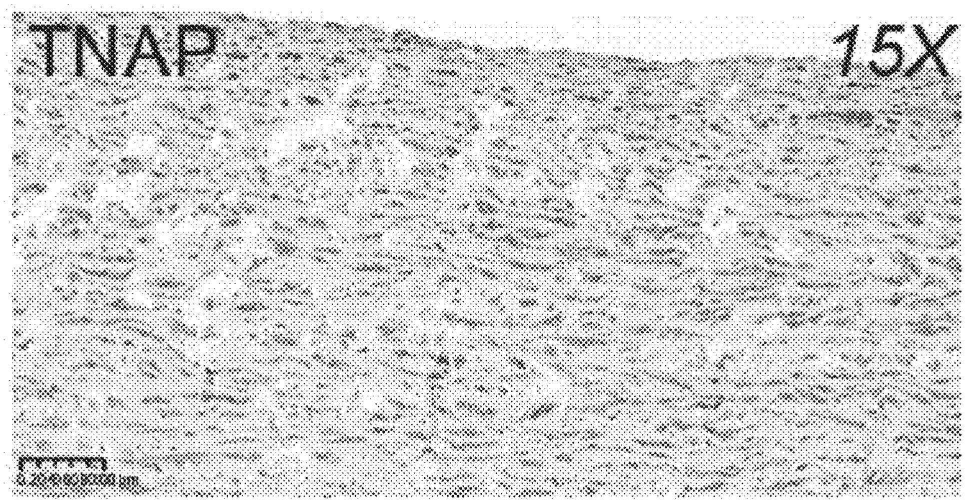
Figure 7C:
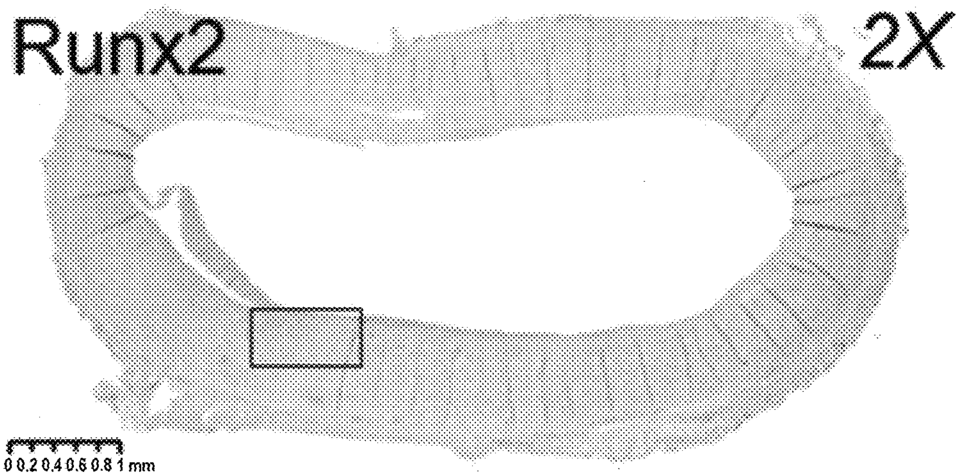
Figure 7D:
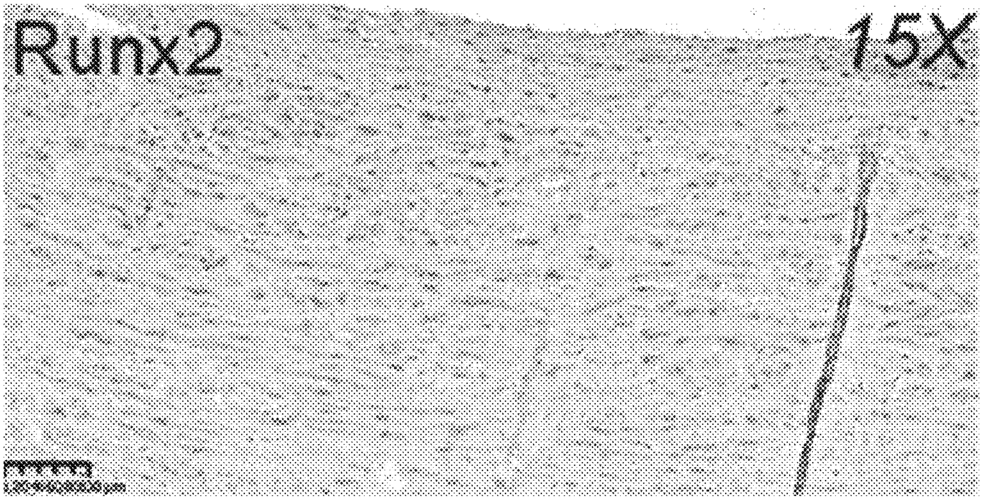
Figure 7E:
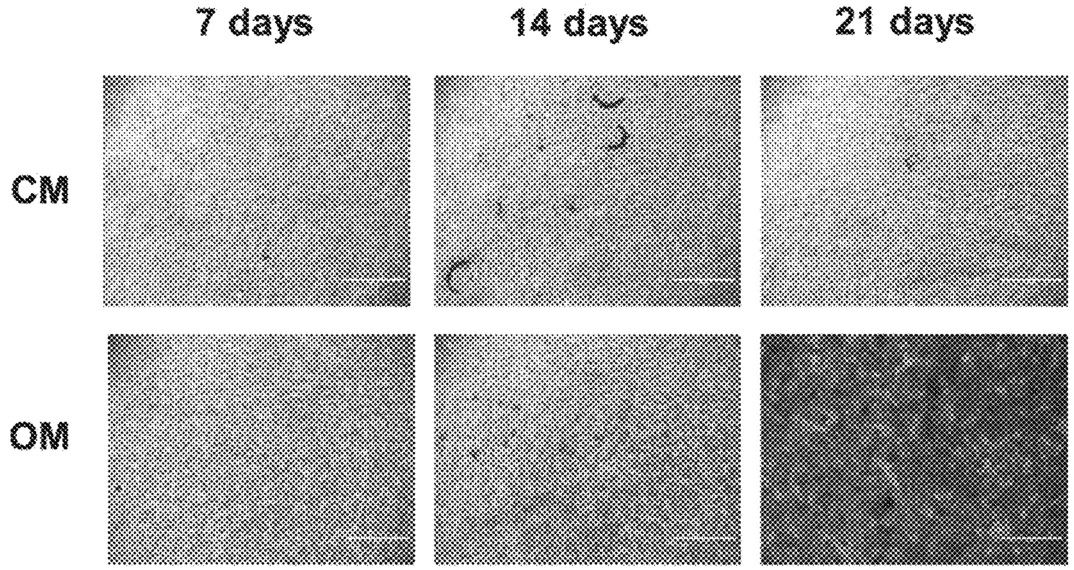
FIG. 7E illustrates alizarin red staining of calcium deposits in representative cultures of human VSMCs grown in CM or OM for 7, 14 or 21 days.
Figure 7F:
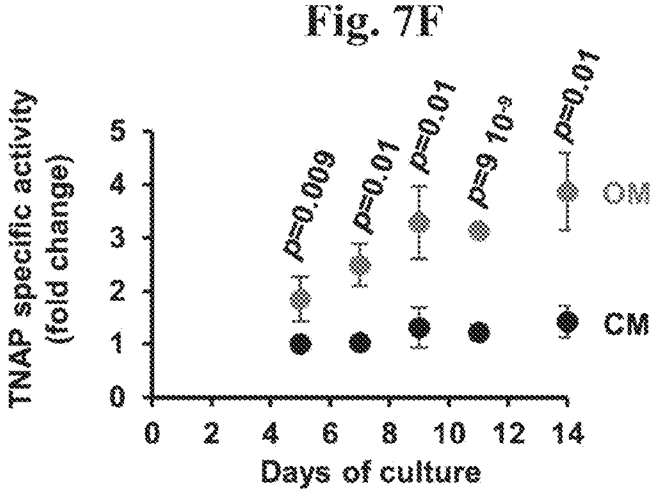
FIG. 7F illustrates evolution during time of TNAP activity in human VSMCs cultured in CM or OM.
Figure 7G:
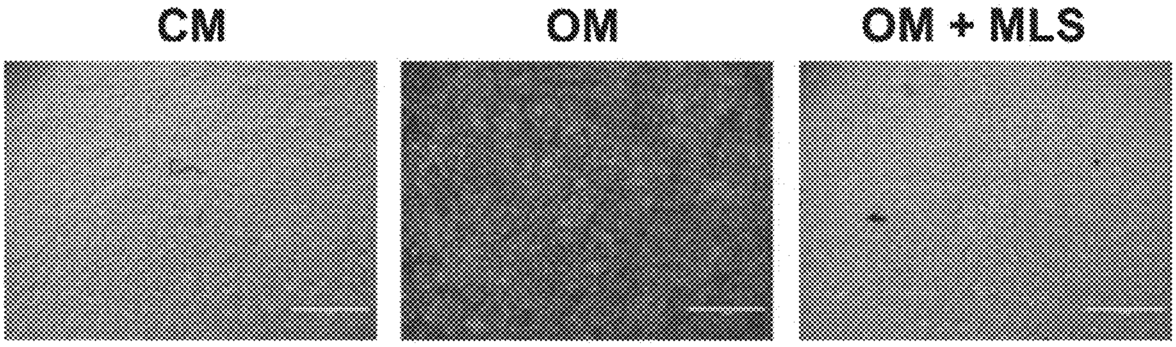
FIGS. 7G-7I) Effect of MLS-0038949 on calcification (FIG. 7G), TNAP activity (FIG. 7H), and RUNX2 transcript levels (FIG. 7I) at 21 weeks. Results are shown as mean±standard deviation, and statistical analyses were performed with Mann-Whitney U test. CM: control medium; IHC: immunohistochemistry; MLS: MLS-0038949; OM: osteogenic medium; VSMC: vascular smooth muscle cell.
Figure 7H:
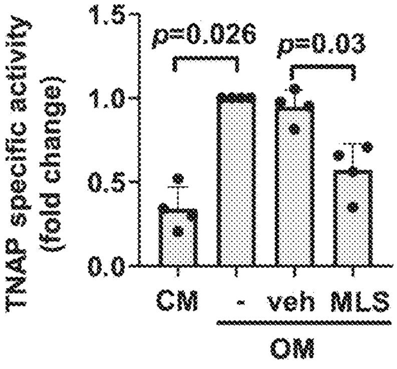
Figure 7I:
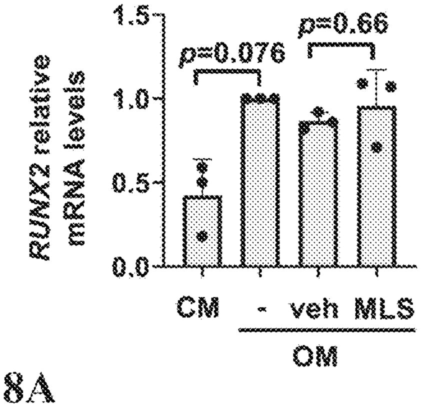

Plaque calcification proceeds through distinct mechanisms in mice and humans. While it relies on endochondral ossification in ApoE-deficient mice, in humans it often occurs through intramembranous ossification in peripheral arteries and more rarely in carotids or coronaries. To avoid obtaining results and drawing conclusions that may only be true in mice but not in humans, in this experiment, it was explored whether carotid plaque calcification in humans may rely on TNAP. To this purpose, a biocollection of human carotid plaques in which the calcification morphology (microcalcifications, calcium nodules, sheet-like calcifications and osteoid metaplasia) has been characterized was used. In these lesions and independently of the calcification type, TNAP was consistently expressed at the proximal periphery of calcifications (FIGS. 1A-1F). Interestingly, even when signs of bone-like structures or ossification were not observed, TNAP was often coexpressed with RUNX2, the master transcription factor governing osteoblast and hypertrophic chondrocyte differentiation. These data suggested that even in human plaques that did not show features of ossification or presence of bone-like cells, calcification relied on TNAP expressed under the control of RUNX2, presumably in trans-differentiated cells. Moreover, TNAP may be active before calcification formed because RUNX2 and TNAP coexpression in plaque regions with no calcifications was observed (FIGS. 1A-1F) and also in carotids with no plaques (FIGS. 7A-7D). Calcification relied probably at least in part on TNAP in these human plaques because when cultured human VSMCs were stimulated by an osteogenic medium to express RUNX2 (FIGS. 7E and 7G), TNAP inhibition totally prevented calcification (FIGS. 7G-7I). The ex vivo and in vitro data in humans encouraged us to determine the in vivo effects of TNAP inhibition in atherosclerotic mice.

B. TNAP is Expressed in Close Proximity with Calcifications in Mouse Plaques, and its Inhibition Prevents Plaque Calcification and Decreases Plaque Inflammation.

Figure 2A:
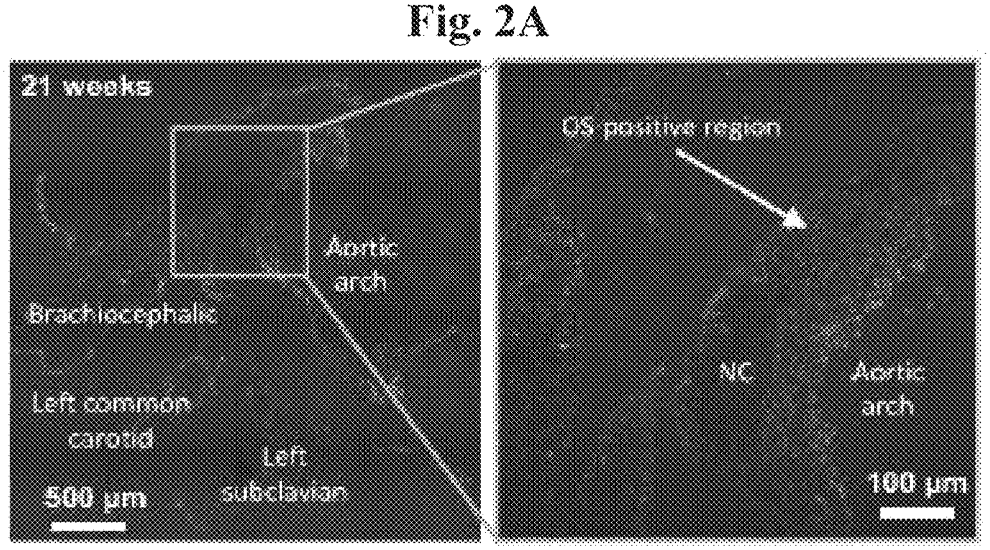
FIGS. 2A-2C illustrate histological analyses of calcification after osteosense (OS) staining in ApoE-deficient mice at 21 weeks (FIG. 2A), 25 weeks (FIG. 2B) and 31 weeks (FIG. 2C).
Figure 2B:
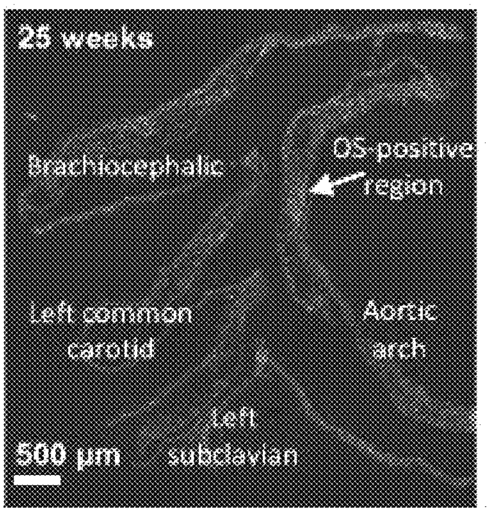
Figure 2C:
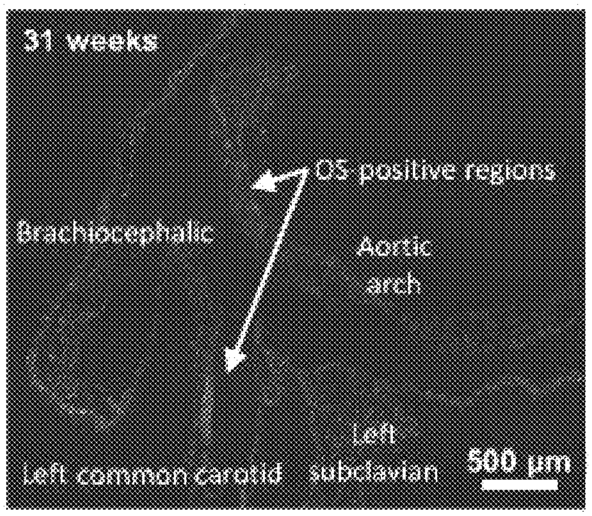
Figure 2D:
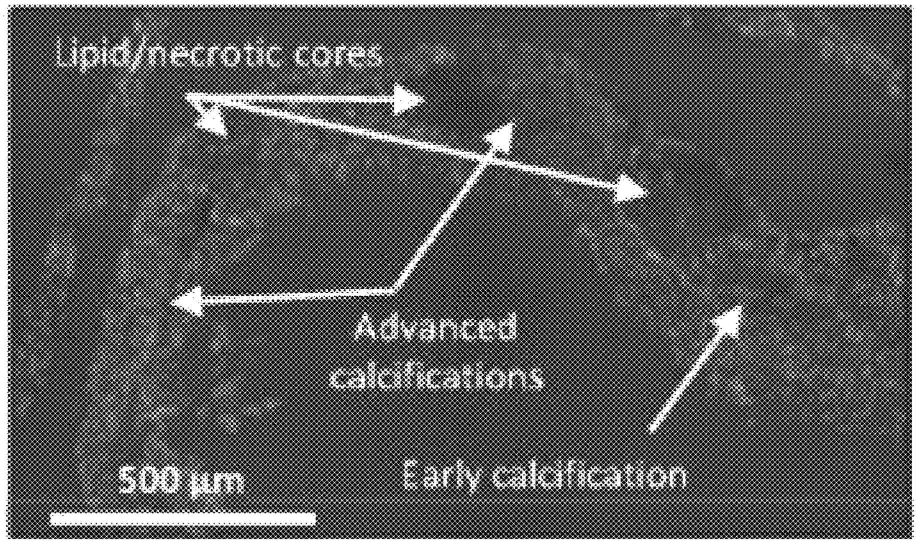
FIGS. 2D-2I illustrate aortic arch plaques partly (FIGS. 2D, 2F, and 2H) or totally (FIGS. 2E, 2G, and 2I) calcified in 25-week-old mice as imaged by OS (FIGS. 2D and 2E), alcian blue (FIGS. 2F and 2G), and oil red O (FIGS. 2H and 2I).
Figure 2E:
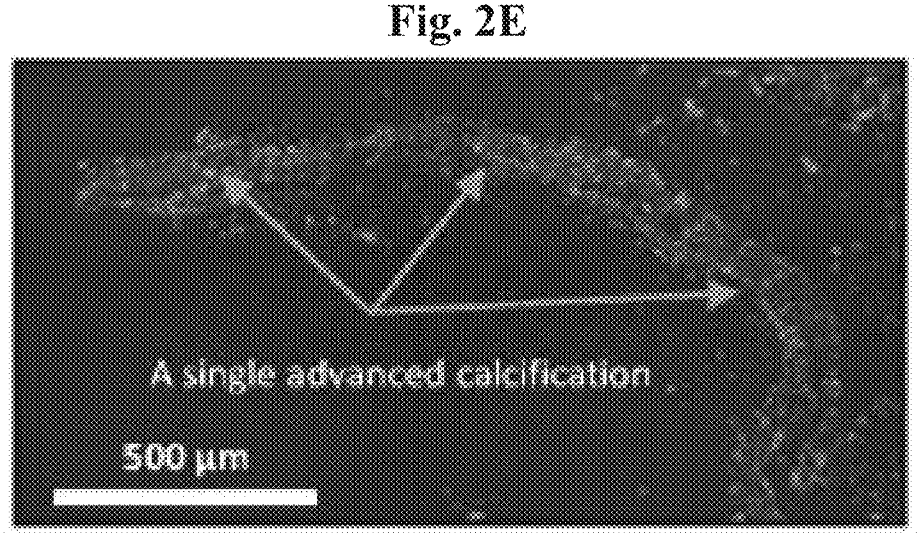
Figure 2F:
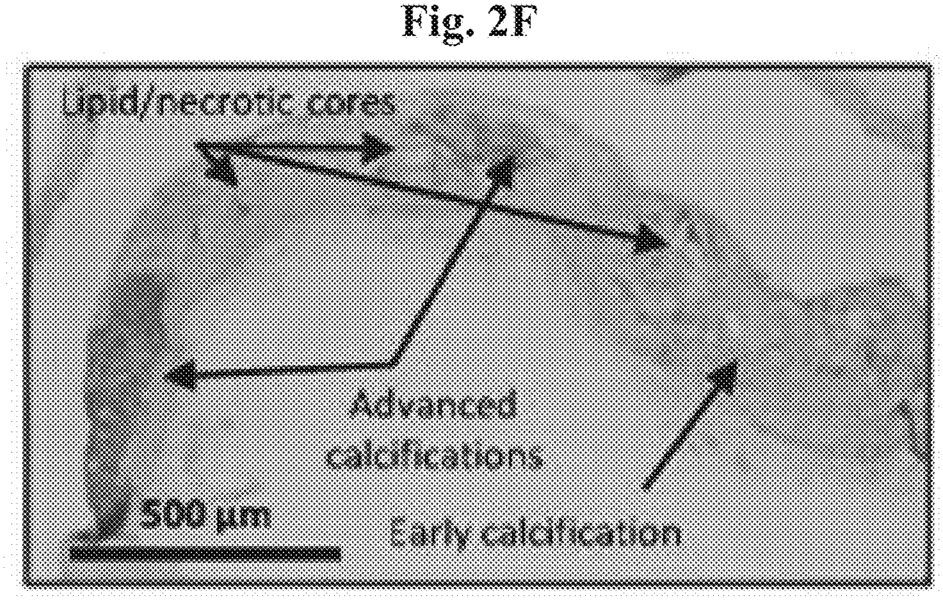
Figure 2G:
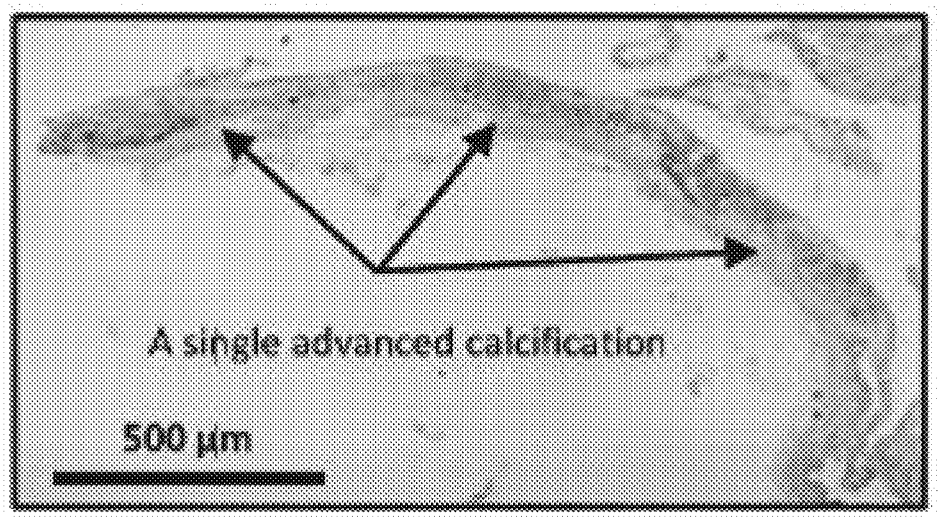
Figure 2H:
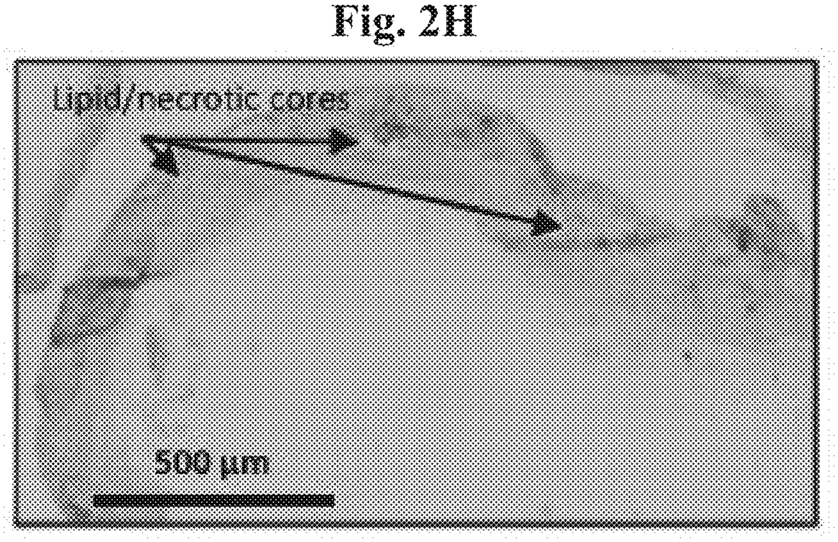
Figure 2I:
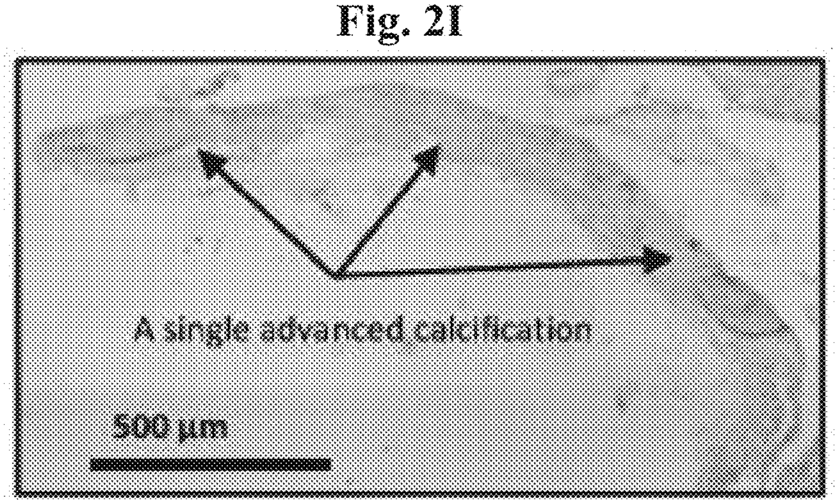
Figure 2J:
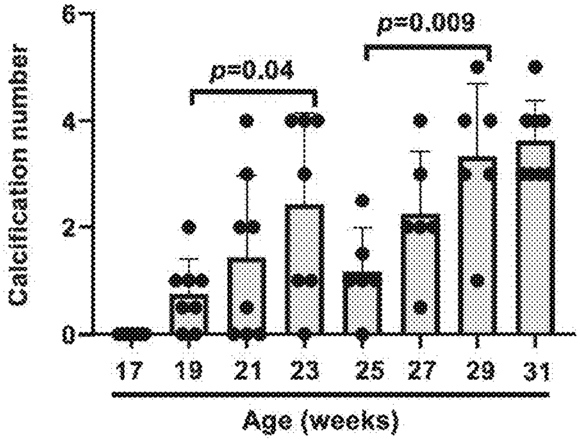
FIGS. 2J and 2K illustrate quantification of calcification number (FIG. 2J) and surface (FIG. 2K) after OS staining at 17 (n=8), 19 (n=8), 21 (n=8), 23 (n=8), 25 (n=6), 27 (n=6), 29 (n=6) and 31 weeks (n=8).
Figure 2K:
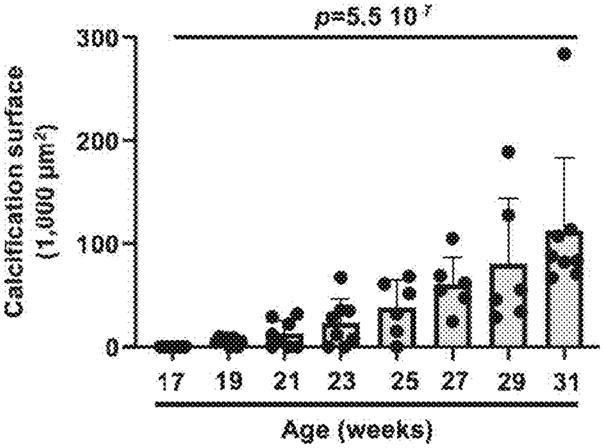
Figure 2L:
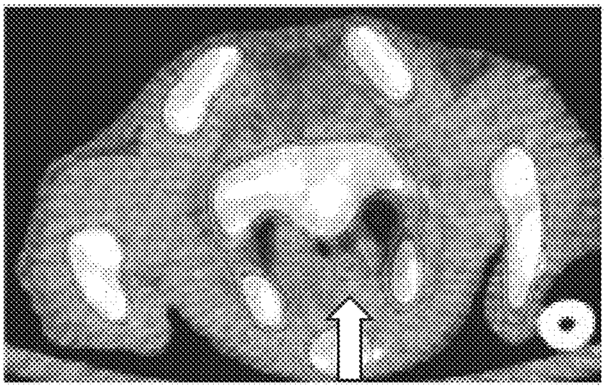
FIGS. 2L-2N illustrate representative in vivo imaging with $^{18}F$—NaF μPET/μCT of aortic calcification (red arrow) in a 34-week-old mouse (FIGS. 2L and 2M) and its quantification by μCT and $^{18}F$—NaF μPET (FIG. 2N).
Figure 2M:
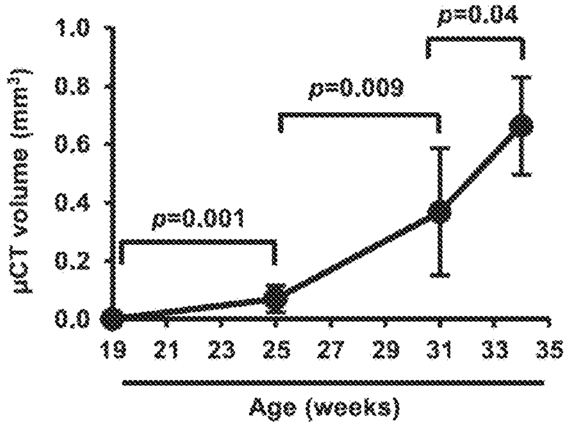
Figure 2N:
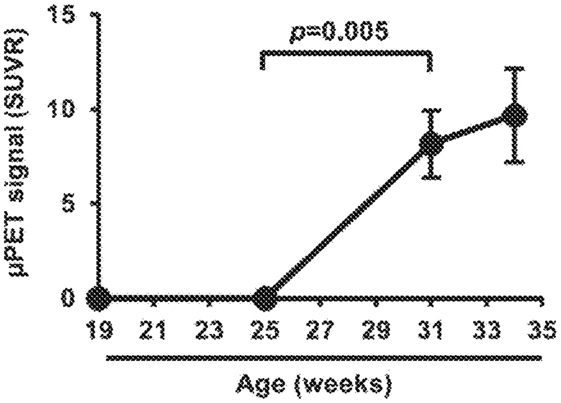
Figure 2O:
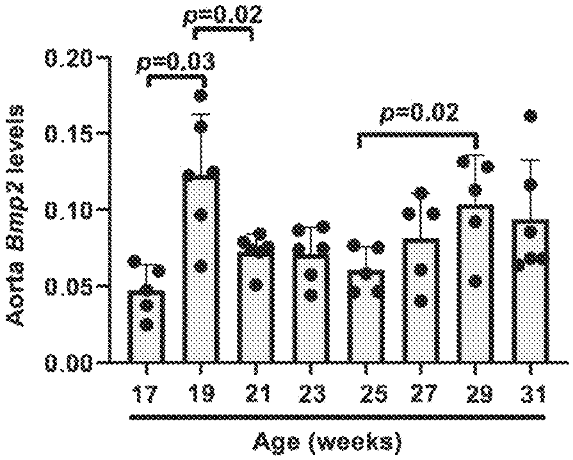
FIGS. 2O-2S show quantitative PCR determination of relative transcript levels in the abdominal aorta in ApoE-deficient mice at 17 (n=5), 19 (n=6), 21 (n=6), 23 (n=6), 25 (n=6), 27 (n=5), 29 (n=5) and 31 weeks (n=6).
Figure 2P:
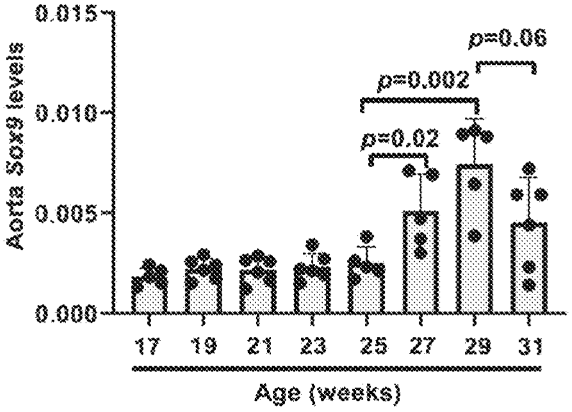
Figure 2Q:
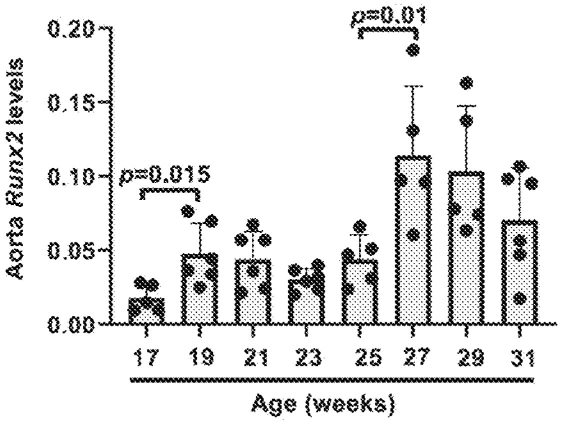
Figure 2R:
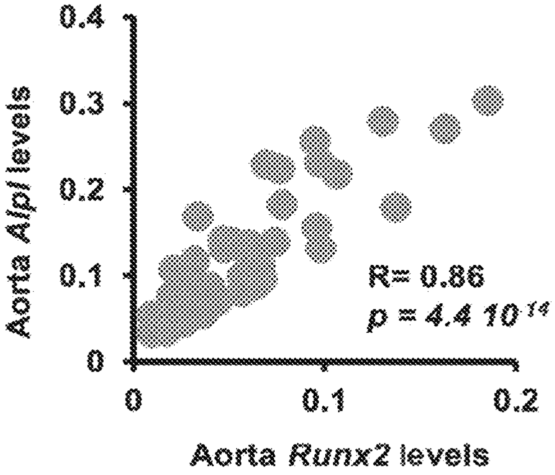
Figure 2S:
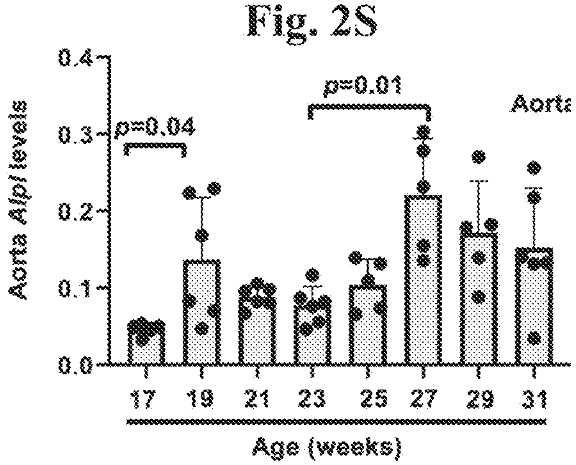
Figure 2T:
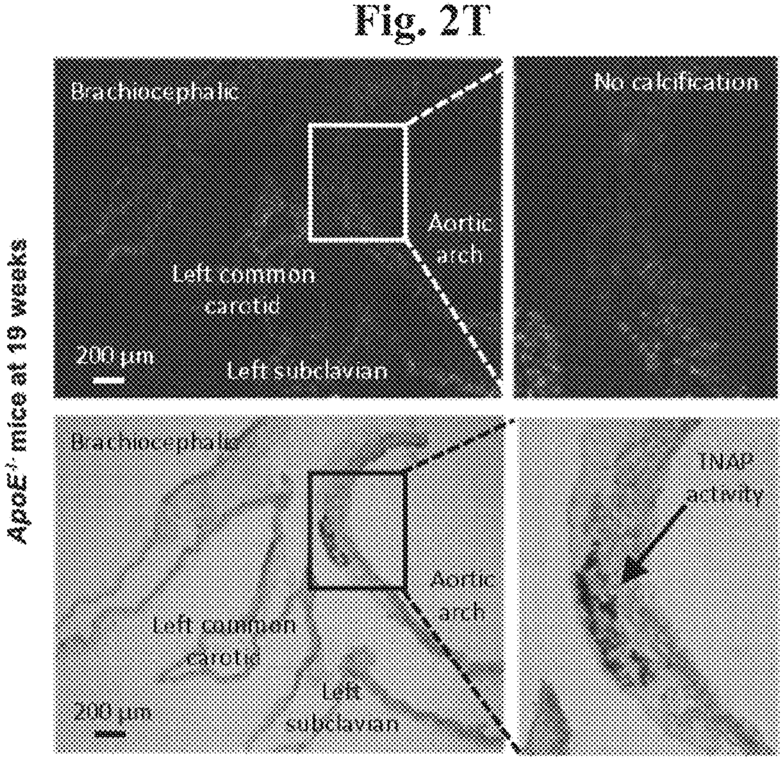
FIGS. 2T and 2U illustrate a correlation between Alp1 and Runx2 levels from 17 to 31 weeks as calculated with Pearson's test. OS staining and TNAP activity staining at 19 weeks (FIG. 2T) and 21 weeks (FIG. 2U). All quantitative results are shown as mean±standard deviation, and statistical analyses were performed with one way ANOVA (FIG. 2K) and student's t-test (FIGS. 2J, 2K-2M, 2O-2Q, 2R, and 2S). CT: computed tomography; NC: necrotic core; OS: osteosense; PET: positron emission tomography; SUVR: standardized uptake value ratio.
Figure 2U:
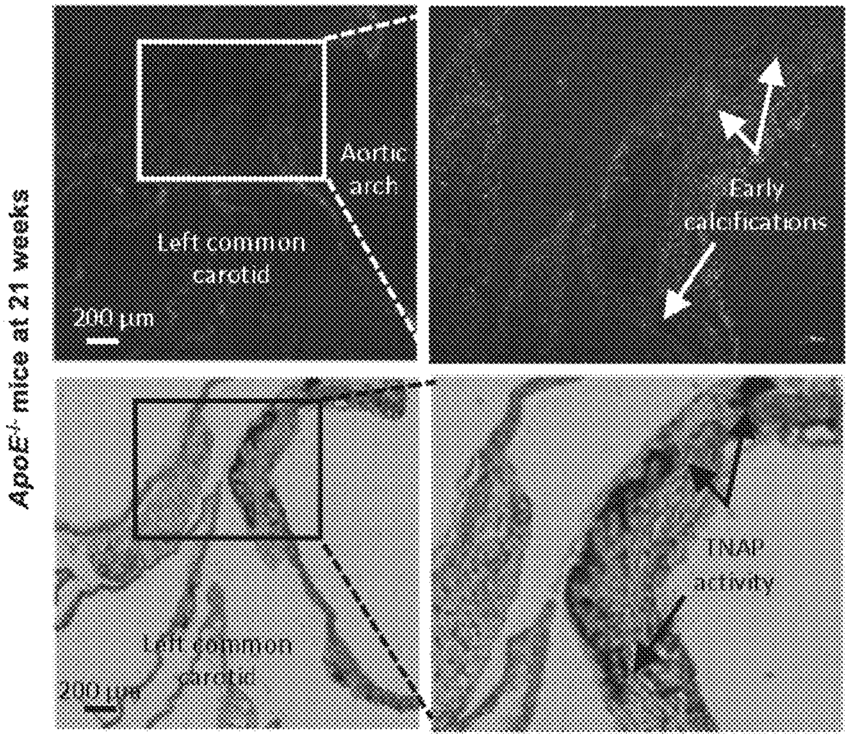
Figure 8B:
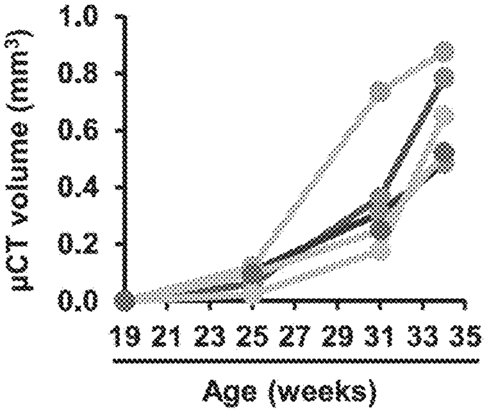
FIG. 8B illustrates in vivo quantification of calcification with μCT and FIG. 8C $^{18}F$—NaF μPET (each line represents a mouse).
Figure 8C:
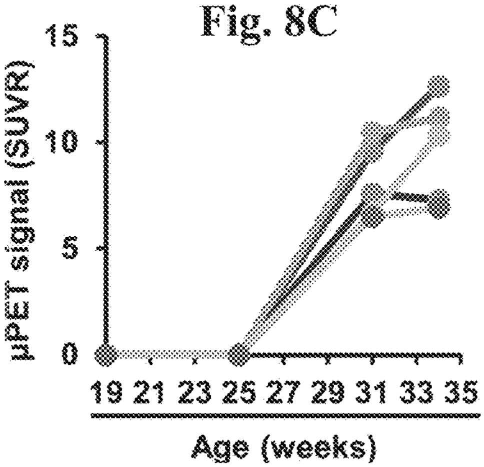
FIGS. 8D-8H illustrate quantitative RT-qPCR determination of relative transcript levels in the abdominal aorta in ApoE-deficient mice at 17 (n=5), 19 (n=6), 21 (n=6), 23 (n=6), 25 (n=6), 27 (n=5), 29 (n=5) and 31 weeks (n=6). CT: computed tomography; HFD: high fat diet; PET: positron emission tomography; SUVR: standardized uptake value ratio.
Figure 8D:
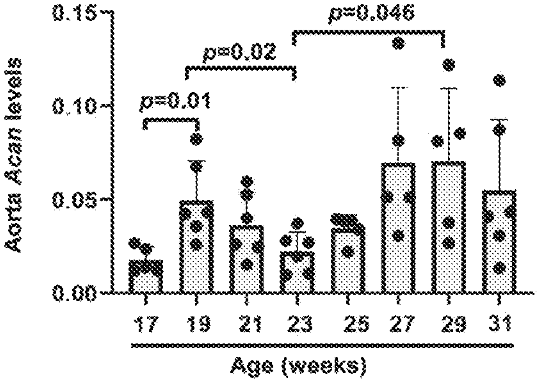
Figure 8E:
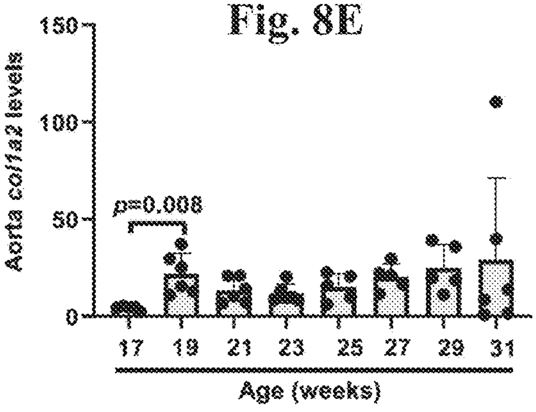

In order to determine when TNAP inhibition should be initiated and stopped in ApoE-deficient mice, the time-course of atherosclerotic plaque development in animals sacrificed every two weeks from 17 to 31 weeks of age in cohort 1 was characterized thoroughly, ex vivo analyses were conducted, and in animals, $^{18}$F—NaF μPET/μCT at 19, 25, 31 and 34 weeks in cohort 2 were imaged in vivo (FIG. 8A). Osteosense (OS)-based imaging detected calcifications (≈10 μm in size) from 19-21 weeks of age (FIG. 2A). Early calcifications were first spotted in the aortic arch (FIGS. 2A and 2B) and were followed by calcifications in other arteries, such as the left common carotid (FIG. 2C). Calcifications initially developed in or near necrotic and lipid cores, after which they progressed into cartilaginous metaplasia (FIGS. 2D-2I). In some mice, they eventually merged to occupy the whole aortic arch, which was then totally devoid of necrotic cells and lipids (FIGS. 2D-2I). The number of calcifications logically increased from 17 to 23 weeks; it stopped increasing or even decreased at 25 weeks because of the merging of calcifications in the aortic arch and increased again at 27 weeks when calcifications began to form in other arteries (FIG. 2J). The total surface of calcifications determined ex vivo by histology (FIG. 2K) and the total volume of calcifications determined in vivo by μCT (FIGS. 2L, 2M, and 8B) increased similarly and relatively regularly. In contrast, the calcification activity measured in vivo with $^{18}$F—NaF μPET revealed that calcification slowed down at 31 weeks of age (FIGS. 2N and 8C). This slowdown was concomitant with the stagnation of chondrocyte transcript levels between 27 and 31 weeks, after these transcripts had increased in two waves, the first at 19 weeks, and the second at 27 weeks (FIGS. 2O-2Q and 8D). The transcript levels of Alpl encoding TNAP were highly associated with those of Runx2 (FIGS. 2R and 2S), suggesting that TNAP was almost exclusively produced by VSMCs trans-differentiated into hypertrophic chondrocytes. Finally, it was considered extremely likely that TNAP was locally involved in plaque calcification since TNAP activity was detected in plaques before calcification could be detected and because when calcifications were present, they were consistently observed in close proximity with TNAP activity (FIGS. 2T and 2U). Collectively, these ex vivo data suggested that calcification was not linear but developed within two waves: a first one at 19 weeks, likely associated with aortic arch calcification, and a second one at 27 weeks, associated with the onset of calcification in other arteries. In this context, it was decided to choose to initiate TNAP inhibition from 10 weeks of age in a preventive manner, by administration of 30 mg/kg/day of SBI-425 admixed in the HFD and to stop the treatment at 25 weeks, after the first wave of calcification (FIG. 9A).

Figure 3A:
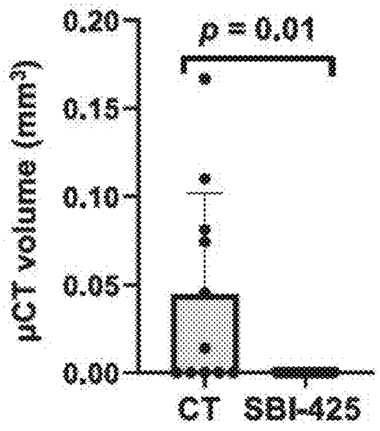
FIGS. 3A-3V illustrate in vivo quantification of calcification volume measured by μCT (FIG. 3A) and of calcification activity, as measured with $^{18}F$—NaF μPET (FIG. 3B) (n=11 CT mice and n=12 SBI-425 treated mice).
Figure 3B:
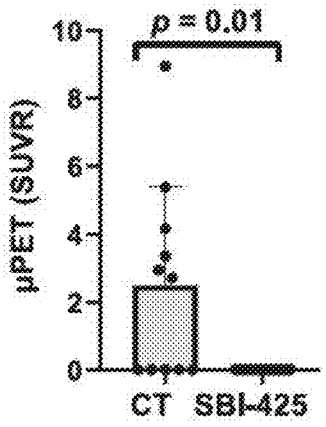
Figure 3C:
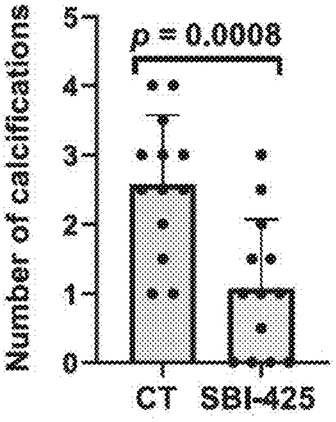
FIGS. 3C-3E illustrate histological quantification of calcification number and surface after OS staining (FIGS. 3C and 3D), and of plaque surface (FIG. 3E) and lipid surface (FIG. 3F) after oil red O staining.
Figure 3D:
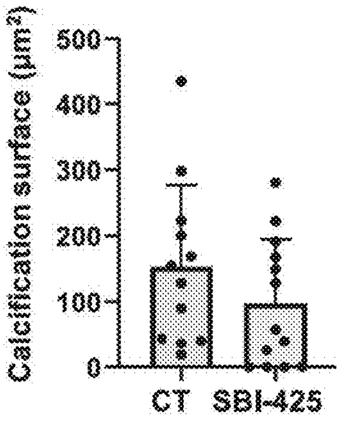
Figure 3E:
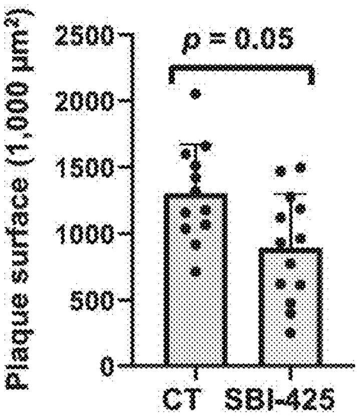
Figure 3F:
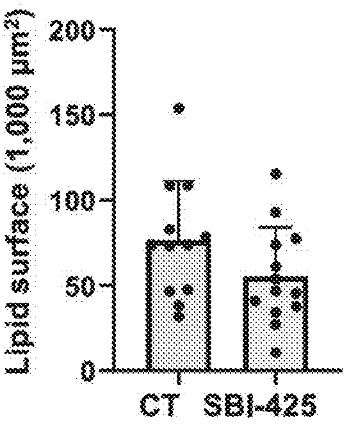
Figure 3G:
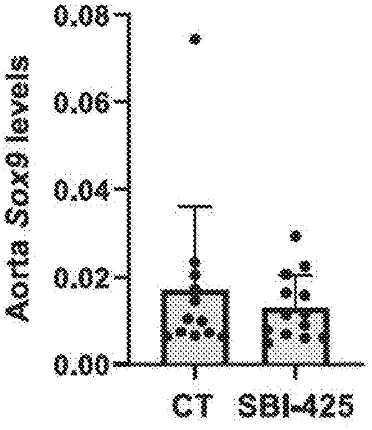
FIGS. 3G-3Q illustrate quantitative PCR determination of relative transcript levels in the abdominal aorta in ApoE-deficient mice (n=12 CT mice and n=13 SBI-treated mice).
Figure 3H:
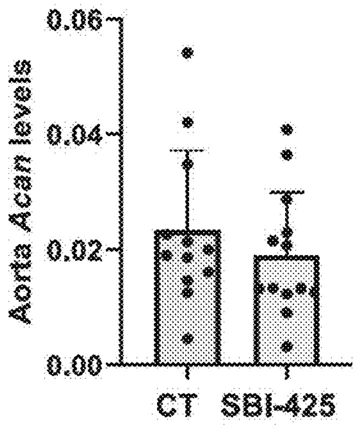
Figure 3I:
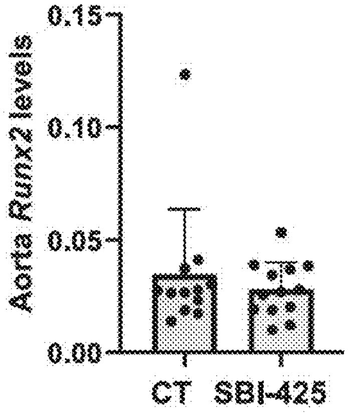
Figure 3J:
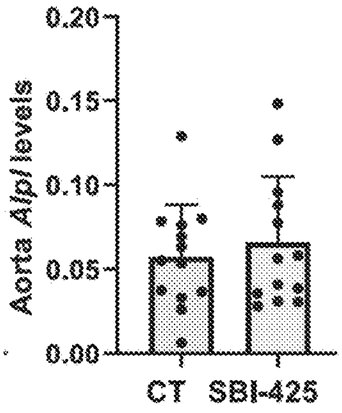
Figure 3K:
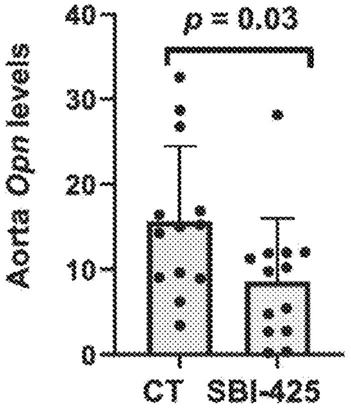
Figure 3L:
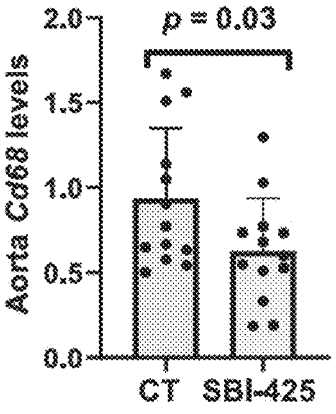
Figure 3M:
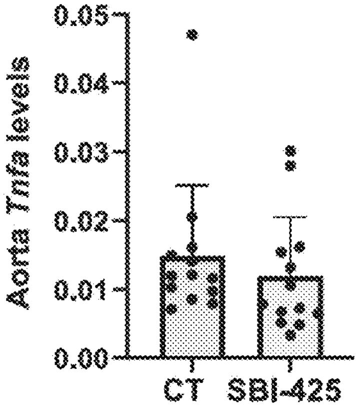
Figure 3N:
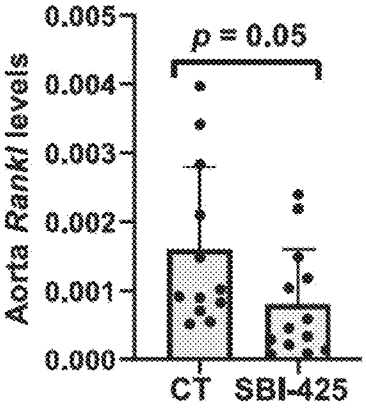
Figure 3O:
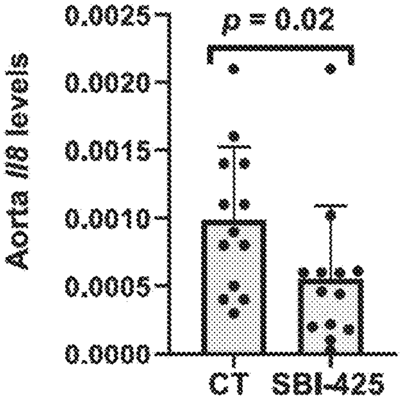
Figure 3P:
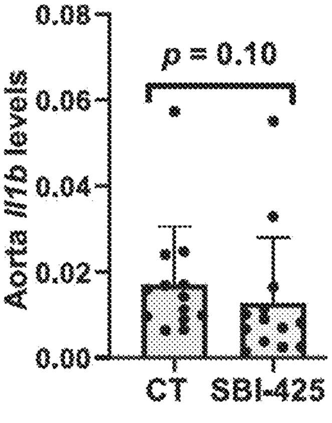
Figure 3Q:
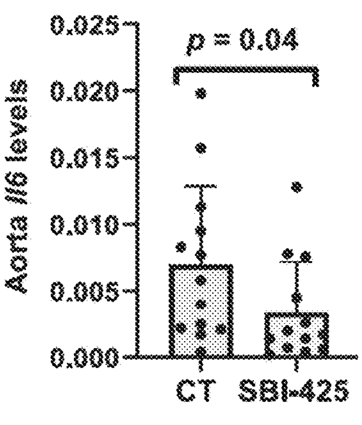
Figure 3R:
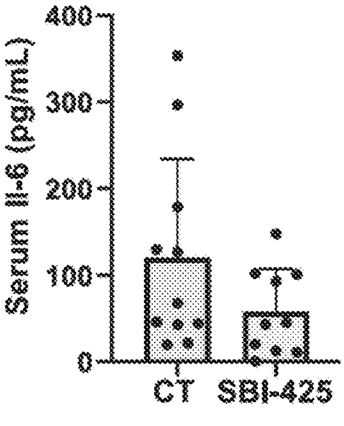
FIG. 3R illustrates a determination of serum IL-6 levels (n=11 CT mice and n=10 SBI-treated mice).
Figure 3S:
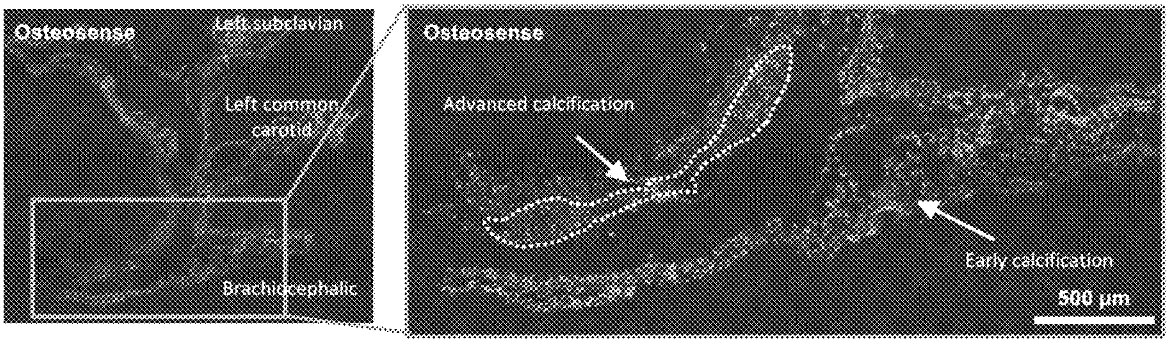
FIG. 3S illustrates OS staining and CD68 IHC in a representative mouse.
Figure 3T:
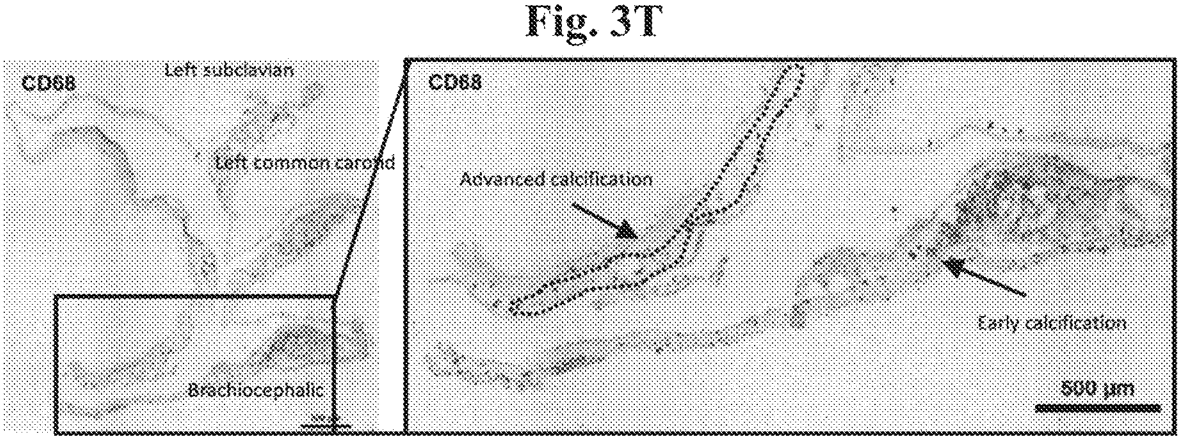
Figure 3U:
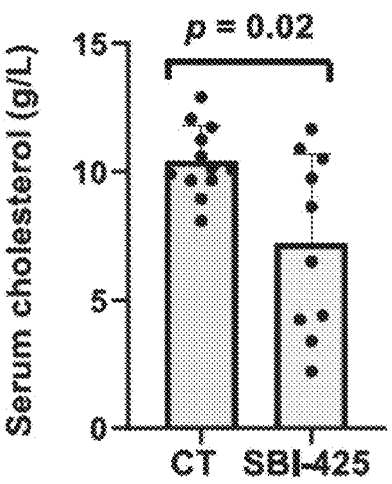
Figure 3V:
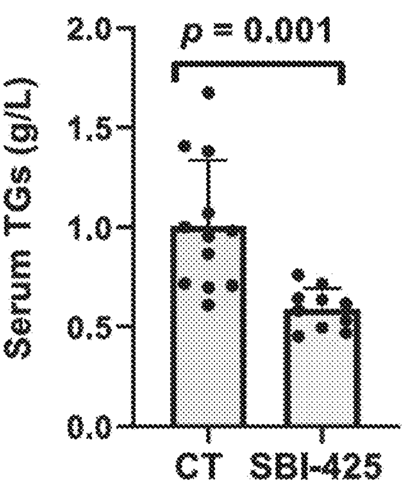
Figure 8F:
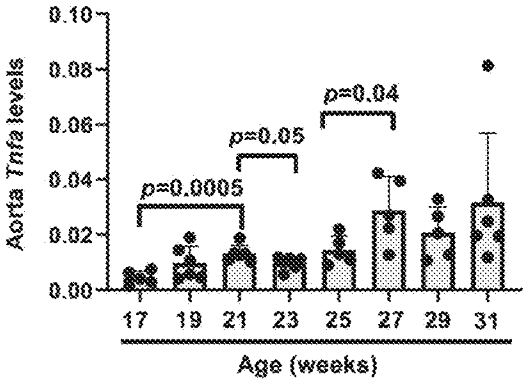
Figure 8G:
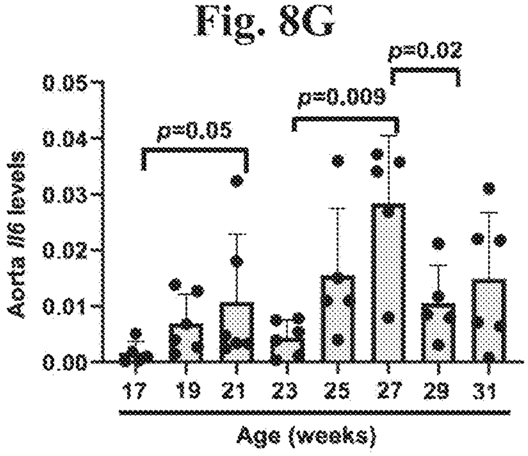
Figure 8H:
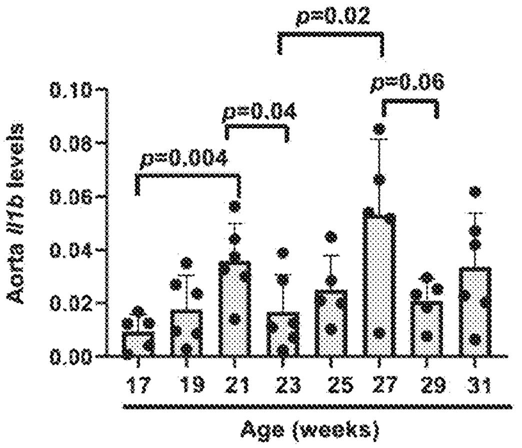

TNAP inhibition was apparently well-tolerated, with no effect on mortality, body weight, or bone architecture even when the treatment was prolonged for 21 weeks (FIGS. 9B-9H). As hypothesized, TNAP inhibition prevented plaque calcification, with 0 out of 12 mice having calcifications in the SBI-425 group, against 6 out of 11 in the control group as determined in vivo with $^{18}$F—NaF μPET (FIG. 3A) and μCT (FIG. 3B). By histology, which proved more sensitive in detecting early calcifications than $^{18}$F—NaF μPET and μCT (FIGS. 2A-2U), it was observed that while 13 out of 13 mice developed calcifications in the control group, only 9 out of 13 mice formed calcifications in the SBI-425 group (FIGS. 3C and 3D). Moreover, even when SBI-425-treated mice developed calcifications, the number of calcifications per mice was lower. Upon SBI-425 treatment, plaques were smaller (FIG. 3E) and contained less lipids (FIG. 3F). Prevention of calcification by SBI-425 administration was apparently not accompanied by reduced levels of chondrocyte markers (Sox9, Acan, Runx2, or Alpl) (FIGS. 3G-3Q). In contrast, SBI-425 significantly decreased the levels of the inflammatory markers Opn, Cd68, Rankl, Il8 and Il6 levels (FIGS. 3G-3Q) and reduced serum IL-6 levels, although not significantly (FIG. 3R). Prevention of new calcifications and decreased inflammation were likely two intimately associated effects, because in both treated and untreated mice, small calcifications, but not advanced macrocalcifications, were consistently observed in plaque regions enriched in CD68-positive macrophages (FIGS. 3S and 3T). Collectively, these data suggested that TNAP inhibition exerted beneficial effects on plaque calcification and inflammation. It was found that TNAP inhibition significantly decreased the serum levels of cholesterol and triglycerides (TGs) (FIG. 3R). This suggested that SBI-425 might also have impacted plaque development by inhibiting liver TNAP.

lar waves of inflammatory markers (FIGS. 8F-8H). Furthermore, calcification activity (but not calcium volume) was positively associated with both inflammatory and chondrocyte markers (Table 2). Then, after establishing liver TNAP expression and liver disease in relation with plaque development, whether SBI-425 administration impacted liver inflammation, steatosis and/or fibrosis, was investigated to explain how it might have decreased serum lipids and impaired atherosclerotic plaque development.

TABLE 2

Correlations Calculated with Pearson's Test (Results are shown as mean ± standard deviation, and statistical analyses were performed with student's t-test.)

| | µCT | Sox9 | Col2al | Acan | Tnfa | Il6 | Il1b |
|---|---|---|---|---|---|---|---|
| µPET | R = −0.57<br>ρ = 0.32 | R = 0.68<br>ρ = 0.2 | R = 0.97<br>ρ = 0.007 | R = 0.86<br>ρ = 0.06 | R = 0.96<br>ρ = 0.009 | R = 0.93<br>ρ = 0.02 | R = 0.85<br>ρ = 0.07 |
| µCT | — | R = 0.21<br>ρ = 0.73 | R = −0.51<br>ρ = 0.37 | R = −0.39<br>ρ = 0.52 | R = −0.51<br>ρ = 0.38 | R = −0.32<br>ρ = 0.59 | R = −0.33<br>ρ = 0.58 |
| Sox9 | R = 0.21<br>ρ = 0.73 | — | R = 0.67<br>ρ = 0.07 | R = 0.65<br>ρ = 0.08 | R = 0.61<br>ρ = 0.11 | R = 0.73<br>ρ = 0.04 | R = 0.58<br>ρ = 0.13 |
| Col2a1 | R = −0.51<br>ρ = 0.37 | R = 0.67<br>ρ = 0.007 | — | R = 0.88<br>ρ = 0.003 | R = 0.98<br>ρ = $3 \times 10^{-5}$ | R = 0.95<br>ρ = $3 \times 10^{-4}$ | R = 0.87<br>ρ = 0.005 |
| Acan | R = −0.39<br>ρ = 0.51 | R = 0.65<br>ρ = 0.08 | R = 0.88<br>ρ = 0.003 | — | R = 0.91<br>ρ = 0.001 | R = 0.93<br>ρ = 0.001 | R = 0.92<br>ρ = 0.001 |

C. TNAP Expression Increases in the Liver of ApoE-Deficient Mice During Non-Alcoholic Steatohepatitis (NASH).

Figure 4A:
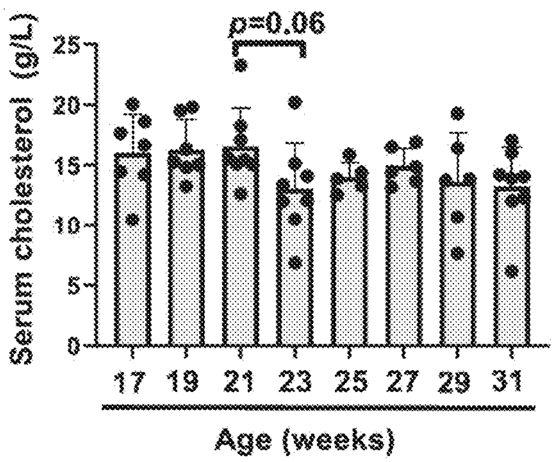
FIGS. 4A, 4D, 4J, 4K, and 4O illustrate quantification in the serum of ApoE-deficient mice of cholesterol levels (FIG. 4A), TG levels (FIG. 4D), haptoglobin levels (FIG. 4J), glucose levels (FIG. 4K), or TNAP activity (FIG. 4O).
Figure 4B:
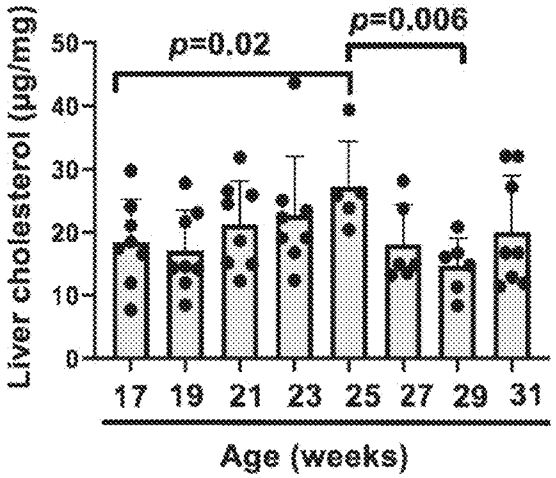
Figure 4C:
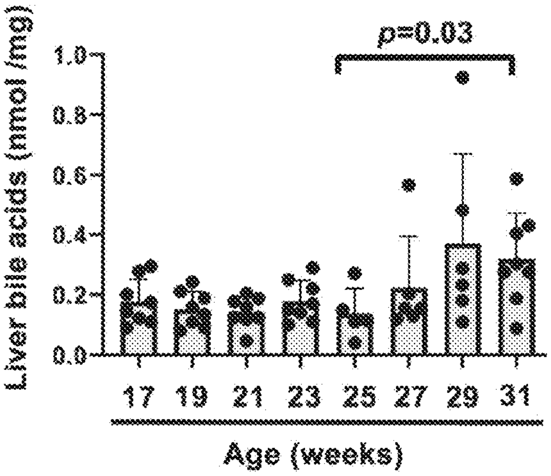
Figure 4D:
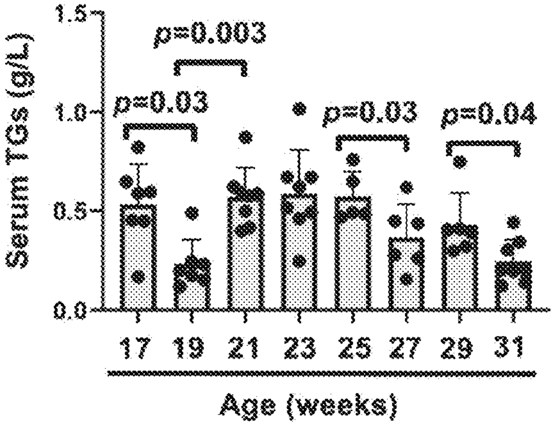
Figure 4E:
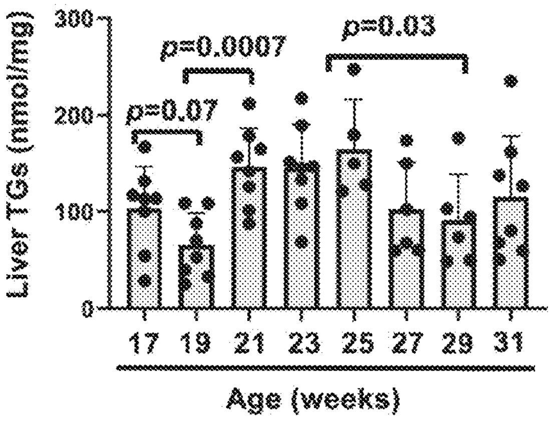
Figure 4F:
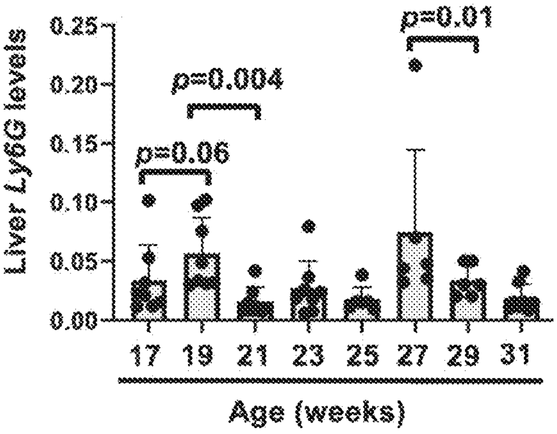
FIGS. 4F-4I and 4L-4N illustrate RT-qPCR determination of relative transcript levels in the liver of ApoE-deficient mice. Results are shown as mean±standard deviation, and statistical analyses were performed with student's t-test at 17 (n=5), 19 (n=6), 21 (n=6), 23 (n=6), 25 (n=6), 27 (n=5), 29 (n=5) and 31 weeks (n=6).
Figure 4G:
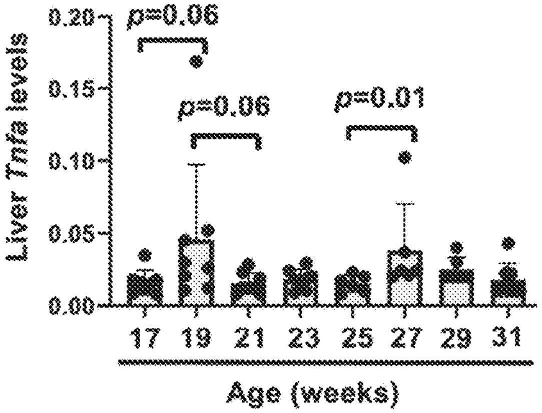
Figure 4H:
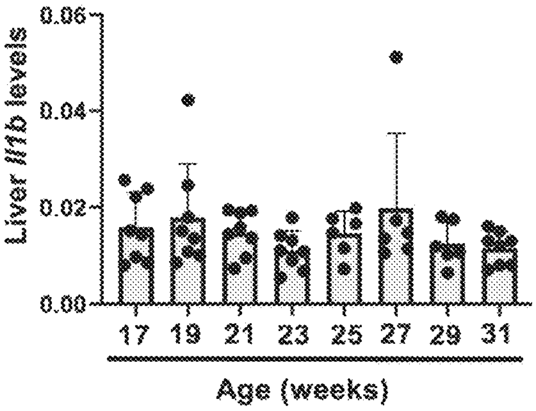
Figure 4I:
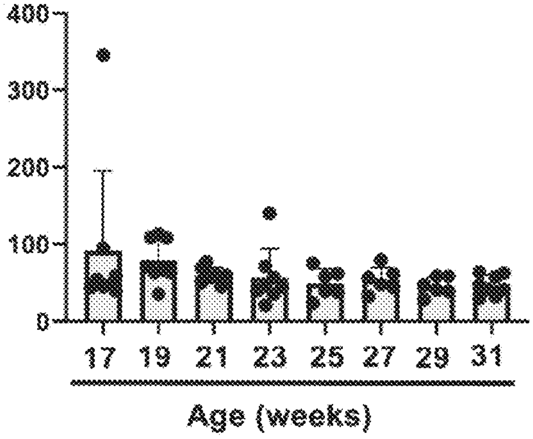
Figure 4J:
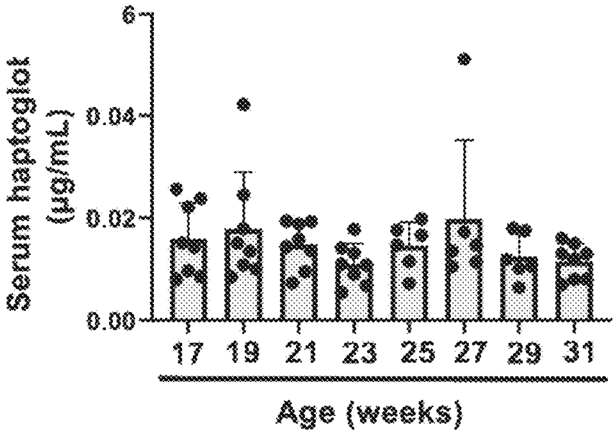
Figure 4K:
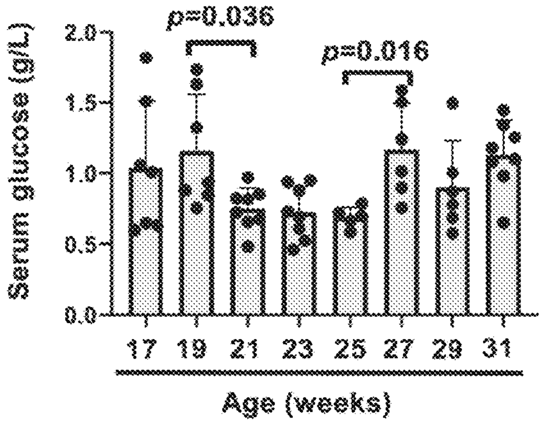
Figure 4L:
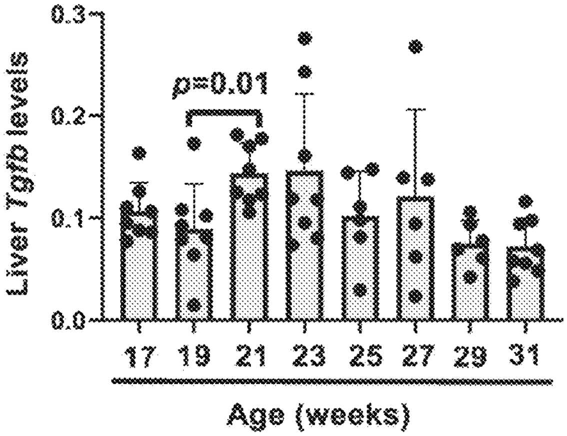
Figure 4M:
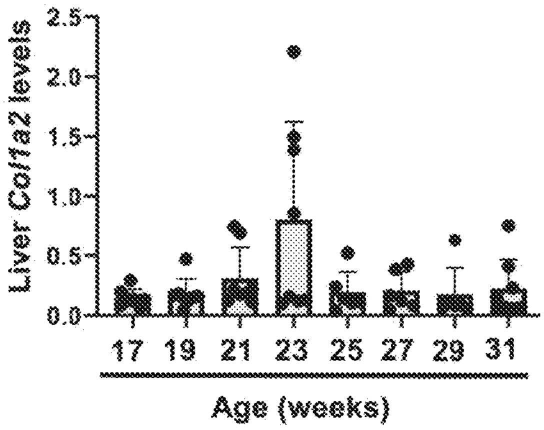
Figure 4N:
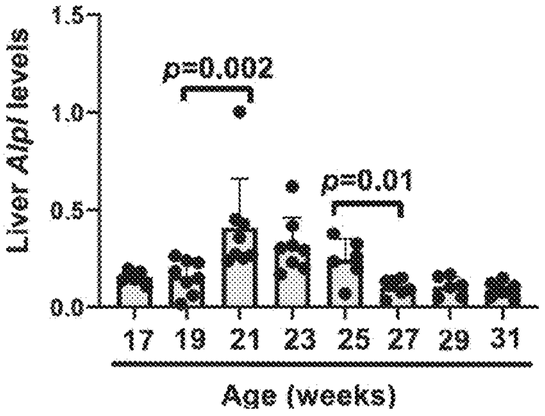
Figure 4O:
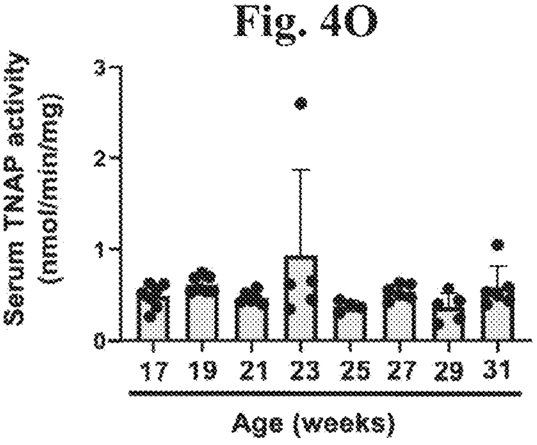

In order to better understand the functions of TNAP in the liver, how liver TNAP is regulated during the development of NASH induced by HFD in ApoE-deficient mice was characterized. Fasting serum cholesterol levels were relatively stable from 17 to 31 weeks in ApoE-deficient mice (FIG. 4A) and about 10-times higher than in wild-time mice given the same HFD. Liver cholesterol levels increased from 17 to 25 weeks, to then decrease from 27 to 31 weeks (FIG. 4B). This late decrease in liver cholesterol content was concomitant with the accumulation of cholesterol's degradation products, bile acids, indicative of cholestasis (FIG. 4C). Fasting serum and liver TGs evolved similarly, with two troughs at 19 and 27 weeks separated by about a month of higher serum and liver levels between 21 and 25 weeks (FIGS. 4D and 4E). Liver levels of inflammatory transcripts (Ly6g, Tnfa, Il1b) suggested two peaks of inflammation at 19 and 27 weeks (FIGS. 4F-4I), which were apparently not associated with a significant systemic inflammation (i.e., no change in haptoglobin liver or serum levels (FIG. 4F-4J). In contrast, these two inflammatory waves seemed associated with increases in blood glucose levels (FIG. 4K). It was confirmed that Alpl was overexpressed with the fibrosis markers Tgfb1, and Colla1, and concomitantly with rises of liver TGs and cholesterol, and between the two inflammation waves (FIGS. 4L-4N). Liver TNAP was probably active locally because serum TNAP activity was not significantly increased (FIG. 4O).

Figure 5:
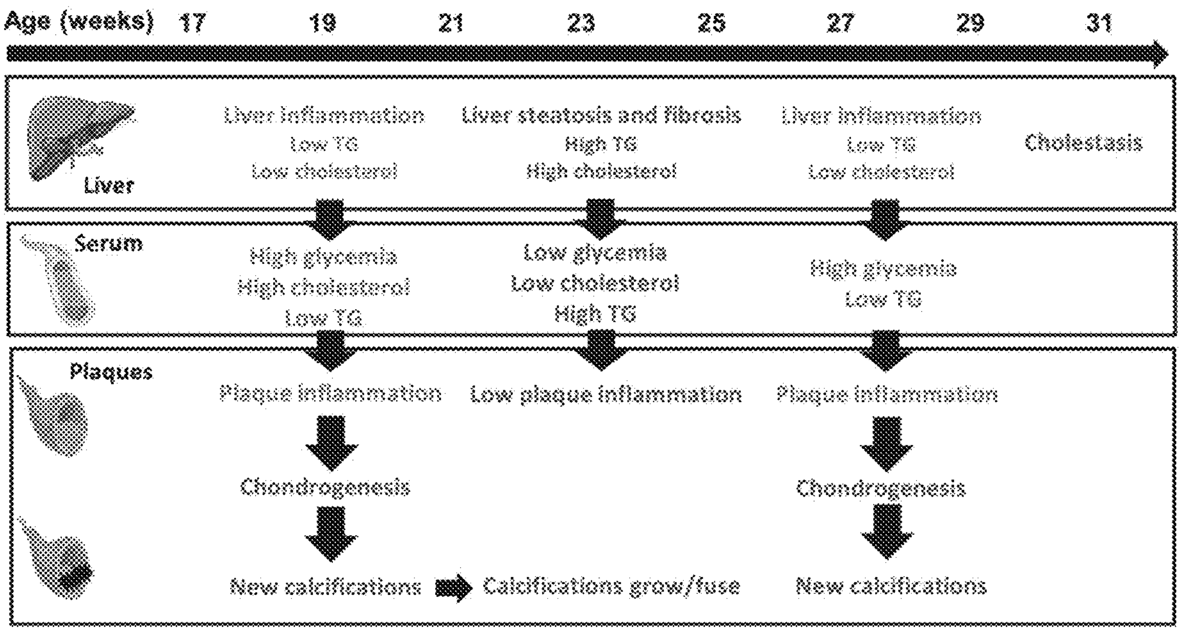
FIG. 5 illustrates a hypothetical model in ApoE-deficient mice, linking liver metabolism to serum levels of metabolic and inflammatory factors and atherosclerotic plaque development. TG: triglycerides.

Taking into account the time-course changes in the liver, the blood and the aorta, a hypothetical model linking liver metabolism to plaque development was drawn (FIG. 5). In this model, liver inflammation triggered increases in fasting glycaemia, which enhanced plaque inflammation, chondrogenesis and calcification. Plaque inflammation indeed appears to drive plaque calcification in ApoE-deficient mice. Moreover, it was observed that in the aorta, the waves of chondrogenesis and calcification were associated with simi- D. Liver TNAP May Impact Serum Lipid Levels by Participating in Liver Phosphatidylcholine Metabolism.

Figure 6A:
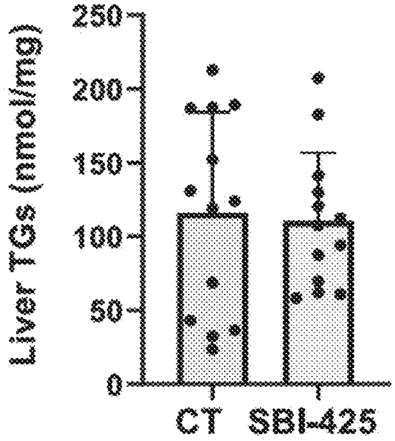
FIGS. 6A, 6H, 6J, 6K, 6Q, and 6S illustrate Quantification in the liver of ApoE-deficient mice at 25 weeks of levels of TGs (FIG. 6A), haptoglobin (FIG. 6H), hydroxyproline (FIG. 6J), cholesterol (FIG. 6K), bile acids (FIG. 6Q), phosphocholine (FIG. 6S) (n=13 CT mice and n=13 SBI-425 treated mice). Quantification in the kidney of ApoE-deficient mice of phosphocholine levels (FIG. 6T).
Figure 6B:
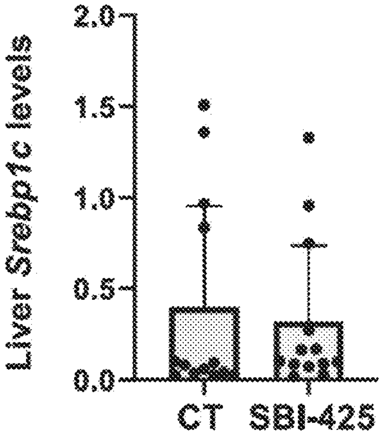
FIGS. 6B-6G and 6L-6P illustrate quantitative PCR determination of relative transcript levels in the liver in ApoE-deficient mice treated or not with SBI-425.
Figure 6C:
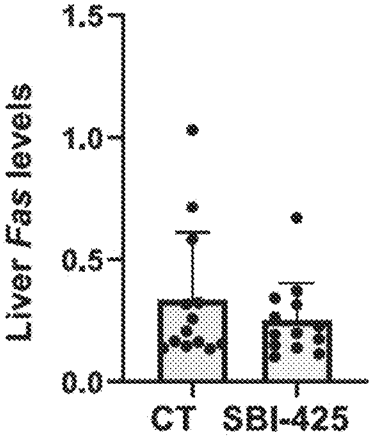
Figure 6D:
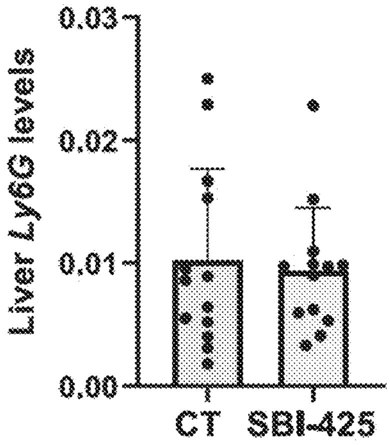
Figure 6E:
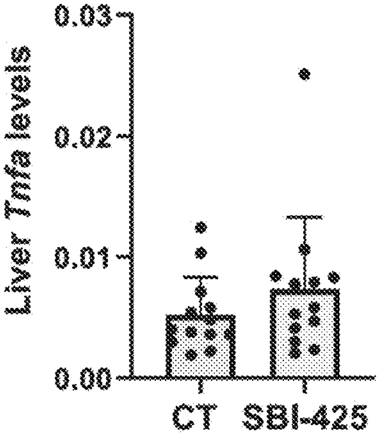
Figure 6F:
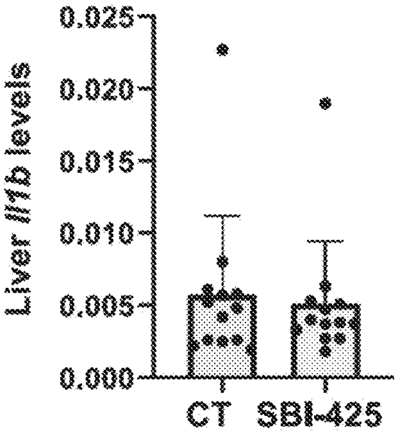
Figure 6G:
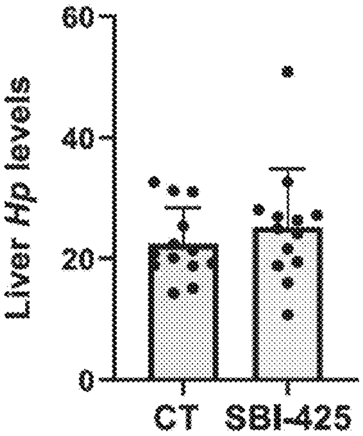
Figure 6H:
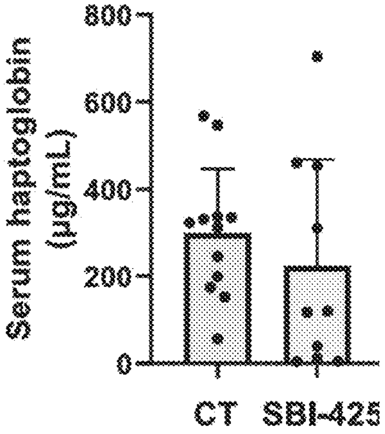
Figure 6I:
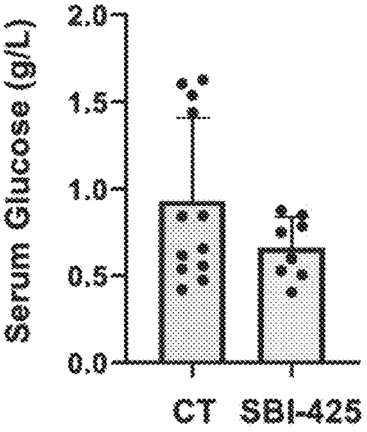
FIG. 6I illustrates the change in the serum glucose level by SBI-425 treatment.
Figure 6J:
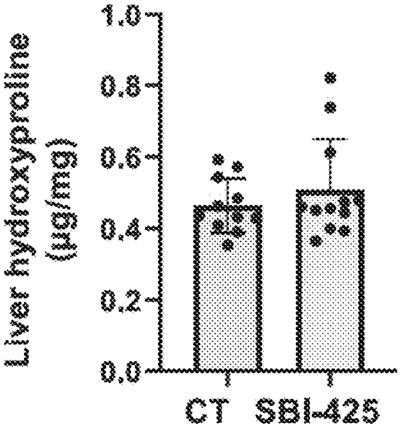
Figure 6K:
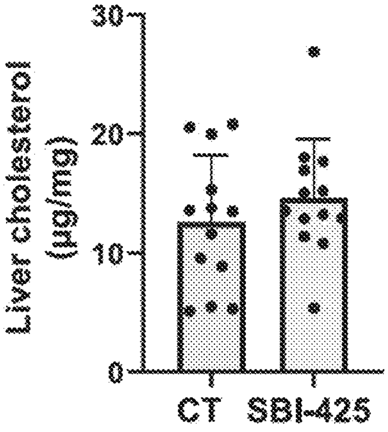
Figure 6L:
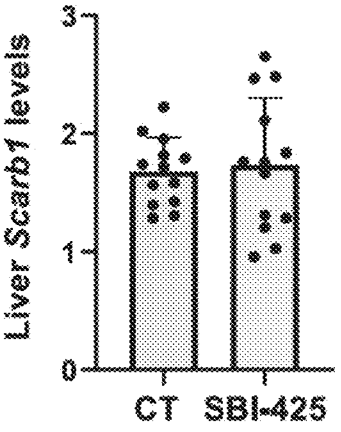
Figure 6M:
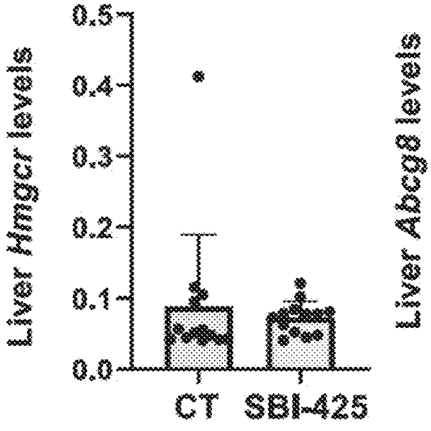
Figure 6N:
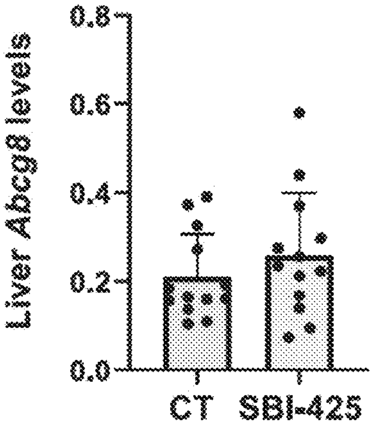
Figure 6O:
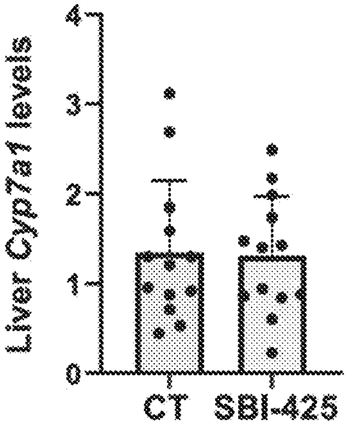
Figure 6P:
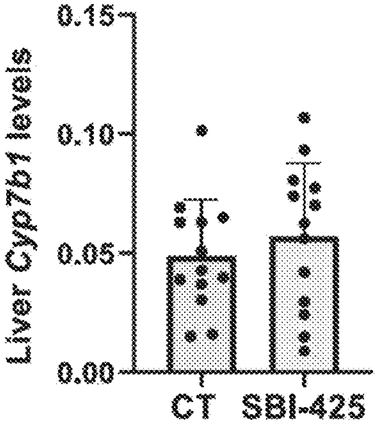
Figure 6Q:
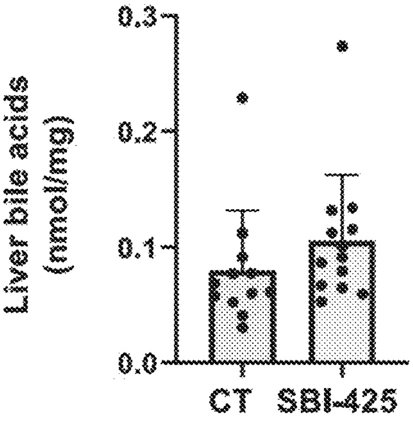
Figure 6R:
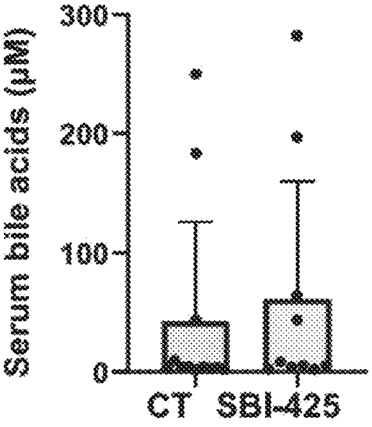
FIG. 6R illustrates the change in the serum bile acids levels by SBI-425 treatment. Results are shown as mean±standard deviation, and statistical analyses were performed with student's t-test. Correlations were calculated with Pearson's test. TG: triglycerides.

Since TNAP-deficient mice may develop liver steatosis when fed a HFD, it was suspected that SBI-425 decreased serum TGs by sequestrating them in the liver. This, however, proved irrelevant because liver TG content was not increased by TNAP inhibition (FIG. 6A), nor were the levels of transcripts associated with fatty acid synthesis (Srebp1c, Fas) (FIGS. 6B-6G) changed. TNAP inhibition neither exacerbated liver inflammation, as demonstrated by unchanged levels of Ly6g, Tnfa, Il1b, or Hp transcripts (FIGS. 6B-6G), nor changed serum haptoglobin levels (FIG. 6H). SBI-425 treatment did not modulate fasting glycemia (FIG. 6I), nor exacerbated liver fibrosis, as indicated by unchanged hydroxyproline levels (FIG. 6J). Finally, TNAP inhibition did not seem to impact cholesterol and bile acid metabolism, because SBI-425 did not change liver cholesterol levels (FIG. 6K), transcript levels of Scarb1, Hmgcr, Abcg8, Cyp7a1 or Cyp7b1 (FIGS. 6L-6P), or liver and serum bile acids levels (FIGS. 6Q and 6R).

Figure 6S:
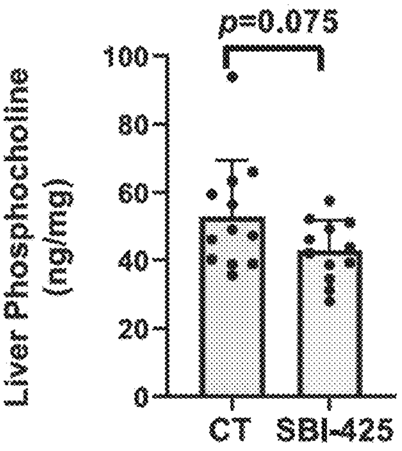
Figure 6T:
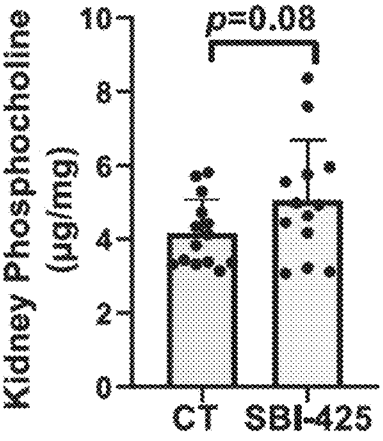
FIGS. 6U and 6V illustrate a correlation between liver and kidney phosphocholine levels, in untreated mice (left) or mice treated with SBI-425 (right).
FIGS. 6W and 6X illustrate dephosphorylation of phosphocholine or phosphoethanolamine by mouse (FIG. 6W) or human (FIG. 6X) TNAP in presence or absence of MLS-0038949.
FIGS. 6Y and 6Z illustrate an association between liver phosphocholine levels and liver levels of TGs or cholesterol.
Figure 6U:
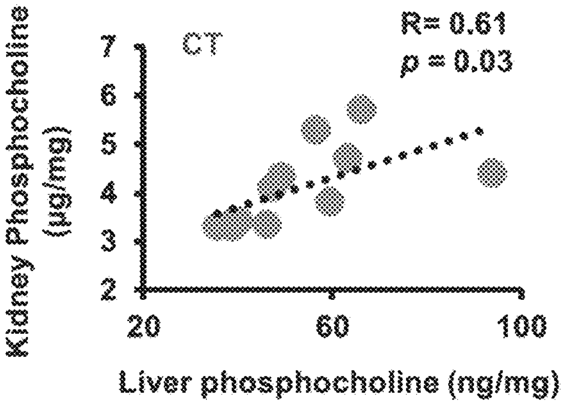
Figure 6V:
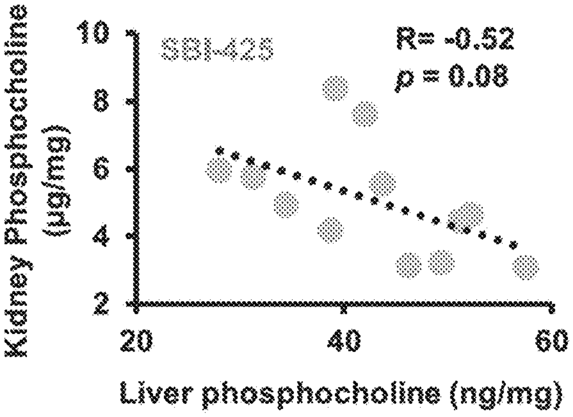
Figure 6W:
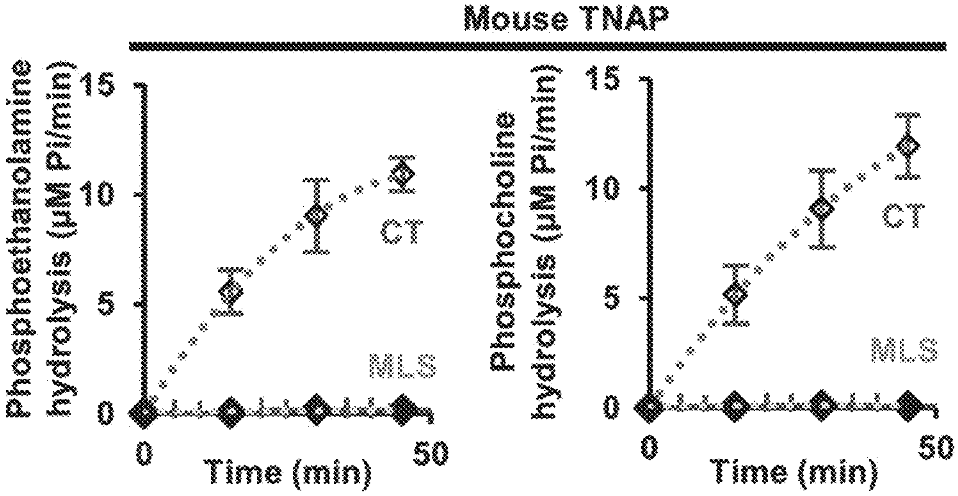
Figure 6X:
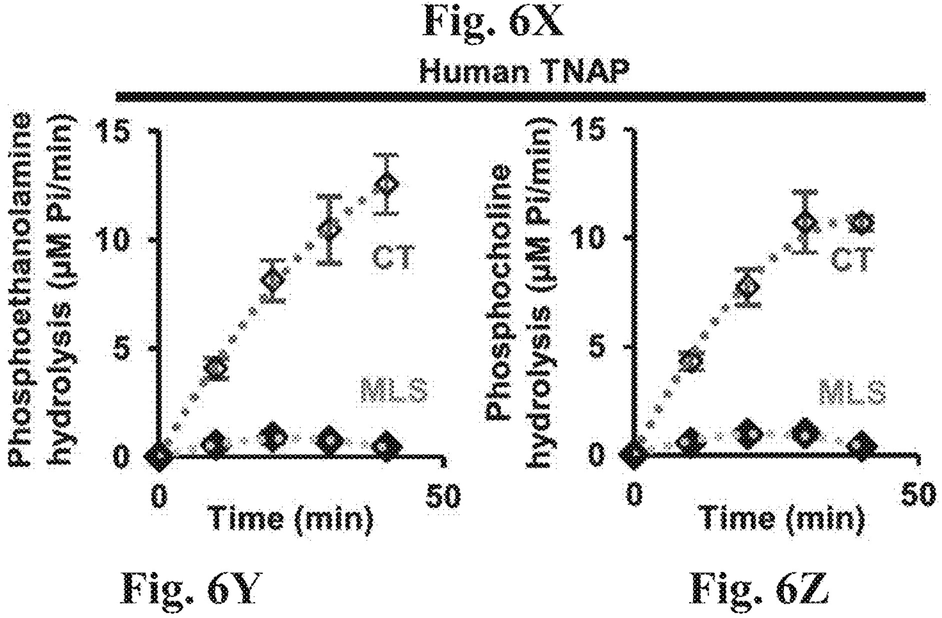
Figure 6Y:
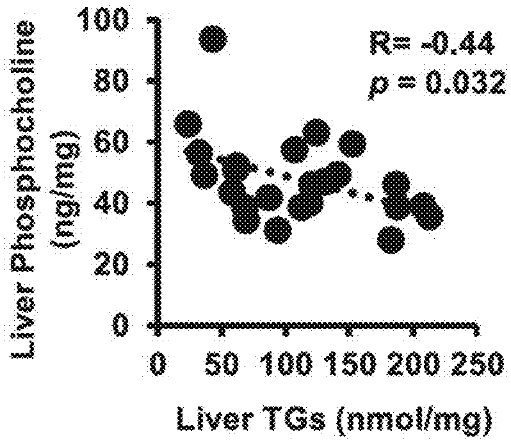
Figure 6Z:
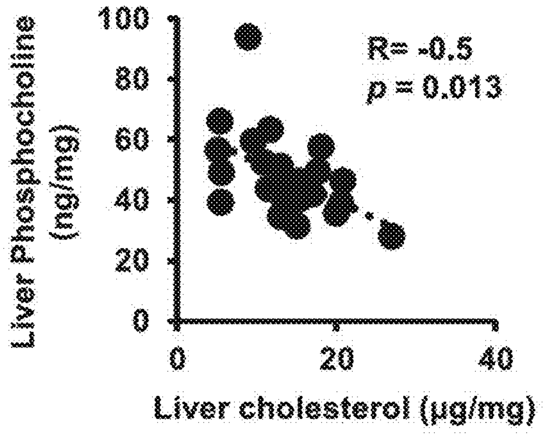

To identify unsuspected mechanisms explaining how TNAP inhibition might have decreased serum lipids, a metabolomics approach was used to determine metabolites in the liver and kidneys whose levels were significantly impacted by SBI-425 administration. Multivariate statistical analysis on metabolomics data (PLS-DA) did not evidence a significant impact of TNAP inhibition on liver or kidney metabolism (FIGS. 10A-10Z and 11A-11D). Nevertheless, liver phosphocholine levels decreased (FIG. 6S), and kidney phosphocholine levels increased (FIG. 6T). Extracellular phosphocholine dephosphorylation in the liver may be necessary to allow choline uptake in hepatocytes, intracellular reformation of phosphocholine, and generation of phosphatidylcholine, which is required for VLDL production and release. Choline-deficient diets or genetic deficiency in liver phosphatidylcholine production result in liver steatosis, reduced VLDL levels and impaired atherosclerosis in ApoE-deficient mice. It was observed that while liver and kidney phosphocholine levels were positively correlated in control animals, they were negatively associated in mice treated with SBI-425 (FIGS. 6U and 6V), suggesting that choline that could not enter into the liver was taken up by other tissues including the kidney. The phosphatase that dephosphorylates phosphocholine in the liver and allows the uptake of choline in hepatocytes is unknown in the relevant field. In these experiments, mouse and human TNAP were equally potent in dephosphorylating phosphocholine (FIGS. 6W and 6X), suggesting that TNAP is that phosphatase. This hypothesis appears moreover strengthened by the fact that liver phosphocholine levels were negatively associated with liver levels of TGs and cholesterol (FIGS. 6Y and 6Z). Finally, if extracellular choline is the main source of phosphatidylcholine in hepatocytes, extracellular phosphoethanolamine is also used to a lesser extent to generate phosphatidylcholine intracellularly. The phosphatase responsible for phosphoethanolamine dephosphorylation and ethanolamine uptake in hepatocytes is also unknown, and again could be TNAP. Indeed, mouse and human TNAP were both able to dephosphorylate phosphoethanolamine (FIGS. 6W and 6X).

An emerging paradigm indicates that microcalcifications that form in early atherosclerotic lesions destabilize plaques by exerting mechanical and pro-inflammatory stresses. TNAP has emerged as a likely candidate responsible for the initiation of plaque calcification. In this study, it was observed that TNAP was already expressed in human carotid arteries devoid of atherosclerotic lesions and that in carotid plaques, calcifications were consistently associated with TNAP expression. TNAP was also expressed before calcification could be observed in mouse atherosclerotic plaques, and when calcifications were present, they colocalized with TNAP activity. In both species, TNAP appeared to be mainly expressed in RUNX2-expressing cells. In mice, these cells were likely VSMC-derived hypertrophic chondrocytes; in humans, they were probably VSMCs transdifferentiated into osteochondrocyte-like cells. Nevertheless, cells from both species probably used TNAP to induce plaque calcification. TNAP inhibition indeed prevented calcification in human VSMCs transdifferentiated into osteochondrocyte-like cells, and in ApoE-deficient mice. Therefore, it was reasonably concluded that TNAP is not only required for the physiological mineralization of bones and teeth, but that it is also responsible for the calcification of atherosclerotic plaques. Moreover, in this study, histological data suggest that TNAP is involved locally, and the fact that in mice, blood TNAP activity was not at all associated with waves of aortic calcification, suggested that TNAP does not induce calcification from the circulation. This would mean that the association between serum TNAP activity and the cardiovascular mortality risk does not rely on enhanced plaque calcification but maybe on a function of TNAP in the liver. The conclusion that circulating TNAP may not participate in plaque calcification is further supported by the observation that the very high blood TNAP activity resulting from administration for 8 months of recombinant TNAP in a patient with TNAP deficiency, did not increase the vascular calcium score.

In addition to preventing plaque calcification, TNAP inhibition also reduced plaque inflammation and size. Since microcalcifications may be proinflammatory, it may be concluded that the prevention of plaque calcification was the cause of reduced plaque inflammation. However, it believed that TNAP inhibition mainly decreased plaque inflammation by reducing the levels of serum lipids and impairing the entire development of atherosclerotic plaques. Plaque inflammation indeed appears to drive plaque calcification in ApoE-deficient mice as well as mineralization in cultured human VSMCs. In contrast, while the smallest calcifications could be proinflammatory, they may grow rapidly and lose their pro-inflammatory capacity. The result in this study indicates that the calcification activity in the aorta measured with $^{18}F$—NaF μPET, but not the calcium volume measured with CT, positively correlated with the aortic levels of inflammation markers and chondrocyte markers. In addition, macrophages were more numerous in plaque regions with no or with small calcifications than in regions with advanced calcifications, in agreement with a recent study on human carotids. Finally, when in some mice the whole aortic arch was calcified, it was devoid of inflammatory cells, necrotic and lipid cores. Again, this mouse results confirmed that when considered as a percentage of the total plaque volume, increasing plaque calcification is a marker of plaque stability and reduced risk at both a lesion and patient level. Collectively, these data suggest that inflammation is the chicken, and calcifications are the eggs, and that SBI-425 decreased plaque inflammation by inhibiting liver TNAP and decreasing lipidemia.

TNAP is active in mouse liver, and its activity seems to be increased during liver fibrosis. TNAP's hepatic functions are poorly understood and may include regulation of bile excretion, and/or prevention of pathological liver inflammation, fibrosis and steatosis. In mice fed a HFD, the increase in TNAP expression during liver fibrosis may be associated with increased dephosphorylation and detoxification of lipopolysaccharide (LPS) by TNAP. Postprandial LPS absorption may be increased after high fat meals and its dephosphorylation in the intestinal lumen by intestinal alkaline phosphatase (IAP) reduces metabolic endotoxemia and metabolic syndrome in mouse. It is therefore conceivable that liver TNAP accomplishes the same function as IAP, but after LPS absorption. This TNAP function, however, may be absent in the mice in this study, or at least not responsible for reduced blood lipidemia upon TNAP inhibition. If it was observed that TNAP expression probably increased during the phase of liver fibrosis, TNAP inhibition did not increase serum LPS nor exacerbated liver inflammation. Moreover, increased liver inflammation would be expected to increase, not decrease, blood cholesterol and atherosclerosis.

Significant effects of SBI-425 on the liver, including inflammation, steatosis, fibrosis or cholestasis were not detected. In a way, this is reassuring by suggesting that SBI-425 did not worsen steatohepatitis. On the other hand, the subtle effects exerted by SBI-425 on the liver may propose a hypothetical mechanism. Among the many measurements made in the liver, only the levels of phosphocholine showed variations close to significance. Interestingly, TNAP could be the yet unknown phosphatase that dephosphorylates phosphocholine in the liver and allows its uptake in liver cells. This hypothesis is appealing because choline deficiency or genetic deficiency in liver phosphatidylcholine production reduces blood cholesterol levels and impairs atherosclerosis in ApoE-deficient mice. Moreover, while in absence of extracellular choline, extracellular ethanolamine can be used to generate phosphatidylcholine in the liver, TNAP could also be the phosphatase that dephosphorylate extracellular phosphoethanolamine and allows its uptake. This may explain why individuals with genetic TNAP deficiency have increased serum and urine phosphoethanolamine levels. This study indicates that mouse and human TNAP were equally able to dephosphorylate phosphocholine and phosphoethanolamine in vitro, and that in vivo, TNAP inhibition decreased the intracellular levels phosphocholine in the liver, what would be expected if extracellular phosphocholine dephosphorylation was inhibited. Being a phosphatase with broad substrate specificity, TNAP may exert other functions in the liver acting on other phosphorylated molecules. Since increased serum TNAP activity is generally indicative of cholestasis, and since TNAP may participate in the arrest of bile excretion, it is hypothesized that TNAP inhibition enhances cholesterol excretion through bile acids, and in this way decreases liver lipid levels.

In aortas from ApoE-deficient mice, as well as in human carotids, plaque calcifications consistently colocalized with TNAP. In human VSMCs, TNAP inhibition prevented calcification. In mice, TNAP inhibition prevented plaque calcification, decreased plaque inflammation and lipid accumulation, in association with reduced levels of serum cholesterol and triglycerides. Importantly, these beneficial effects of TNAP inhibition occurred without significantly impacting the skeleton, kidneys, and liver. Metabolomics analysis of liver extracts identified phosphocholine as a likely substrate of liver TNAP, whose reduced dephosphorylation upon TNAP inhibition may have influenced the reduced release of cholesterol and triglycerides into the blood, and reduction in plaque development.

This demonstrates that the systemic inhibition of TNAP ameliorates atherosclerosis acting on both vascular and liver TNAP. TNAP inhibition prevents calcification of atherosclerotic plaques. Moreover, TNAP inhibition using SBI-425 impedes plaque calcification and development. As such, the methods disclosed herein are useful to prevent or arrest the development of plaque calcification in patients with atherosclerosis, which reduces the risk of heart disease and mortality.

This example shows that TNAP inhibition with SBI-425 ameliorated atherosclerosis in mice with reduced plaque size, inflammation, and calcification. SBI-245 acts in part by inhibiting TNAP in plaques and preventing calcification, and in another part by inhibiting liver TNAP and reducing blood cholesterol. In the mouse experiments, administration of SBI-425 for several months did not significantly change bone architectural parameters, liver and kidney metabolism, systemic inflammation, or body weight.

What is claimed is:

1. A method of treating atherosclerosis comprising administering a pharmaceutical composition comprising a therapeutically effective amount of a tissue-nonspecific alkaline phosphatase (TNAP) inhibitor to a patient, wherein the patient is a human.

2. The method of claim 1, wherein treating atherosclerosis comprises reducing a number of microcalcifications in an atherosclerotic plaque, wherein administering the pharmaceutical composition comprising the therapeutically effective amount of the TNAP inhibitor reduces the number of microcalcifications in the atherosclerotic plaque, or wherein treating atherosclerosis comprises preventing, arresting, or reducing the development of plaque calcifications, wherein administering the pharmaceutical composition comprising the therapeutically effective amount of the TNAP inhibitor prevents, arrests, or reduces the development of plaque calcifications.

3. The method of claim 1, wherein the TNAP inhibitor is selected from the group consisting of a TNAP-targeting short hairpin RNA (shTNAP), a TNAP-targeting guide RNA (sgTNAP), and a small molecule.

4. The method of claim 3, wherein the TNAP inhibitor is a shTNAP, and the shTNAP is doxycycline-inducible.

5. The method of claim 1, wherein the TNAP inhibitor is a small molecule.

6. The method of claim 5, wherein the small molecule is a compound of Formula I, or a pharmaceutically acceptable salt thereof:

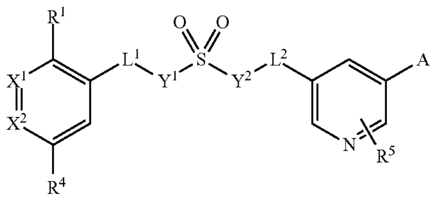

wherein:

$Y^1$ and $Y^2$ are independently a bond or —N($R^6$)—, wherein at least one of $Y^1$ and $Y^2$ is —N($R^6$)—;

$L^1$ and $L^2$ are independently a bond or optionally substituted alkylene;

$X^1$ is =N— or =C($R^2$)—;

$X^2$ is =N— or =C($R^3$)—;

$R^1$ and $R^4$ are independently selected from the group consisting of hydrogen, halogen, —CN, —C(O)—N($R^7$)—$R^8$, —C(O)—O—$R^9$, optionally substituted alkyl, optionally substituted cycloalkyl, optionally substituted heterocycloalkyl, optionally substituted alkoxy, haloalkyl, haloalkoxy, optionally substituted phenyl, and optionally substituted 5- or 6-membered heteroaryl;

$R^2$, $R^3$, and $R^5$ are independently selected from the group consisting of hydrogen, halogen, —CN, —C(O)—N($R^7$)—$R^8$, —C(O)—O—$R^9$, optionally substituted alkyl, optionally substituted cycloalkyl, optionally substituted heterocycloalkyl, optionally substituted alkoxy, haloalkyl, haloalkoxy, optionally substituted phenyl, and optionally substituted 5- or 6-membered heteroaryl;

$R^6$ is hydrogen, optionally substituted alkyl, optionally substituted alkenyl, or optionally substituted alkynyl;

$R^7$ and $R^8$ are independently hydrogen, optionally substituted alkyl, haloalkyl, optionally substituted cycloalkyl, optionally substituted heterocycloalkyl, optionally substituted phenyl, or $R^7$ and $R^8$ together with the nitrogen atom to which they are attached form an optionally substituted heterocycloamino;

$R^9$ is selected from the group consisting of hydrogen, optionally substituted alkyl, haloalkyl, optionally substituted cycloalkyl, optionally substituted heterocycloalkyl, and optionally substituted phenyl; and A is selected from the group consisting of —C(O)—N($R^7$)—$R^8$, —C(O)—O—$R^9$, optionally substituted phenyl, and optionally substituted 5- or 6-membered heteroaryl.

7. The method of claim 1, wherein the pharmaceutical composition is administered to a subject via a route selected from the group consisting of subcutaneous injection, intramuscular injection, and intravenous injection.

8. The method of claim 1, wherein the pharmaceutical composition further comprises a delivery vehicle selected from the group consisting of liposomes, nanoparticles, microparticles, microspheres, lipid particles, vesicles, poloxamers, and polycationic materials.

9. The method of claim 1, wherein the subject is diagnosed with an obesity-related condition.

10. The method of claim 9, wherein the obesity-related condition is selected from the group consisting of obesity-related insulin resistance and Type-2 diabetes.

11. The method of claim 1, wherein the method comprises administering the pharmaceutical composition in combination with a lipid-lowering agent.

12. The method of claim 11, wherein the lipid-lowering agent is a statin.

13. The method of claim 12, wherein the statin is selected from the group consisting of lovastatin, pravastatin, simvastatin, atorvastatin, cerivastatin, fluvastatin, pravastatin, pitavastatin, and rosuvastatin.

14. The method of claim 1, further comprising measuring a biomarker in a biological sample obtained from an individual prior to administering the therapeutically effective amount of the TNAP inhibitor.

15. The method of claim 14, wherein measuring the biomarker comprises assaying mRNA expression level of the biomarker.

16. The method of claim 15, wherein measuring the biomarker comprises assaying protein level of the biomarker.

17. The method of claim 1, wherein the TNAP inhibitor is SBI-425.

18. The method of claim 1, wherein the TNAP inhibitor is MLS-0038949.

19. The method of claim 1, wherein the TNAP inhibitor is administered from 10 to 40 mg/kg/day.

* * * * *